United States Patent [19]

Kwak et al.

[11] Patent Number: 5,756,765
[45] Date of Patent: May 26, 1998

[54] 2-(2-SUBSTITUTED PYRROLIDIN-4-YL) THIO-CARBAPENEM DERIVATIVES

[75] Inventors: Hyo Sung Kwak; Chong Ryul Lee, both of Seoul; Sang Choon Lee, Kyeongki-do; Hong Woo Lee, Kwangmyeong; Hoi Choo Son, Suwon; Eung Nam Kim; Kyeong Bok Min, both of Seoul, all of Rep. of Korea

[73] Assignee: Chong Kun Dang Corp., Seoul, Rep. of Korea

[21] Appl. No.: 818,233

[22] Filed: Mar. 14, 1997

Related U.S. Application Data

[62] Division of Ser. No. 448,555, filed as PCT/KR93/00114, Dec. 20, 1993, Pat. No. 5,641,770.

[30] Foreign Application Priority Data

Dec. 21, 1992 [KR] Rep. of Korea .................. 1992/24838
May 25, 1993 [KR] Rep. of Korea .................. 1993/09017
Jun. 30, 1993 [KR] Rep. of Korea .................. 1993/12009

[51] Int. Cl.[6] .................................................. C07D 207/12
[52] U.S. Cl. ........................ 548/556; 548/568; 548/569; 544/372; 546/208

[58] Field of Search ....................... 548/568, 569, 548/556; 514/424; 544/372; 546/208

[56] References Cited

U.S. PATENT DOCUMENTS 4,613,595  9/1986  Miyadera et al. .

FOREIGN PATENT DOCUMENTS 0 182 213  5/1986  European Pat. Off. .
0 243 686  11/1987  European Pat. Off. .
0 280 771  9/1988  European Pat. Off. .
657 853    8/1982  Switzerland .

Primary Examiner—Rebecca Cook
Attorney, Agent, or Firm—Banner & Witcoff, Ltd.

[57] ABSTRACT

The present invention relates to a mercaptopyrrolidinyl derivative of the following formula

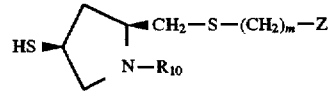

suitable for the preparation of carbapenem compounds.

1 Claim, No Drawings

2-(2-SUBSTITUTED PYRROLIDIN-4-YL)THIO-CARBAPENEM DERIVATIVES

This application is a divisional of application Ser. No. 08/448,555, filed Jul. 21, 1995 now U.S. Pat. No. 5,641,770 which is a 371 of PCT/KR93/00114 filed Dec. 20, 1993.

TECHNICAL FIELD

The present invention relates to a novel carbapenem derivative useful as a therapeutic agent for treatment of bacterial infectious diseases in pharmacological field.

BACKGROUND ART

Recently, beta-lacatam antibiotics having a beta-lactam ring in their structurs as in penicillin derivaties have been discovered in the natural world. As the typical example thereof, thienamycin having the following structural formula was first isolated by fermentation of microorganism *Streptomyces cattleya* (Journal of American. Assoc. Vol. 100, p6491, 1978).

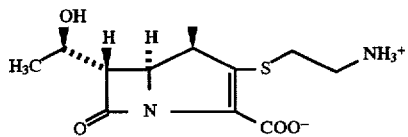

Thienamycin=[5R-[5α, 6α(R*)]]-3-[(2-aminoethyl)-thio]-6-(1-hydroxyethyl)-7-oxo-1-azabicyclo[3.2.0]-hept-2-ene-2-carboxylic acid According to the result of antimicrobial activity test, has been identified that thienamycin exhibits a broad and potent antimicrobial activity against gram-positive and gram-negative bacteria. Thus, thienamycin was expected as a beta-lactam antibiotic substance having a high clinical utility. However, it has been reported that since thienamycin itself is chemically unstable and can be readily decomposed in vivo by dehydrogenase-1(DHP-I enzyme) present in kidney, when thienamycin is clinically administered, antibacterial activity in vivo exhibits a tendency to reduce and the recovery rate in urine is extremely low (Antimicro. Agent. Chemother. Vol 22, p62, 1982). Thus, in order to prepare the compound having an improved chemical stability while maintaining a good-antibacterial activity of thienamycin numerous thienamycin derivatives have been synthesized. Among such thienamycin derivatives, particularly imipenem, i.e. (5R, 6S, 8R)-3-[[2-(formimidoylamino)ethyl]thio]-6-(1-hydroxyethyl)-7-oxo-1-azabicyclo[3.2.0]hept-ene-2-carboxylic acid hydrate which is prepared by formylating an amino group in thienamycin, exhibits antibacterial activity equivalent to, or higher than, that of thienamycin against various bacteria including beta-lactamase producing strains and particularly a potent antibacterial activity against *Pseudomonas aeruginosa*, which is 2 to 4 times stronger than that of thienamycin and further shows a slightly improved stability in a solution in comparison withy thienamycin. Accordingly, imipenem was developed as a Pharmaceutical medicament which can be practically and clinically utilized (J. Med. Chem. Vol. 22, p1435, 1979). However, since imipenem can be readily decomposed by DHP-I enzyme present in human kidney as like as thienamycin, it cannot be used for treatment of urinary tract infection and further, substances produced by DHP-I enzyme decomposition can induce a serious renal toxicity. Accordingly, imipenem cannot be administered alone and should be administered together with DHP-I enzyme inhibitors such as cilastatin (J. Antimicrob. Chemo. Vol. 12 (Suppl. D) pl (1983)). Moreover, recently a frequent use of imipenem for prophylaxis and treatment of infectious diseases results in remarkable increase of imipenem-resistant Straphylococcus aureus and *Pseudomonas aeruginosa* strains in clinical field. Imipenem cannot provide a suitable therapeutic effect on diseases caused by such resistant strains.

As a result of an effort to solve such disadvantages, many antibiotics having chemical structure and pharmacological activity similar to imipenem but not having the above-mentioned disadvantages involved in imipenem have been developed. For example they are disclosed in European Patent Nos. 411664A, 272456, 272457, 280771, 341557 and the like. Among these patent specifications, European Patent No. 411664A discloses a carbapenem compound having 2-[2-(aminocarbonyl)vinyl]pyrroldin-4-yl]-thio group at 2-position of a carbapenem basic structure with a specific example of (1R, 5S, 6S)-2-[(2S, 4S)-2-[(E)-2-(aminocarbonyl)vinyl]-pyrrolidin-4-yl-thio]-6-[(R)-1-hydroxyethyl]-1-methyl-1-carbapen-2-em-3-carboxylic acid (Bo-2171, compound of Example 3). Such beta-lactam antibiotics generally exhibit a toxic effect selectively only on pathogenic bacteria with substantially no toxic effect on animal cells. Accordingly, they have been broadly and safely used for treatment of infectious diseases caused by bacteria for clinical purpose. However, since these beta-lactam antibiotics do not sufficiently exhibit a satisfactory antibacterial effect on causative microorganisms for incurable infectious disease, such as Staphylococcus aureus and *Pseudomonas aeruginosa* which are resistant to methicillin, their clinical use is greatly restricted, particularly in immunodeficient patients from which such resistant strains are frequently isolated. Further, although such known antibiotic compounds have a resistance to DHP-I enzyme to some extent, it is not sufficient to the desired extent. Accordingly, the development of antibiotic compounds showing an improved antibacterial activity against such resistant strains has been continuously required. Specifically, the major aspect of development of a novel carbapenem antibiotic compound resides in an increase of resistance against DHP-I enzyme and a reduction of renal toxicity and side effects on central nervous system as well as an increase of antibacterial activity.

DISCLOSURE OF INVENTION

Thus, the present inventors have conducted an extensive study to provide a novel carbapenem compound showing an excellent antibacterial activity and a strong resistance against DHP-I enzyme. As a result, we have found that a novel group of carbapenem compounds having a moiety of the following formula (A) at 2-position of carbapenem structure satisfies the above-mentioned requirement and then completed the present invention:

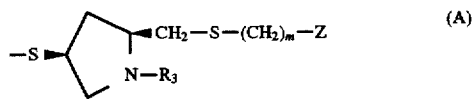

wherein
$R_3$ represents hydrogen or lower alkanimidoyl,
z represents

or $R_9$,
X represents O or NH,
$R_4$ represents amino or heterocyclic amine group, each of which can be unsubstituted or substituted with a group of formula

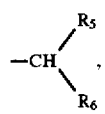

a unsubstituted or substituted heterocyclic group or a lower alkyl group, or represents hydroxy(lower)alkyl or carbamoyloxy(lower)alkyl, $R_5$ and $R_6$ independently of one another represent hydrogen, hydroxy, hydroxy(lower)alkyl, cyano, amino, carbamoyl, carbamoyl(lower)alkyl, cyano (lower)alkyl, mono- or di-(lower)alkylcarbamoyl, carbamoyloxy, ureido, amino (lower)alkyl, carbamoyloxy(lower)alkyl, mono- or di-(lower) alkylcarbamoyl-(lower alkyl, ureido(lower)alkyl, or a group of formula

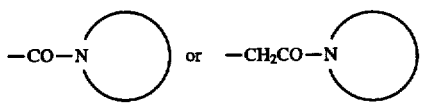

wherein

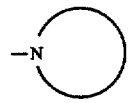

denotes a unsubstituted or substituted 3- to 6-membered heterocyclic group which can contain additional hetero atoms, provided that $R_5$ and $R_6$ cannot be hydrogen at the same time, $R_9$ represents hydroxy(lower)alkyl or carbamoyloxy, and m is an integer of 1 to 6, provided that when m is 1 and X is O, $R_4$ is other than unsubstituted amino(—$NH_2$).

A compound of formula (I), as defined below, having the partial structure (A) above is a novel compound which was not disclosed in the prior art up to now. It is identified that the compound (I) exhibits a superior antibacterial activity against both of gram-positive bacteria such as Staphylococcus aureus and gram-negative bacteria such as *Pseudomonas aeruginosa* and further shows a good stability to DHP-I enzyme.

Accordingly, it is an object of the present invention to provide a novel 2-(2-substituted pyrrolidin-4-yl)thiocarbapenem derivative represented by the following general formula (I):

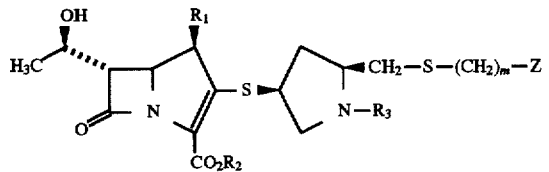

and pharmaceutically acceptable salts thereof, in which $R_1$ represents hydrogen or (lower)alkyl, $R_2$ represents hydrogen or anion, $R_3$ represents hydrogen or (lower)alkanimidoyl, Z represents

or $R_9$,

X represents O or NH, $R_4$ represents amino or heterocyclic amine group, each of which can be unsubstituted or substituted with a group of formula

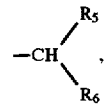

a unsubstituted or substituted heterocyclic group or a lower alkyl group, or represents hydroxy(lower) alkyl or carbamoyloxy(lower)alkyl, $R_5$ and $R_6$ independently of one another represent hydrogen, hydroxy, hydroxy(lower)alkyl, cyano, amino, carbamoyl, carbamoyl(lower)alkyl, cyano (lower)alkyl, mono- or di-(lower)alkylcarbamoyl, carbamoyloxy, ureido, amino (lower)alkyl, carbamoyloxy(lower)alkyl, mono- or di-(lower) alkylcarbamoyl-(lower)alkyl, ureido(lower)alkyl, or a group of formula

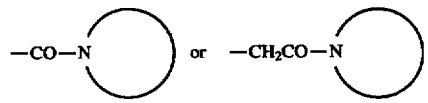

wherein

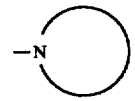

denotes a unsubstituted or substituted 3- to 6-membered heterocyclic group which can contain additional hetero atoms, provided that $R_5$ and $R_6$ cannot be hydrogen at the same time, $R_9$ represents hydroxy(lower)alkyl or carbamoyloxy, and m is an integer of 1 to 6, provided that when m is 1 and X is O, $R_4$ is other than unsubstituted amino(—$NH_2$).

Further, it is another object of the present invention to provide a process for preparation of the compound of formula (I):

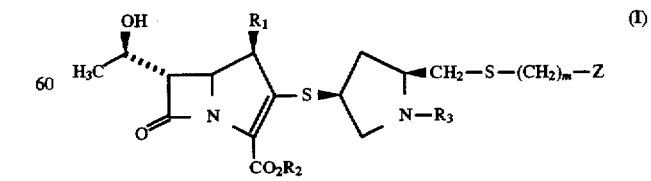

wherein $R_1$, $R_2$, $R_3$, Z and m are defined as above, or salts thereof, which comprises reacting a compound of formula (II):

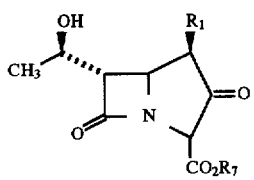

(II)

wherein R₁ is as defined above and R₇ represents a carboxy-protecting group, or a reactive derivative at the oxo group thereof or salts thereof with a compound of formula (III):

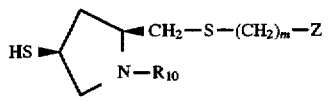

(III)

wherein Z and m are as defined above and R₁₀ represents an imino-protecting group, or salts thereof to obtain an intermediate compound of formula (IV),

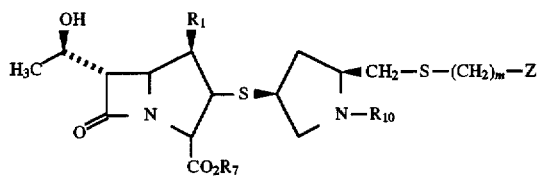

(IV)

wherein R₁, R₇, R₁₀, Z and m are as defined above, or salts thereof and subjecting the resulting compound of formula (IV) or salts thereof to elimination reaction of the carboxy- and imino-protecting groups and, if necessary, reacting the resulting compound of formula (I-b),

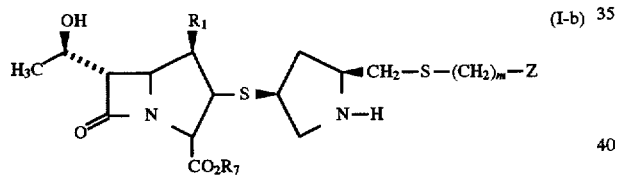

(I-b)

wherein R₁, R₂Z and m are as defined above, or salts thereof with a lower alkanimidoylating agent.

It is a further object of the present invention to provide a novel 2-substituted mercaptopyrrolidine compound represented by the following general formula (III), which is an intermediate compound useful in the preparation of the desired compound of formula (I):

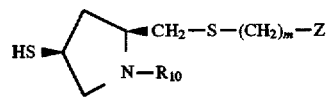

(III)

wherein Z, R₁₀ and m are as defined above, and a process for preparation thereof.

Further, it is another object of the present invention to provide a pharmaceutical composition containing a novel carbapenem compound of formula (I) as defined above.

BEST MODE FOR CARRYING OUT THE INVENTION

In one aspect, the present invention relates to a novel 2-(2-substituted pyrrolidin-4-yl)thio-carbapenem derivative of the following general formula (I):

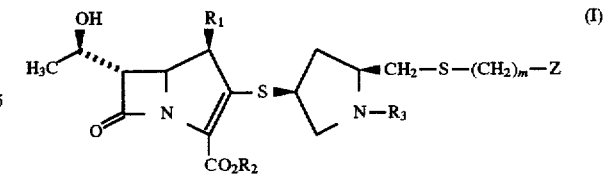

(I)

and pharmaceutically acceptable salts thereof, in which

R₁ represents hydrogen or (lower)alkyl,

R₂ represents hydrogen or anion,

R₃ represents hydrogen or (lower)alkanimidoyl,

Z represents

or R₉,

X represents O or NH,

R₄ represents amino or heterocyclic amine group, each of which can be unsubstituted or substituted with a group of formula

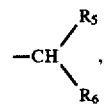

a unsubstituted or substituted heterocyclic group or a (lower)alkyl group, or represents hydroxy(lower)alkyl or carbamoyloxy(lower)alkyl, R₅ and R₆ independently of one another represent hydrogen, hydroxy, hydroxy(lower)alkyl, cyano, amino, carbamoyl, carbamoyl(lower)alkyl, cyano (lower)alkyl, mono- or di-(lower)alkylcarbamoyl, carbamoyloxy, ureido, amino-(lower)alkyl, carbamoyloxy(lower)alkyl, mono- or di-(lower) alkylcarbamoyl(lower)alkyl, ureido(lower)alkyl, or a group of formula

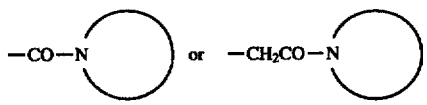

wherein

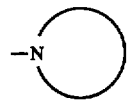

denotes a unsubstituted or substituted 3- to 6-membered heterocyclic group which can contain additional hetero atoms, provided that R₅ and R₆ cannot be hydrogen at the same time, R₉ represents hydroxy(lower)alkyl or carbamoyloxy, and m is an integer of 1 to 6, provided that when m is 1 and X is O, R₄ is other than unsubstituted amino(—NH₂)

The compound of the present invention has the following basic structure

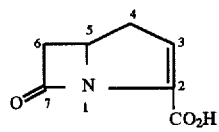

This basic structure is named 7-oxo-1-azabicyclo[3.2.0]hept-2-ene-2-carboxylic acid. In the present invention, it is named 1-carbapen-2-em-3-carboxylic acid according to the more generally and widely used nomenclature system for convenience.

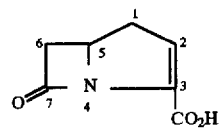

The compound of formula (I) according to the present invention includes optical isomers due to asymmetric carbon atoms present in 1-, 5-, 6- and 8-position of the carbapenem moiety and side chain bound to 6-position thereof. Among such isomeric compound, the most preferred compound is a compound having trans configuration (5S, 6S) at 5 and 6 positions, R-configuration at 8-position and R-configuration at lower alkyl group ($R_1$) present on 1-position, i.e. a compound having the whole configuration (1R, 5S, 6S, 8R).

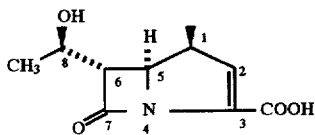

In addition, in a (2-substituted pyrrolidin-4-yl)thio group which is the side chain present on 2-position of the carbapenem structure there may be isomeric compound due to asymmetric carbon atoms present on 2- and 4-positions of pyrrolidine, among which the compound having (2S',4S') or (2R',4R') configuration is most preferable. The compound of formula (I) according to the present invention also includes isomers at pyrrolidine moiety which is the side chain present on 2-position of carbapenem structure.

The desired compound of the present invention also includes a pharmaceutically acceptable salt of the compound of formula (I). Such pharmaceutically acceptable salt may include a base-addition salt such as an inorganic base salt for example, an alkali metal salt (e.g. sodium salt, potassium salt, etc.), an alkaline earth metal salt (e.g. magnesium salt, calcium salt, etc.), etc. or an organic base salt, for example, a salt with an organic base (e.g. triethylamine salt, dicyclohexylamine salt, ethanolamine salt, pyridine salt, picoline salt, etc.); an acid-addition salt such as an inorganic acid addition salt (e.g. hydrochloride, hydrobromide, sulfate, phosphate, etc.) or an organic acid addition salt (e.g. formate, acetate, tartrate, benzenesulfonate, etc.); an intermolecular quaternary salt, and the like.

The present invention also provides a process for preparation of 2-(2-substituted pyrrolidin-4-yl)thio-carbapenem derivatives of formula (I) as defined above and salts thereof. The process for preparation of he desired compound pound of formula (I) according to the present invention can be illustrated by the following reaction scheme:

Process 1)

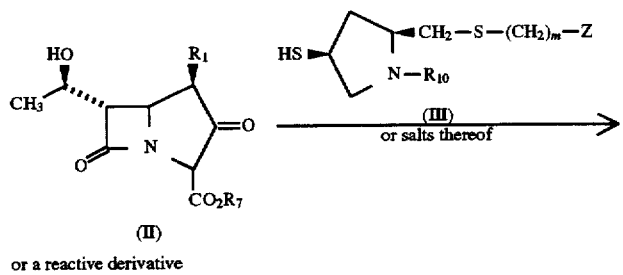

(II)
or a reactive derivative
at the oxo group thereof
or salts thereof

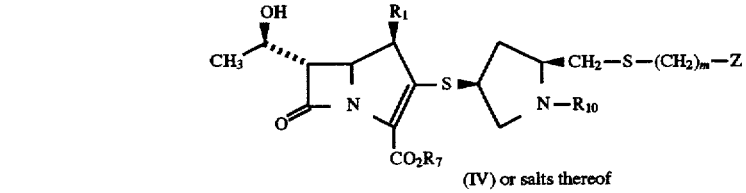

(IV) or salts thereof

Process 2)

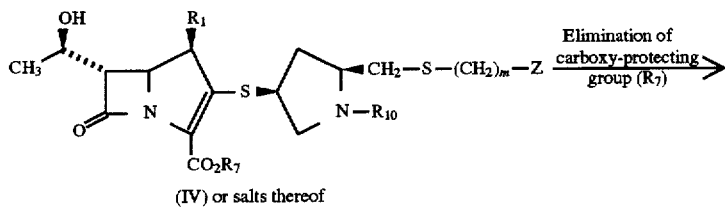

(IV) or salts thereof

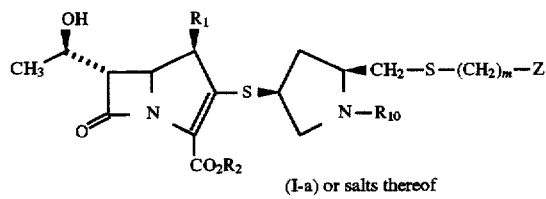

(I-a) or salts thereof

Process 3)

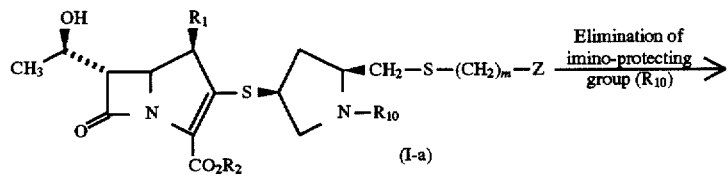

(I-a) or salts thereof

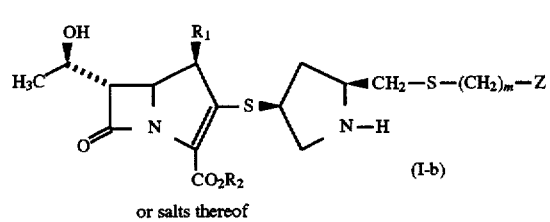

(I-b) or salts thereof

Process 4)

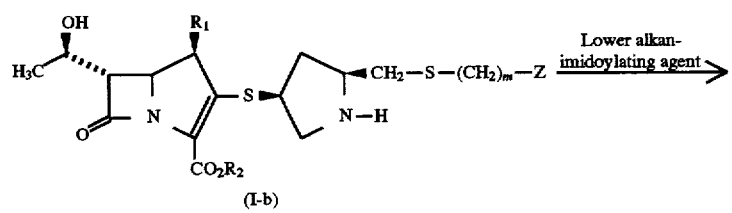

(I-b) or salts thereof

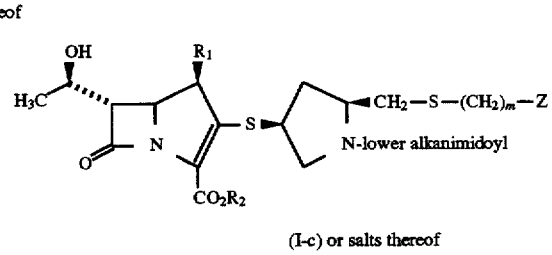

(I-c) or salts thereof

In the above reaction scheme, $R_1$, $R_2$, $R_3$, Z and m are as defined above, $R_7$ represents a carboxy-protecting group and $R_{10}$ represents an imino-protecting group.

The term "lower alkyl" as used herein is intended to mean straight or branched alkyl having 1 to 6 carbon atoms and may include, for example, methyl, ethyl, propyl, isopropyl, butyl, s-butyl, t-butyl, pentyl, hexyl, etc. Preferable lower alkyl is methyl, ethyl, propyl or t-butyl. Suitable "carbamoyl (lower)alkyl" may include, for example, carbamoylmethyl, carbamoylethyl, carbamoylpropyl, 1-(carbamoylmethyl) ethyl, 1-carbamoyl-1-methylethyl, carbamoylbutyl, 1,1-dimethyl-2-carbamoylethyl, carbamoylpentyl, carbamoylhexyl, and the like, in which preferable one is carbamoyl-($C_1$-$C_4$)alkyl and the most preferable one is carbamoylmethyl, carbamoylethyl or carbamoylpropyl.

Suitable "lower alkanimidoyl" may include straight or branched lower alkanimidoyl having 1 to 6 carbon atoms such as formimidoyl, acetimidoyl, propionimidoyl, butyrimidoyl, isovalerimidoyl, pentanimidoyl, hexanimidoyl, and the like, in which the most preferable one is formimidoyl or acetimidoyl.

Suitable caboxy-protecting group for R may include a group which can form esterified carboxy. Preferable examples of the ester moiety of an esterified carboxy may include lower alkyl ester such as methyl ester, ethyl ester, propyl ester, isopropyl ester, butyl ester, isobutyl ester, t-butyl ester, pentyl ester, hexyl ester, etc.; lower alkanoyloxy(lower)alkyl ester which may have suitable substituent(s) such as acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2, or 3)-acetoxypropyl ester, 1(or 2, or 3, or 4)-acetoxybutyl ester, 1(or 2)-propionyloxyethyl ester, 1(or 2, or 3)-propionyloxypropyl ester, 1(or 2)-butyryl oxyethyl ester, 1(or 2)-isobutyryloxyethyl ester, 1(or 2)-pivaloyloxy ethyl ester, 1(or 2)-hexanoyloxyethyl ester, isobutyryloxymethyl ester, (2-ethylbutyryl)oxymethyl ester, (3,3-dimethylbutyryl)oxymethyl ester, 1(or 2)-pentanoyloxyethyl ester, etc.; (lower)alkanesulfonyl (lower)alkyl ester; mono-(or di- or tri-)halo(lower)alkyl ester such as 2-iodoethyl ester, 2,2,2-trichloroethyl ester, etc.; lower alkoxycarbonyloxy(lower)alkyl ester such as methoxycarbonyloxymethyl ester, 2-methoxycarbonyloxyethyl ester, 1-ethoxycarbonyloxyethyl ester, 1-isopropoxycarbonyloxyethyl ester, etc.; phthalidinyl (lower)alkyl ester; (5-lower alkyl-2-oxo-1,3-dioxolan-4-yl) (lower)alkyl ester such as (5-methyl-2-oxo-1,3-dioxolan-4-yl)methyl ester, (5-ethyl-2-oxo-1,3-dioxolan-4-yl)methyl ester, (5-propyl-2-oxo-1,3-dioxolan-4-yl)ethyl ester, etc.; lower alkenyl ester such as vinyl ester, allyl ester, etc.; lower alkynyl ester such as ethynyl ester, propynyl ester, etc.; or aromatic(lower)alkyl ester which may have suitable substituent(s), for example, benzyl ester, 4-methoxybenzyl ester, 4-nitrobenzyl ester, phenylethyl ester, trityl ester, benzhydryl ester, bis(methoxyphenyl)methyl ester, 3,4-dimethoxybenzyl ester, 4-hydroxy-3,5-t-butylbenzyl ester and the like; or aryl ester which may have suitable substituents, for example, phenyl ester, 4-chlorophenyl ester, tosyl ester, t-butylphenyl ester, mesityl ester, cumenyl ester, phthalidyl ester, and the like. Among these ester moieties, particularly preferable one may be substituted aromatic (lower)alkyl ester, most preferably 4-nitrobenzyl or phenyl $(C_1-C_4)$alkyl ester.

Suitable imino-protecting group for $R_{10}$ may include acyl group such as aliphatic acyl substituted with aromatic or heterocyclic group derived from carboxylic acid, carbonic acid, sulfonic acid or carbamic acid, or carbamoyl, aliphatic acyl, aromatic acyl or heterocyclic acyl. Suitable aliphatic acyl may include saturated or unsaturated acyclic or cyclic acyl groups, for example, lower alkanoyl such as formyl, acetyl, propionyl, butyryl, isobutyryl, valeryl, isovaleryl, pivaloyl, hexanoyl, etc.; (lower)alkylsulfonyl such as mesyl, ethylsulfonyl, propylsulfonyl, isopropylsulfonyl, butylsulfonyl, isobutylsulfonyl, pentylsulfonyl, hexylsulfonyl, etc.; N-alkylcarbamoyl such as methylcarbamoyl, ethylcarbamoyl, etc.; (lower) alkoxycarbonyl such as methoxycarbonyl, ethoxycarbonyl, propoxycarbonyl, butoxycarbonyl, t-butoxycarbonyl, etc.; (lower)alkenyloxycarbonyl such as vinyloxycarbonyl, allyloxycarbonyl, etc.; (lower)alkenoyl such acryloyl, methacryloyl, crotonoyl, etc.; cyclo(lower)alkylcarbonyl such as cyclopentylcarbonyl, cyclopropylcarbonyl, cyclohexylcarbonyl, etc., and the like. Suitable aromatic acyl may include heterocyclic carbonyl such as furoyl, thienylcarbonyl, nicotinoyl, isonicotinoyl, thiazolylcarbonyl, thiadiazolylcarbonyl, tetrazolylcarbonyl, etc. The aliphatic acyl substituted with aromatic group may include aralkanoyl such as phenyl(lower)alkanoyl, for example, phenylacetyl, phenylpropionyl, phenylhexanoyl, etc.; aralkoxycarbonyl such as phenyl(lower) alkoxycarbonyl, for example, benzyloxycarbonyl, phenylethyloxycarbonyl, etc.; aryloxyalkanoyl such as phenoxy(lower)alkanoyl for example, phenoxyacetyl, phenoxypropionyl, etc., and the like. The aliphatic acyl substituted with heterocyclic group may include heterocyclic(lower)alkanoyl such as thienylacetyl, imidazolylacetyl, pyridylacetyl, tetrazolylacetyl, thiazolylacetyl, thiadiazolylacetyl, thienylpropionyl, thiadiazolylpropionyl, tec. The above-mentioned acyl groups may have one or more substituent(s) and the preferable example of suitable substituent is as follows: (lower) alkyl such as methyl, ethyl, propyl, isopropyl, butyl, pentyl, hexyl, etc.; halogen such as chlorine, bromine, iodine, fluorine, etc.; (lower)alkoxy such as methoxy, ethoxy, propoxy, isopropoxy, butoxy, pentyloxy, hexyloxy, etc.; (lower)alkylthio such as methylthio, ethylthio, propylthio, isopropylthio, butylthio, pentylthio, hexylthio, etc.; mono-(or di- or tri-)haloalkanoyl such as chloroacetyl, bromoacetyl, dichloroacetyl, trifluoroacetyl, etc.; mono-(or di- or tri-)haloalkoxycarbonyl such as chloromethoxycarbonyl, dichloromethoxycarbonyl, 2,2,2-trichloro-ethoxycarbonyl, etc.; or nitro(or halo or lower alkoxy)aryl-oxycarbonyl such as nitrobenzyloxycarbonyl, chlorobenzyloxycarbonyl, methoxybenzyloxycarbonyl, etc., and the like. More preferable example of imino-protecting groups as defined above may be $(C_2-C_4)$alkenyloxycarbonyl or phenyl$(C_1-C_4)$alkoxycarbonyl which may have nitro substituent, and the most preferable one may be allyloxycarbonyl or 4-nitrobenzyloxycarbonyl.

Suitable "lower alkylene" may include, for example, methylene, ethylene, trimethylene, tetramethylene, pentamethylene, hexamethylene, methylmethylene, ethylethylene, propylene, etc., in which more preferable example may be $C_1-C_4$ alkylene and the most preferable one may be methylene.

In the definitions of $R_5$ and $R_6$ above,

denotes a 3- to 6-membered heterocyclic group which may contain additional hetero atoms, preferably nitrogen atom, such as substituted or unsubstituted aziridinyl, azetidinyl, pyrrolidinyl, piperidinyl or piperazinyl, in which the preferable substituent may be carbamoyl, (lower)alkyl, hydroxy (lower)alkyl, cyano(lower)alkyl, amino(lower)alkyl, carbamoyloxy(lower)alkyl or amino.

"Substituted or unsubstituted heterocyclic amine" suitable for $R_4$ preferably means a N-containing heterocyclic group, particularly aziridinyl, azetidinyl, pyrrolidinyl, piperidinyl or piperazinyl, which may be unsubstituted or substituted with carbamoyl, (lower)alkyl, hydroxy(lower)alkyl, cyano (lower)alkyl, amino(lower)alkyl, carbamoyloxy(lower) alkyl, ureido(lower)alkyl, carbamoyl(lower)alkyl, or mono or di-(lower)alkylcarbamoyl(lower)alkyl.

Among 2-(2-substituted pyrrolidin-4-yl)thio-carbapenem compounds of formula (I) according to the present invention, the preferable one is the compounds wherein $R_1$ represents hydrogen or lower alkyl, $R_2$ represents hydrogen or anion, $R_3$ represents hydrogen or straight or branched ($C_1$–$C_6$)alkanimidoyl, Z represents

or $R_9$, $R_4$ represents

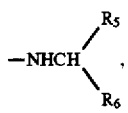

wherein $R_5$ and $R_6$ independently of one another represent hydrogen, hydroxy, hydroxy(lower)alkyl, CN, carbamoyl (lower)alkyl, cyano(lower)alkyl, carbamoyloxy(lower) alkyl, ureido(lower)alkyl or substituted or unsubstituted piperazinyl provided that $R_5$ and $R_6$ cannot be hydrogen at the same time, $R_9$ represents hydroxy($C_1$–$C_6$)alkyl or carbamoyloxy and m is an integer of 1 to 4.

Particularly preferable compounds of formula (I) according to the present invention are the compounds wherein $R_1$ represents methyl, $R_2$ represents hydrogen, $R_3$ represents hydrogen or acetimidoyl, Z represents

or $R_9$, $R_4$ represents

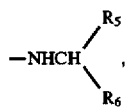

wherein $R_5$ and $R_6$ independently of one another represent hydrogen, hydroxy, hydroxy($C_1$–$C_4$)alkyl, cyano, cyano ($C_1$–$C_4$)alkyl, carbamoyloxy($C_1$–$C_4$)alkyl, ureido($C_1$–$C_4$) alkyl, or piperazinyl optionally mono-substituted with substituent selected from carbamoyl, ($C_1$–$C_4$)alkyl, hydroxy ($C_1$–$C_4$)alkyl, cyano($C_1$–$C_4$)alkyl, amino($C_1$–$C_4$)alkyl, carbamoyloxy($C_1$–$C_4$)alkyl, ureido($C_1$–$C_4$)alkyl, carbamoyl ($C_1$–$C_4$)alkyl and mono- or di-($C_1$–$C_4$)alkylcarbamoyl ($C_1$–$C_4$)alkyl, provided that $R_5$ and $R_6$ cannot be hydrogen at the same time, $R_9$ represents hydroxy($C_1$–$C_4$)alkyl or carbamoyloxy and m is an integer of 1 to 2.

The following example can be mentioned as the most preferable compound of formula (I) according to the present invention:

(1R,5S,6S)-2-[(2S,4S)-2-{(cyanomethylcarbamoyl) methylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(cyanomethylcarbamoyl) ethylmercaptomethyl}pyrrolidin-4-yl]thio-6-[(R)-1-hydroxyethyl]-1-methyl-1-carbapen-2-em-3 carboxylic acid, (1R,5S,6S)-2[(2S,4S)- 2{-(aminoethylcarbamoyl) ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(carbamoylmethylcarbamoyl) ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(hydroxyethylcarbamoyl) methylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(carbamoylmethylcarbamoyl) methylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(cyanoethylcarbamoyl) ethylmercaptomethyl}pyrrolidin-4-yl]thio-6-[(R)-1-hydroxyethyl]-1-methyl-1-carbapen-2-em-3-carboxylic acid, (1R, 5S,6S)-2-[(2S,4S)-2-{(hydroxyethylcarbamoyl) ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(carbamoylethylcarbamoyl) ethylmercaptomethyl}pyrrolidin-4-yl]thio-6-[(R)-1-hydroxyethyl-1-methyl-1-carbapen-2-em-3-carboxylic acid, (1R,5S,6S)-2-[(2S,4S)-1-acetimidoyl-2-{(2-carbamoylethylcarbamoyl) methylmercaptomethyl}pyrrolidin-4-yl]thio-6-(R)-1-hydroxyethyl]-1-methyl-1-carbapen-2-em-3-carboxylic acid, (1R,5S,6S)-2-[(2S,4S)-1-acetimidoyl-2-{(2-carbamoylmethylcarbamoyl) ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(1,2-dihydroxyethylcarbamoyl) methylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(1-hydroxy-2-cyanoethylcarbamoyl) methylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(1-hydroxy-2-aminoethylcarbamoyl) methylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(1-hydroxy-2-carbamoylethylcarbamoyl) methylmercaptomethyl}pyrrolidin-4-yl]thio-6-1[(R)-1-hydroxyethyl]-1methyl-1-carbapen-2-em-3-carboxylic acid, (1R,5S,6S)-2-[(2S,4S)-2-{(1 2-dihydroxyethylcarbamoyl) ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(1-hydroxy-2-cyanoethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(1-hydroxy-2-carbamoylethylcarbamoyl) ethylmercaptomethyl}pyrrolidin-4-yl]thio-6-[(R) 1-hydroxyethyl]-1-methyl-1-carbapen-2-em-3-carboxylic acid, (1R,5S,6S)-2-[(2S,4S)-2-{(1-(hydroxymethyl)-2-hydroxyethylcarbamoyl) methylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(1-(hydroxymethyl)-2-carbamoylethylcarbamoyl)

methylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(1-(hydroxymethyl)-2-carbamoylethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(1-(carbamoylmethyl)-2-ureidoethylcarbamoyl)methylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(1-(carbamoylmethyl)-2-cyanoethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(1-(carbamoylmethyl)-2-aminoethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(2-ureidoethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(N-methylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2{-(N,N-dimethylcarbamoyl)methylmercaptomethyl}pyrrolidin-4-yl]thio-6-[(R)-1-hydroxyethyl]- 1-methyl-1-carbapen-2-em-3-carboxylic acid, (1R,5S,6S)-2-[(2S,4S)-2-{(1-acetimidoyl-2-(carbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{1-acetimidoyl-2-(N-methylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(N-(2-hydroxyethyl)-piperazinylcarbonyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(N-(2-carbamoyloxyethyl)-piperazinylcarbonyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-(2S,4S)-2-{(N-(2-aminoethyl)-piperazinylcarbonyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(2-hydroxyethyl)mercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{(3-hydroxypropyl)mercaptomethyl}-pyrrolidin-4-yl]thio-6-[(R)-1-hydroxyethyl]-1-methyl-1-carbapen-2-em-3-carboxylic acid, (1R,5S,6S)-2-[(2S,4S)-2-{(3-(carbamoyloxy)propyl)mercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{2-(hydroxyethylpiperidinylcarbonylmethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{2-(aminoethylpiperidinylcarbonylmethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{2-(methoxyethylpiperidinylcarbonylmethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{2-(carbamoyloxyethylpiperidinylmethylcarbamoyl)ethylmercaptomethyl}pyrrolidin-4-yl]thio-6-[(R)-1-hydroxyethyl]-1methyl-1-carbapen-2-em-3-carboxylic acid, (1R,5S,6S)-2-[(2S,4S)-2-{2-(ureidoethylpiperidinylmethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{2-(methoxymethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{2-(carbamoyloxymethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{2-(ureidomethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{2-(methoxymethyloxymethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{2-(aminomethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{2-(cyanoethylpiperidinylcarbonylmethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-2-{2-(methylcarbamoyloxymethylcarbamoyl)ethylmercaptomethyl}pyrrolidin-4-yl]thio-6-[(R)-1-hydroxyethyl]-1-methyl-1-1-carbapen-2-em-3-carboxylic acid, (1R,5S,6S)-2-[(2S,4S)-2-{2-(methoxymethyloxyethylcarbamoyl)ethylmercaptomethyl}pyrrolidin-4-yl]thio-6-[(R)-1-hydroxyethyl]-1-methyl-1-carbapen-2-em-3-carboxylic acid, (1R,5S,6S)-2-[(2S,4S)-1-formimidoyl-2-{(hydroxyethylcarbonyl)methylmercaptomethyl}pyrrolidin-4-yl]thio-6-[(R)-1-hydroxyethyl]-1-methyl-1-carbapen-2-em-3-carboxylic acid, and (1R, 5S, 6S)-2-[(2S,4S)-2-{(carbamoylethyl)mercaptomethyl}pyrrolidin-4-yl]thio-6-[(R)-1-hydroxyethyl]-1-methyl-1-carbapen-2-em-3-carboxylic acid, The novel desired compound of formula (I) according to the present invention can be prepared by the processes as illustrated by Processes 1 to 4 above. The processes are explained in detail in the following.

(1) Process 1:

In Process 1 of the method according to the present invention, a carbapenem derivative of formula (II) or a reactive derivative at the oxo group thereof or a salt thereof is reacted with a mercaptopyrrolidine derivative of formula (III) or a salt thereof to prepare a compound of formula (IV) or a salt thereof. In this reaction, the carbapenem derivative of formula (II) can be preferably converted into a reactive derivative of formula (II-a) which is then reacted with the mercaptopyrrolidine derivative of formula (III). Such reactive derivative can be prepared by reacting the compound of formula (II) with an acylating agent as illustrated in the following reaction scheme:

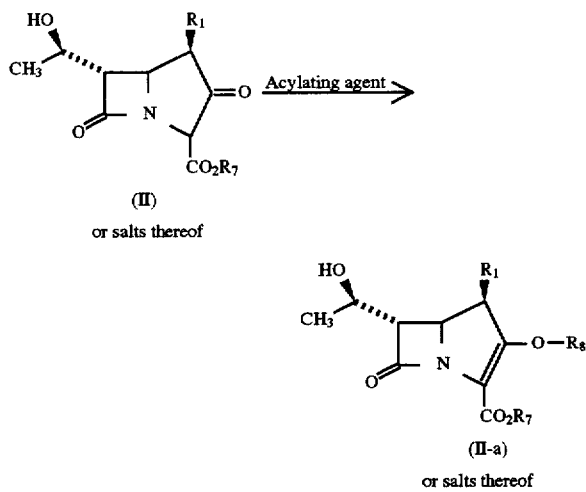

In the above reaction scheme, $R_1$ and $R_7$ are as defined above, $R_8$ represents acyl group-as exemplified for the imino-protecting group $R_{10}$ or 0,0-substituted phosphono group derived from, for example, organic phosphoric acid as mentioned below.

Suitable acylating agent which can be used in the above reaction may include conventional ones which can introduce the acyl group as mentioned above into the compound (II). Preferable acylating agents may be organic sulfonic acid, organic phosphoric acid, or its reactive derivative such as acid halide or acid anhydride, for example, arenesulfonyl halide such as benzenesulfonyl chloride, p-toluenesulfonyl chloride, p-nitrobenzenesulfonyl chloride, p-bromobenzenesulfonyl chloride, etc.; arenesulfonic anhydride such as benzenesulfonic anhydride, p-toluenesulfonic anhydride, p-nitrobenzenesulfonic anhydride, etc.; optionally halogen-substituted(lower)alkanesulfonyl halide such as methanesulfonyl chloride, ethanesulfonyl chloride, trifluoromethane sulfonyl chloride, etc.; optionally halogen-substituted (lower)alkanesulfonic anhydride such as methanesulfonic anhydride, ethanesulfonic anhydride, trifluoromethanesulfonic anhydride, etc.; di(lower)alkyl phosphorohaloridate such as diethyl phosphorochloridate, etc.; diaryl phosphorohaloridate such as diphenyl phosphorochloridate, etc., and the like, with diphenyl phosphorochloridate being most preferable.

This acylation reaction for converting the compound of formula (II) into the reactive derivative of formula (II-a) is preferably carried out in the presence of a solvent. For this purpose, any conventional organic solvent which does not adversely influence the reaction, for example, acetone, dioxane, acetonitrile, chloroform, dichloromethane, benzene, toluene, hexamethylphosphoramide, dichloroethane, tetrahydrofuran, ethyl acetate, dimethylsulfoxide, N,N-dimethylformamide, pyridine, etc., can be used. Particularly, the most preferable solvent may be acetonitrile or benzene.

When the acylating agent is used in the form of a free acid or its salt in this acylation reaction, the reaction is usually carried out in the presence of a condensing agent. Suitable condensing agent or this purpose may include, for example, carbodiimide compounds such as N,N-diethylcarbodiimide, N,N-diisopropylcarbodiimide, N,N-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, etc.; imidazole compounds such as N,N'-carbonyldiimidazole, N,N'-carbonylbis(2-methylimidazole), etc.; keteneimine compounds such as pentamethyleneketene-N-cyclohexylimine, diphenylketene-N-cyclohexylimine, etc.; 1-alkoxy-1-chloroethylene; ethoxyacetylene; ethyl polyphosphate; isopropyl polyphosphate; phosphorus oxychloride; phosphorus trichloride; thienyl chloride; oxalyl chloride; a combination of triphenylphosphine with carbon tetrachloride or diazenedicarboxylate; 2-ethyl-7-hydroxybenzeneisoxazolium salt, and the like, with N,N'-carbonyldiimidazole being most preferable. In addition, this acylation reaction may be practiced in the presence of an inorganic or organic base. Suitable bases for this purpose may include hydroxides, carbonates, bicarbonates or alkanoates of an alkali metal such as lithium, sodium, potassium, etc., and an alkaline earth metal such as calcium, magnesium, etc., for example, sodium hydroxide, potassium hydroxide, sodium carbonate, potassium carbonate, sodium bicarbonate, potassium bicarbonate, sodium acetate, magnesium carbonate or calcium carbonate; or tri(lower)alkyl amine such as triethylamine, trimethylamine, N,N-diisopropyl-N-ethylamine, etc.; pyridine compounds such as pyridine, picoline, lutidine, etc.; N,N-di(lower)alkylaminopyridine; N-(lower)alkylmorpholine; N,N-di(lower)alkylbenzeneamine, and the like. The most preferable base is N,N-diisopropylethylamine or triethylamine.

The acylation reaction is generally carried out under cooling to warming, for example, at the temperature of –40° C. to 50° C., preferably at the temperature of –20° C. to 20° C. The reaction time is generally in the range of 0.5 to 3 hours, preferably in the range of 1 to 2 hours. In this acylation reaction, 1 to 3 moles, preferably 1 to 1.5 moles, of the base and 1 to 3 moles, preferably 1 to 1.5 moles of the acylating agent are generally used with respect to one mole of the compound of formula (II).

With regard to the compound (II), it is well known that the 3,7-dioxo-1-azabicyclo[3.2.0]heptane ring system of the following formula (II-b) lies in tautomeric relation with the 3-hydroxy-7-oxo-1-azabicyclo[3.2.0]hept-2-one ring system of the following formula (II-c). Accordingly, it should be understood that both of these ring systems are substantially the same.

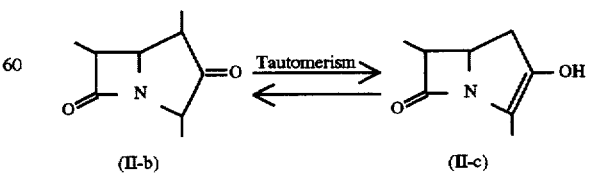

The compound of formula (II) or the compound of formula (II-a) or salts thereof can be subsequently reacted with the compound of formula (III) or salts thereof to prepare the intermediate compound of formula (IV) or salts thereof. In this reaction, the compound of formula (II-a) produced by the above acylation reaction can be used with or preferably without isolation. The reaction of the compound (II) or (II-a) or salts thereof with the compound (III) or salts thereof can be carried out in a reaction-inert solvent which does not adversely influence the reaction. As an example of such solvent, those solvent given in the explanation of the acylation reaction may be mentioned. The most preferable one may be acetonitrile or benzene. The reaction temperature can be varied within a substantially wide range. Generally, the reaction is carried out under cooling to warming.

(2) Process 2:

In Process 2, the compound (IV) or salts thereof subjected to elimination reaction of the carboxy-protecting group $R_7$ to prepare the compound (I-a) or salts thereof. The present reaction for removing the carboxy-protecting group is usually carried out by means of a conventional method such as hydrolysis, reduction, and the like.

(i) Hydrolysis

Hydrolysis for removing the carboxy-protecting group is preferably carried out in the presence of an acid or a base.

Suitable acid which can be used in such acid hydrolysis reaction may include an organic acid such as formic acid, acetic acid, propionic acid, trifluoroacetic acid, benzenesulfonic acid, p-toluenesulfonic acid, etc.; and an inorganic acid such as hydrochloric acid, hydrobromic acid, sulfuric acid, phosphoric acid, etc. When the acidic hydrolysis is carried out using trifluoroacetic acid, the reaction can be accelerated by addition of a cation-trapping agent such as phenol, anisol, etc.

Suitable base for the basic hydrolysis may include an alkali metal hydroxide such as sodium hydroxide, potassium hydroxide, etc.; an alkaline earth metal hydroxide such as magnesium hydroxide, calcium hydroxide, etc.; an alkaline earth metal hydride such as calcium hydride, etc.; an alkali metal hydride such as sodium hydride, etc; an alkali metal alkoxide such as sodium methoxide, sodium ethoxide, potassium t-butoxide, etc.; an alkali metal carbonate such as sodium carbonate, potassium carbonate, etc.; or an alkali metal bicarbonate such as sodium bicarbonate, potassium bicarbonate, etc., and the like.

This hydrolysis reaction is usually carried out in the presence of a solvent which does not adversely influence the reaction such as water, alcohol, for example, methanol, ethanol, etc., tetrahydrofuran, and the like, in which the preferable one may be methanol. When the acid or base used in the hydrolysis is a liquid form, it can be also used as the solvent.

(ii) Reduction

The reduction method which can be used for elimination reaction of the carboxy-protecting group may include reduction by using a combination of a metal such as zinc or zinc amalgam or a salt of chrome compound such as chromous chloride or chromous acetate and an organic or inorganic acid such as acetic acid, propionic acid, hydrochloric acid, sulfuric acid, etc.; and conventional: catalytic reduction in the presence of a conventional metallic catalyst such as palladium catalyst, for example, spongy palladium, palladium black, palladium oxide., palladium on carbon, palladium hydroxide on carbon, colloidal palladium, palladium on barium sulfate, palladium on barium carbonate, etc., nickel catalysts, for example, reduced nickel, nickel oxide, Raney nickel, etc., or patinum catalyst, for example, platinum plate, platinum black, platinum on carbon, colloidal platinum, platinum oxide, etc., and the like. Among those reduction methods, the catalytic reduction using palladium oxide or palladium on carbon is most preferable. In case that the catalytic reduction is applied, the reaction is preferably carried out under neutral condition.

This reduction can be conveniently carried out in a solvent which does not adversely influence the reaction. For this purpose, suitable solvent may include, for example, water, alcohol such as methanol, ethanol, propanol, etc., dioxane, tetrahydrofuran, acetic acid, phosphate buffer, and the like, or a mixture thereof, with the mixed solvent of water and ethanol or water and tetrahydrofuran being most preferable. In this reaction, the preferable reaction temperature is in the range of 0° C. to 30° C., most preferably in the range of 20° C. to 30° C., and the reaction time is generally 0.5 to 4 hours and most preferably 2 to 3 hours. The amount of catalyst used in this reduction is usually 0.01 to 1 moles, preferably 0.01 to 0.5 moles, with respect to one mole of the compound of formula (IV). Hydrogen atmosphere is used in 1 to 4 atmospheric pressure and preferably in 3 to 4 atmospheric pressure.

In case that the carboxy-protecting group is allyl group, it can be deprotected by hydrogenolysis in the presence of a palladium compound Suitable palladium compound used in this deprotecting reaction may include palladium on carbon, palladium hydroxide on carbon, palladium chloride, tetrakis (triphenylphospine)palladium (0), bis (dibenzylidenylacetone)palladium(0), di[(1,2-bis (diphenylphosphino)ethane]palladium(0), tetrakis (triphenylphosphite)palladium(0), tetrakis (triethylphosphite)palladium(0). This reaction can preferably be carried out in the presence of a scavenger of allyl group generated in situ. Suitable scavenger which can be used for this purpose may include, for example, amine such as morpholine, N-methylaniline, etc.; an activated methylene compound such as dimedone, benzoylacetate, 2-methyl-3-oxovaleric acid, etc.; a cyanohydrin compound such as α-tetrahydropyranyloxybenzylcyanide, etc.; lower alkanoic acid such as formic acid, ammonium formate, sodium acetate, etc.; N-hydroxysuccinimide, and the like. This reaction can also be carried out in the presence of a base such as lower alkylamine, for example, butylamine, triethylamine, etc., pyridine, and the like. When palladium-ligand complex is used in this reaction, the reaction can preferably be carried out in the presence of the corresponding ligand, for example, triphenylphosphine, triphenylphosphite, triethylphosphite, and the like. The reaction is usually carried out in a reaction-inert solvent such as water, methanol, ethanol, propanol, dioxane, tetrahydrofuran, acetonitrile, chloroform, dichloromethane, dichloroethane, ethylacetate, etc. The reaction temperature can be varied within a substantially wide range and the reaction is generally carried out under cooling to warming.

The elimination reaction of protecting group can be carried out using a reducing agent appropriately selected depending on the kind of carboxy-protecting group to be eliminated.

(3) Process 3:

In the reaction of Process 3, the compound of formula (I-a) or salts thereof is subjected to elimination reaction of the imino-protecting group($R_{10}$) to prepare the compound of formula (I-b.))or salts thereof. This elimination reaction of the imino-protecting group can generally be carried out by means of a conventional method such as hydrolysis, reduction and the like. The method of hydrolysis and reduction, and the reaction conditions (reaction temperature, solvent, and the like) are substantially the same as those illustrated for elimination reaction of the carboxy-protecting group in Process 2 above. If necessary, the reaction of Process 3 can be directly carried out in the same reaction vessel without isolation of the compound (I-a) produced by Process 2.

The reaction of Process 3 for removing the imino-protection group is carried out in the same manner as the reaction of Process 2 for removing the carboxy-protecting group.

21

Alternatively, Process 3 can be practiced simultaneously with Process 2 and this case is also included within the score of the present invention.

(4) Process 4:

In Process 4, the compound of formula (I-b) or salts thereof is reacted with lower alkanimidoylating agent to prepare the compound of formula (I) wherein $R_3$ is lower alkanimidoyl group, i.e. the compound of formula (I-c), or salts thereof.

In this reaction, suitable lower alkanimidoylating agent may be any of conventional ones which can introduce the lower alkanimidoyl group into the compound of formula (I-b). As a specific example of such lower alkanimidoylating agent, the following compounds can be mentioned: lower alkyl(lower)alkanimidate such as methyl formimidate, ethyl formimidate, methyl acetimidate, ethyl acetimidate, ethyl propionimidate, methyl butyrimidate, ethyl isovalerimidate, ethyl pentanimidate, ethyl hexanimidate, etc.; lower alkanimidoyl halide such as formimidoyl chloride, formimidoyl bromide, acetimidoyl chloride, acetimidoyl bromide, propionimidoyl bromide, butyrimidoyl chloride, isovalerimidoyl chloride, pentanimidoyl chloride, hexanimidoyl chloride, etc., and the like, with methyl formimidate or methyl acetimidate being most preferable.

This reaction is usually carried out in a solvent which does not adversely influence the reaction such as tetrahydrofuran, dioxane, water, methanol, ethanol, etc., or a mixture thereof. The most preferable solvent may be a mixed solvent of water and ethanol. The reaction temperature can be varied within a substantially wide range and the reaction is generally carried out under cooling to warming, most preferably at the temperature of $-10°$ C. to $10°$ C., for the reaction time of 0.5 to 3 hours, more preferably 1 to 1.5 hours.

In the present reaction, the lower alkanimidoylating agent may be used in an amount of 1 to 2 moles, preferably 1 to 1.5 moles and particularly 1.2 moles, with respect to one mole of the compound (I-b).

The reaction can also be carried out in the presence of an inorganic or organic base. Suitable base which can be used in this reaction may be those given in the explanation of the reaction of Process 1. In this reaction, the base is used in an amount sufficient to maintain the pH value of the reaction solution at the weak alkaline level, preferably in the range of pH 8 to 9 and most preferably in the range of pH 8.5 to 8.7.

The compound of formula (I) and salts thereof obtained from the Processes 1 to 4 according to the present invention can be isolated and purified by means of a conventional manner, for example, extraction, precipitation, fractional crystallization, recrystallization, column chromatography, and the like.

Suitable salts of the compounds of formulae (II), (II-a), (III), (IV), (I-a), (I-b) and (I-c), which are used as starting materials and reactants or obtained as reaction products in the Processes 1 to 4 above, may be the same as those specifically exemplified in connection with the salts of the compound of formula (I).

The mercaptopyrrolidine derivative of formula (III), which is used as a reactant in Process 1 above for preparation of the compound (I) according to the present invention, is a novel compound which was never disclosed in the prior art. Accordingly, another object of the present invention is to provide a compound of the following formula (III):

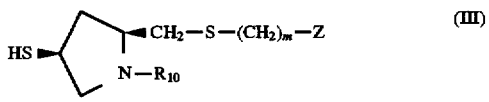

(III)

22 or salts thereof, in which $R_{10}$ represents an imino-protecting group,

Z represents

or $R_9$,

X represents O or NH, $R_4$ represents amino or heterocyclic amine group, each of which can be unsubstituted or substituted with a group of formula

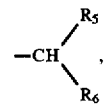

a unsubstituted or substituted heterocyclic group or a (lower)alkyl group, or represents hydroxy(lower)alkyl or carbamoyloxy(lower)alkyl, $R_5$ and $R_6$ independently of one another represent hydrogen, hydroxy, hydroxy(lower)alkyl, cyano, amino, carbamoyl, carbamoyl(lower)alkyl, cyano (lower)alkyl, mono- or di-(lower)alkylcarbamoyl, carbamoyloxy, ureido, amino(lower)alkyl, carbamoyloxy(lower)alkyl, mono- or di-(lower)alkylcarbamoyl(lower)alkyl, ureido(lower)alkyl, or a group of formula

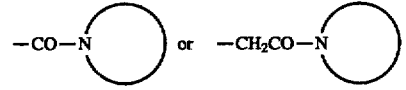

wherein

denotes a unsubstituted or substituted 3- to 6-membered heterocyclic group which can contain additional hetero atoms, provided that $R_5$ and $R_6$ cannot be hydrogen at the same time, $R_9$ represents hydroxy(lower)alkyl or carbamoyloxy, and m is an integer of 1 to 6, provided that when m is 1 and X is O, $R_4$ is other than unsubstituted amino(—$NH_2$)

Further, the present invention provides a process for preparation of the compound of formula (III) and salts thereof. The process for preparation of the compound (III) according to the present invention can be represented by Methods A and B as depicted below.

Method A

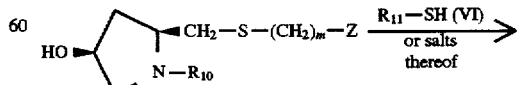

or a reactive derivative
at the hydroxy group thereof
or salts thereof

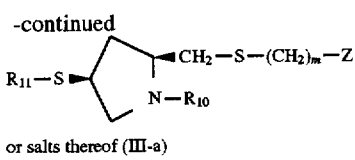

or salts thereof (III-a)

Method B

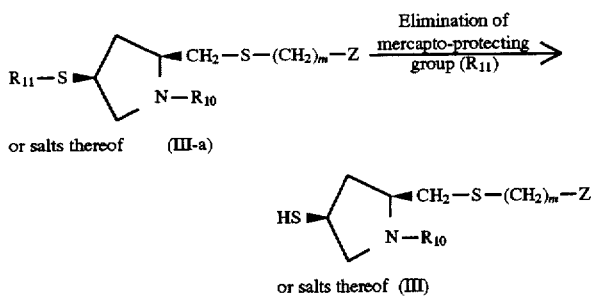

In the above reaction scheme, $R_{11}$ represents a mercapto-protecting group, and $R_{10}$, Z and m are as defined above.

Suitable "mercapto-protecting group" for $R_{11}$ may include acyl group as mentioned above in connection with the imino-protecting group; ar(lower)alkyl group such as mono- or di- or tri-phenyl(lower)alkyl, for example, benzyl, phenethyl, benzhydryl, trityl, etc.; and the like, in which more preferable example may be $C_1$–$C_4$ alkanoyl, aroyl and triphenyl($C_1$–$C_4$)alkyl and the most preferable mercapto-protecting group may be acetyl.

Methods A and B for preparing the novel compound of formula (III) and salts thereof are explained in detail in the following.

a) Method A:

In Method A, the compound of formula (V) or a reactive derivative at the hydroxy group thereof or salts thereof can be reacted with the mercaptan derivative of formula (VI) or salts thereof to prepare the derivative of formula (III-a) or salts thereof.

Suitable reactive derivative at the hydroxy group of the compound of formula (V) may include a conventional one such as halides, for example, chloride, bromide, iodide, etc.; sulfonates, for example, methanesulfonate, benzenesulfonate, toluenesulfonate, etc.; and the like, with a sulfonate compound, particularly methanesulfonate being most preferable. In case that the compound of formula (V) is a methanesulfonate derivative, the reaction of Method A can be carried out, for example, by reacting one equivalent weight of the compound of formula (VI) with 1 to 2 equivalent weight, preferably 1.2 equivalent weight, of the methanesulfonate compound of formula (V) and 1 to 2 equivalent weight, preferably 1.2 equivalent weight, of an organic or inorganic base in a halogenated alkane solvent such as dichloromethane, at the temperature of $-10°$ C. to $40°$ C., more preferably $-5°$ C. to $0°$ C., or 1 to 3 hours, more preferably 1 to 1.5 hours.

Preferable example of the mercaptan derivative of formula (VI) used as a reactant in the reaction of Method A may be ar(lower)alkanethiol such as mono- or di- or tri-phenyl (lower)alkanethiol, for example, phenylmethanethiol, diphenylmethanethiol, triphenylmethanethiol, etc.; thio (lower)alkanoic-S-acid such as thioacetic-S-acid, etc.; thioarenoic-S-acid such as thiobenzoic-S-acid, etc.; and the like, in which more preferable example may be triphenyl ($C_1$–$C_4$)alkanethiol, thio($C_1$–$C_4$)alkanoic-S-acid and thio ($C_6$–$C_{10}$)arenoic-S-acid, and salts thereof. The most preferable mercaptan derivative(VI) may be thioacetic-S-acid or its potassium salt. In case that the compound(VI) is thioacetic-S-acid potassium salt, the reaction of Method A can be carried out in a stoichiometric manner, for example, by reacting one equivalent weight of the compound (V) with 1 to 2 equivalent weight, preferably 1.5 equivalent weight, of potassium thioacetate(VI) in a solvent such as dimethylsulfoxide, hexamethylphosphoramide or N,N-dimethylformamide, preferably in N,N-dimethylformamide, at the temperature in the range of $60°$ C. to $100°$ C., more preferably $80°$ C. to $90°$ C., for 2 to 5 hours, more preferably 2.5 to 3 hours.

In Method A, when the compound of formula (VI) is ar(lower)alkanethiol, the compound of formula (V) is preferably used in the form of its reactive derivative at the hydroxy group and the reaction can be conveniently carried out in the presence of an inorganic or organic base. Suitable inorganic or organic base used in this reaction may be those exemplified in Process 1 above.

In case that the compound (VI) is thio(lower)alkanoic-S-acid or thioarenoic-S-acid, the reaction of Method A is preferably carried out in the presence of a conventional condensing agent such as a combination of triarylphosphine, for example, triphenylphosphine, etc., and di(lower) alkylazodicarboxylate, for example, diethylazodicarboxylate, etc. This reaction is usually carried out in a conventional solvent which does not adversely influence the reaction, such as dichloromethane, methanol, ethanol, propanol, pyridine, N,N-dimethylformamide or tetrahydrofuran, with tetrahydrofuran being most preferable. In such a case, the reaction of Method A is preferably carried out, for example by reacting one equivalent weight of the compound of formula (V) with 1 to 2 equivalent weight, preferably 1.5 equivalent weight, of thio(lower)alkanoic-S-acid such as thioacetic acid, 1 to 2 equivalent weight, preferably 1.5 equivalent weight, of diethylazodicarboxylate and 1 to 5 equivalent weight, preferably 2 equivalent weight, of triphenylphosphine in tetrahydrofuran solvent at the temperature of $-40°$ C. to $10°$ C., preferably $0°$ C. to $5°$ C., for 2 to 5 hours, preferably 2 to 3 hours.

As a result of the reaction of Method A, the configuration on the carbon atom substituted with the hydroxy group of the compound (V) is inverted in the resulting compound (III-a)

b) Method B:

In Method B, the compound of formula (III-a) or salts thereof obtained from Method A is subjected to elimination reaction of the mercapto-protecting group to prepare the compound of formula (III) or salts thereof.

The elimination reaction of the mercapto-protecting group according to Method B is carried out by means of a conventional method as described below and can be appropriately selected depending on the kind of the mercapto-protecting group to be eliminated. For example, when the protecting group is ar(lower)alkyl group, this protecting group can generally be eliminated by treating with a silver compound such as silver nitrate, silver carbonate, etc. This elimination reaction with silver compound is preferably carried out in the presence of an organic base such as pyridine, etc. The resulting silver salt of the compound of formula (II:) can be converted into its alkali metal salt, if necessary, by treating with alkali metal halide such as sodium iodide, potassium iodide, etc.

Further in case that the mercapto-protecting group is acyl, this protecting group can generally be eliminated by solvolysis such as alcoholysis or hydrolysis using acid or base. Suitable acid and base which can be used in this reaction may be those exemplified in connection with hydrolysis in Process 2 above, in which sodium methoxide and sodium hydroxide is most preferable. This hydrolysis is usually carried out in a conventional solvent which does not adversely influence the reaction such as alcohol, for example, methanol, ethanol, etc., water, pyridine, N,N-dimethylformamide, etc., or a mixture thereof, in which the most preferable one is methanol or water.

In case that the reaction of Method B is carried out by basic hydrolysis, the reaction is carried out, for example, by using 1 to 2 moles, preferably 1 to 1.5 moles, of a base with respect to one mole of the compound of formula (III-a) in the presence of a solvent such as water, alcohol or tetrahydrofuran, most preferably in methanol solvent, at the temperature of −20° C. to 50° C., most preferably −10° C. to 10° C., for 0.5 to 2 hours, most preferably 0.5 to 1 hour. The reaction is practiced substantially in a stoichiometric manner.

The compound of formula (III) obtained from Methods A and B above can be isolated and purified according to a conventional method, for example, by extraction, precipitation, fractional crystallization, recrystallization, chromatography, and the like.

The novel carbapenem derivative of formula (I) and pharmaceutically acceptable salts thereof according to the present invention exhibit a potent antibacterial activity against various gram-positive and gram-negative bacterial strains and, therefore, has a clinical utility for prophylaxis and treatment of various bacterial infectious diseases. Antibacterial activity of the desired compound (I) of the present invention is demonstrated by the following experiments including in vitro antibacterial activity test.

Test Examples
Test 1: In Vitro Antibacterial Activity Test

The antibacterial activity of the compound (I) of the present invention was determined by measuring the minimal inhibitory concentration(MIC) according to the antibacterial activity test method as described below. The compounds of Examples 1,2,3 and 4 according to the present invention were used as a test compound and imipenem was used as a comparative compound.

The test compounds and comparative compound were gradually diluted in Mueller Hinton Agar(MHA) medium. Test strains as listed in the following table were inoculated into the medium in an amount of $10^6$ viable cells/ml and then incubated at 37° C. for 18 hours. Then, MIC value was measured and expressed in terms of μg/ml. The results are shown in the following Table 1.

TABLE 1

Minimal Inhibitory Concentration of the compound (I) and imipenem

| Test strains | Imipenem | MICs Minimal Inhibitory Concentration (μg/ml) Test compound | | | |
|---|---|---|---|---|---|
| | | Example 1 | Example 2 | Example 3 | Example 4 |
| Staphylococcus aureus SG 511 | 0.10 | 0.05 | 0.05 | 0.05 | 0.05 |
| Escherichia coli DC 2 | 0.78 | 0.10 | 0.10 | 0.10 | 0.10 |
| Escherichia coli TEM | 0.20 | 0.10 | 0.05 | 0.05 | 0.10 |
| Pseudomonas aeruginosa 9027 | 0.78 | 0.10 | 0.78 | 0.39 | 0.10 |
| Pseudomonas aeruginosa | 0.78 | 0.78 | 0.78 | 0.39 | 0.78 |
| 1592E Salmonella typhimurium | 0.78 | 0.20 | 0.10 | 0.10 | 0.20 |
| Klebsiella aerogenes 1522E | 0.78 | 0.20 | 0.10 | 0.10 | 0.10 |
| Klebsiella oxytoca 1082E | 0.39 | 0.20 | 0.20 | 0.20 | 0.20 |
| Enterobacter cloacae 1321E | 0.20 | 0.05 | 0.05 | 0.05 | 0.05 |

From the result given in Table 1 above, it can be seen that the compound of formula (I) and pharmaceutically acceptable salts thereof according to the present invention exhibit a considerably superior antibacterial activity in comparison with the known compound in the prior art, imipenem.

Test 2: Stability Test Against kidney Dehydrogenase DHP-I

Each of the novel compounds of Examples 1,2,3 and 4 of the present invention and the comparative compound imipenem was dissolved in 10 mM phosphate buffer and the resulting solution was mixed with dehydrogenase enzyme solution extracted from pig kidney in a ratio of equivalent amounts. The resulting mixture was incubated at 37° C. for 2 hours, during which the decomposition degree of the compound was measured. The result thereof was given in the following Table 2 in terms of percentage of the remaining amount on the basis of the initially added amount of the compound.

TABLE 2

Stability of the compounds (I) and imipenem on DHP-I enzyme

| | Time (minute) | | | | | (Unit: %) |
|---|---|---|---|---|---|---|
| Test Compound | 5 | 10 | 20 | 40 | 80 | 120 |
| Imipenem | 99.2 | 97.9 | 94.3 | 87.7 | 77.0 | 66.6 |
| Compound of Example 1 | 99.7 | 99.4 | 99.1 | 98.1 | 97.5 | 97.2 |
| Compound of Example 2 | 100 | 99.4 | 98.6 | 97.2 | 96.3 | 96.3 |
| Compound of Example 3 | 99.7 | 99.2 | 98.9 | 98.0 | 97.2 | 97.0 |
| Compound of Example 4 | 100 | 99.8 | 99.0 | 99.8 | 98.8 | 98.8 |

From the result given in Table 2 above, it can be seen that the known compound in prior art, imipenem, was composed by about 40% within about 2 hours from the beginning of mixing incubation, while the novel compound of formula (I) of the present invention was substantially never decomposed and shows a high stability. Such test result demonstrates that imipenem has a disadvantage in that it should be administered together with an enzyme inhibitor such as Cilastatin, whereas the compound of the present invention shows stably a high antibacterial activity even when it is administered alone.

As can be demonstrated by the results of Tests 1 and 2 above, the carbapenem derivative of formula (I) and pharmaceutically acceptable salts thereof according to the present invention are clinically used for the purpose of prophylaxis and treatment of infectious diseases. For this

27 purpose, the compound of formula (I) and pharmaceutically acceptable salts thereof can be formulated into a pharmaceutically acceptable preparation suitable for administration, together with pharmaceutically acceptable carriers such as solid or liquid excipients. Such pharmaceutical preparation may be in solid or liquid form, for example, tablet, capsule, granule, powder, pill, solution, suspension, syrup, emulsion, and the like. If necessary, the pharmaceutical preparation can additionally contain conventional additives, for example, formulating aid, stabilizer, wetting agent, thickening agent, disintegrator, perfume, pigment, binder, and the like.

The dosage of the compound of formula (I) and pharmaceutically acceptable salts thereof according to the present invention may vary depending on kind and severity of diseases to be treated, age and conditions of the patient, and kind of the compound (I) to be administered. In general, an amount of 100 to 500 mg per day may be administered per one adult patient as a single dose or a multiple-divided dose.

The present invention will be explained by the following Examples and Reference Examples in more detail. However, it should be understood that the present invention is not limited by these examples in any manner.

EXAMPLE 1

Preparation of (1R,5S,6S)-2-[(2S,4S)-2-{(cyanomethylcarbamoyl)methylmercaptomethyl}pyrrolidin-4-yl]thio-6-[(R)-1-hydroxyethyl]-1-methyl-1-carbapen-2-em-3-carboxylic acid (1) 580 mg of 4-nitrobenzyl-2-diphenoxyphosphoryloxy-6-[(R)-1-hydroxyethyl]-1-methyl-1-carbapen-2-em-3-carboxylate and 380 mg of (2S,4S)-1-(p-nitrobenzyloxycarbonyl)-2-{(cyanomethylcarbamoyl)methylmercaptomethyl}-4-mercaptopyrrolidine were dissolved in 25 ml of acetonitrile. To the resulting solution was added dropwise 0.25 ml of N,N-diisopropylethylamine under nitrogen atmosphere at −10° C. to −5° C. and then the reaction mixture was stirred overnight at 5° C. The reaction solution was concentrated under reduced pressure. 20 ml of 5% sodium bicarbonate solution was added to the residue and the mixture was extracted with 30 ml of ethylacetate. The extract was dried over magnesium sulfate and concentrated under reduced pressure. The residue was subjected to column chromatography(eluent: EtOAc:acetone=3:2 v/v) to obtain 760 mg of 4-nitrobenzyl (1R,5S,6S)-2-[(2S,4S)-1-(p-nitrobenzyloxycarbonyl)-2-{(cyanomethylcarbamoyl)methylmercaptomethyl }pyrrolidin-4-yl]thio-6-[(R)-1-hydroxyethyl]-1-methyl-1-carbapen-2-em-3-carboxylate.

IR(Nujol)cm$^{-1}$: 1755, 1751, 1710, 1653 NMR(CDCl$_3$) δ: 1.27 (3H,d,J=8 Hz), 1.37 (3H,d,J=8 Hz), 1.78–1.90 (1H,m), 2.30–2.80 (7H,m), 3.31–3.76 (4H,m), 5.04–5.54 (6H,m), 7.44–7.50 (2H, dd, J=18 Hz), 7.55–7.65 (4H, d, J=9 Hz), 8.17–8.25 (6H,m)

(2) 690 mg of the compound obtained in the above (1) was dissolved in 10 ml of tetrahydrofuran. To the resulting solution were added 18 ml of 0.1M 4-morpholinopropane sulfonate solution (pH=7.0), 1.8 ml of ethanol and 0.3 g of 10% palladium on carbon and then the mixture was hydrogenated under pressure. After the reaction time of 4 hours, the catalyst was filtered off and the filtrate was washed with 20 ml of dichloromethane. The aqueous layer was separated and purified with polymer chromatography(CHP-20, eluent: 5% THF-H$_2$O ). Then, the eluate was lyophilized to obtain 170 mg of the title compound.

Melting Point: 173°–174.5° C. (dec.) IR(KBr)cm$^{-1}$: 1750, 1580, 1390 NMR(D$_2$O) δ: 1.20 (3H,d,J=8 Hz), 1.28 (3H,d,, J=8 Hz), 1.40–2.10 (2H,m), 2.55–3.95 (6H,m)

28

EXAMPLE 2

Preparation of (1R,5S,6S)-2-[(2S,4S)-2-{(cyanomethylcarbamoyl)ethylmercaptomethyl}pyrrolidin-4-yl]thio-6-[(R)-1-hydroxyethyl]1-methyl-1-carbapen-2-em-3-carboxylic acid (1) The reaction was carried out in the same manner as that of Example 1-(1), starting from 480 mg of 4-nitrobenzyl-2-diphenoxyphosphoryloxy-6-[(R)-1-hydroxyethyl]-1-methyl-1-carbapen-2-em-3-carboxylate and 320 mg of (2S,4S)-[1-(p-nitrobenzyloxycarbonyl)-2-{(cyanomethylcarbamoyl)ethylmercaptomethyl}-4-mercapto]pyrrolidine to obtain 580 mg of 4-nitrobenzyl (1R,5S,6S)-2-[(2S,4S)-1-(p-nitrobenzyloxycarbonyl)-2-{(cyanomethylcarbamoyl)ethylmercaptomethyl}pyrrolidin-4-yl]thio-6-[(R)-1-hydroxyethyl]-1-methyl-1-carbapen-2-em-3-carboxylate.

IR(Nujol)cm$^{-1}$: 1780, 1750, 1620 NMR(D$_2$O) δ: 1.21 (3H,d,J=3 Hz), 1.30 (3H,d,J=8 Hz), 3.02–385 (12H,m), 4.80 (2H, br. s), 5.25 (2H,s), 5.38 (2H, dd, J=18 Hz), 7.58 (2H, d, J=8 Hz), 8.26 (6H,m)

(2) The compound obtained in the above (1) was hydrogenated in the same manner as that of Example 1-(2) to obtain 120 mg of the title compound.

Melting Point: 175°–175.5° C. (dec.) IR(KBr)cm$^{-1}$: 1750, 1580 NMR(D$_2$O) δ: 1.23 (3H,d,J=7.9 Hz), 1.30 (3H,d,J=6.8 Hz), 1.81 (1H, dd, J=18 Hz, J=8.5 Hz), 2.70–3.34 (5H,m), 3.45–3.85 (3H,m), 4.25–4.27 (2H,m)

EXAMPLE 3

Preparation of (1R,5S,6S)-2-[(2S,4S)-2-{(hydroxyethylcarbamoyl)ethylmercaptomethyl}pyrrolidin-4-yl]thio-6-[(R)-1-hydroxyethyl]-1-methyl-1-carbapen-2-em-3-carboxylic acid (1) The reaction was carried out in the same manner as that of Example 1-(1), starting from 550 mg of 4-nitrobenzyl-2-diphenoxyphosphoryloxy-6-[(R)-1-hydroxyethyl]-1-methyl-1-carbapen-2-em-3-carboxylate and 410 mg of (2S,4S)-[1-(p-nitrobenzyloxycarbonyl)-2-{(hydroxyethylcarbamoyl)ethylmercaptomethyl}-4-mercapto]pyrrolidine to obtain 420 mg of 4-nitrobenzyl (1R,5S,6S)-2-[(2S,4S)-1-(p-nitrobenzyloxycarbonyl)-2-{(hydroxyethylcarbamoyl)ethylmercaptomethyl}pyrrolidin-4-yl]thio-6-[(R)-1-hydroxyethyl]-1-methyl-1-carbapen-2-em-3-carboxylate.

IR(Nujol)cm$^{-1}$: 3400, 1770–1740, 1710–1680, 1605 NMR(CDCl$_3$) δ: 1.1–1.6 (6H,m), 5.1–5.6 (4H,m), 7.3–7.7 (4H,m), 8.21 (4H, d, J=9 Hz)

(2) The compound obtained in the above (1) was hydrogenated in the same manner as the a of Example 1-(2) to obtain 250 mg or the title compound.

Melting Point: 172°–173° C. (dec.) IR(KBr)cm$^{-1}$: 1765–1725, 1590–1550 NMR(D$_2$O) δ: 1.21 (3H,d,J=8 Hz), 1.28 (3H,d,J=7 Hz), 1.52–2.0 (4H,m), 2.49–2.9 (3H,m)

EXAMPLE 4

Preparation of (1R,5S,6S)-2-[(2S,4S)-2-{(2-carbamoylmethylcarbamoyl)ethylmercaptomethyl}pyrrolidin-4-yl]thio-6-[(R)-1-hydroxyethyl]-1-methyl-1-carbapen-2-em-3-carboxylic acid (1) The reaction was carried out in the same manner as that of Example 1-(1), starting from 650 mg of 4-nitrobenzyl-2-diphenoxyphosphoryloxy-6-[(R)-1-hydroxyethyl]-1-methyl-1-carbapen-2-em-3-carboxylate and 350 mg of (2S,4S)-[1-(p-nitrobenzyloxycarbonyl)-2-{(2-carbamoylmethylcarbamoyl)ethylmercaptomethyl}-4-mercapto]pyrrolidine to obtain 450 mg of 4-nitrobenzyl (1R,5S,6S)-2-[(2S,4S)-1-(p-nitrobenzyloxycarbonyl)-2-{(2-carbamoylmethylcarbamoyl)ethylmercaptomethyl}pyrrolidin-4-yl]thio-6-[ (R)-1-hydroxyethyl]-1-methyl-1-carbapen-2-em-3-carboxylate.

IR(Nujol)cm$^{-1}$: 1770, 1705, 1610, 1525 NMR(CDCl$_3$) δ: 1.25 (3H,d,J=7.5 Hz), 1.32 (3H,d,J=6 Hz) 3.10–4.83 (3H, m), 4.81 (2m, br. s), 5.24 (2H,s), 5.38 (2H, dd, J=18 Hz), 7.56–7.63 (4H, dd, J=18 Hz), 8.24 (4H, d, J=8 Hz)

(2) The compound obtained in the above (1) was hydrogenated in the same manner as that of Example 1-(2) to obtain 120 mg of the title compound.

Melting Point 168°–172° C. (dec.) IR(KBr)cm$^{-1}$: 1755, 1680 NMR(D$_2$O) δ: 1.21 (3H,d,J=9 Hz), 1.27 (3H,d,J=6 Hz), 1.42–2.03 (2H,m), 2.53–4.36 (10H,m)

EXAMPLE 5

Preparation of (1R,5S,6S)-2-[(2S,4S)-1-acetimidoyl-2-{(2-carbamoylmethylcarbamoyl)ethylmercaptomethyl}pyrrolidin-4-yl]thio-6-[(R)-1-hydroxyethyl]-1-methyl-1-carbapen-2-em-3-carboxylic acid 120 mg of the compound obtained in Example4–(2), (1R,5S,6S)-2-[(2S,4S)-2-{(2-carbamoylmethylcarbamoyl)ethylmercaptomethyl}pyrrolidin-4-yl]thio-6-[(R)-1-hydroxyethyl]-1-methyl-1-carbapen-2-em-3-carboxylic acid was dissolved in 30 ml of distilled water. To the resulting solution was added 1.4 g of ethylacetimidate hydrochloride. Then, the reaction mixture was adjusted to pH 8.4–8.6 by adding 10% aqueous sodium carbonate solution at 0° to 4° C. When the reaction was completed, the reaction mixture was adjusted to pH 6.5 by adding 1N-aqueous hydrochloric acid solution and then washed with the mixture of 50 ml of ethyl acetate and 10 ml of tetrahydrofuran. The organic layer was removed and the aqueous layer was subjected to polymer chromatography (CHP-20, eluent: 5% acetone-H$_2$O ). The eluate was lyophilized to obtain 80 mg of the title compound.

IR(KBr)cm$^{-1}$: 1800–1720 NMR(D$_2$O) δ: 1.27 (6H, t, J=7.4 Hz), 2.30–2.80 (3H,s)

EXAMPLE 6

Preparation of (1R,5S,6S)-2-[(2S,4S)-2-{(carbamoyl-1-(hydroxy)ethylcarbamoyl)methylmercaptomethyl}pyrrolidin-4-yl]thio-6-[(R)-1-hydroxyethyl]-1-methyl-1-carbapen-2-em-3-carboxylic acid (1) The reaction was carried out in the same manner as that of Example 1-(1), starting from 580 mg of 4-nitrobenzyl-2-diphenoxyphosphoryloxy-6-[(R)-1-hydroxyethyl]-1-methyl-1-carbapen-2-em-3-carboxylate and 310 mg of (2S,4S)-[1-(p-nitrobenzyloxycarbonyl)-2-{(carbamoyl-1-(hydroxy)ethylcarbamoyl)methylmercaptomethyl}-4-mercapto]pyrrolidine to obtain 620 mg of 4-nitrobenzyl (1R,5S,6S)-2-[(2S,4S)-1-(p-nitrobenzyloxycarbonyl)-2-{(carbamoyl-1-(hydroxy)ethylcarbamoyl)methylmercaptomethyl}pyrrolidin-4-yl]thio-6-[(R)-1-hydroxyethyl]-1-methyl-1-carbapen-2-em-3-carboxylate.

IR(Neat)cm$^{-1}$: 1765, 1725–1700, 1605 NMR(CDCl$_3$) δ: 1.1–1.7 (6H,m), 5.0–5.6 (4H,m), 7.4–7.8 (4H,m), 8.21 (4H, d, J=8.5 Hz)

(2) The compound obtained in the above (1) was hydrogenated in the same manner as that of Example 1-(2) to obtain 170 mg of the title compound.

Melting Point: 176°–177.5° C. (dec.) IR(KBr)cm$^{-1}$: 1765, 1705–1675 NMR(D$_2$O) δ: 1.21 (3H,d,J=9 Hz) 1.27 (3H,d, J=6 Hz), 1.42–2.03 (2H,m), 2.53–4.36 (10H,m)

EXAMPLE 7

Preparation of (1R, 5S, 6S)-2-[(2S,4S)-2-{(hydroxy-1-(hydroxymethyl)ethylcarbamoyl)methylmercaptomethyl}pyrrolidin-4-yl]thio-6-[(R)-1-hydroxyethyl]-1-methyl-1-carbapen-2-em-3-carboxylic acid (1) The reaction was carried out in the same manner as that of Example 1-(1), starting from 720 mg of 4-nitrobenzyl-2-diphenoxyphosphoryloxy-6-[(R)-1-hydroxyethyl]-1-methyl-1-carbapen-2-em-3-carboxylate and 310 mg of (2S,4S)-[1-(p-nitrobenzyloxycarbonyl)-2-{(hydroxy-1-(hydroxymethyl)ethylcarbamoyl)methylmercaptomethyl}-4-mercapto]pyrrolidine to obtain 840 mg of 4-nitrobenzyl (1R,5S, 6S)-2-[(2S, 4S)-1-(p-nitrobenzyloxycarbonyl)-2-{(hydroxy-1-(hydroxymethyl)ethylcarbamoyl)methylmercaptomethyl}pyrrolidin-4-yl]thio-6-[(R)-1-hydroxyethyl]-1-methyl-1-carbapen-2-em-3-carboxylate.

IR(Nujol)cm$^{-1}$: 1760, 1725–1710, 1705, 1605 NMR (CDCl$_3$) δ: 1.26 (3H,d,J=9 Hz), 1.36 (3H,d,J=6 Hz), 5.15–5.45 (6H,m), 7.40–7.75 (6H,m), 8.25 (6H, d, J=8 Hz)

(2) The compound obtained in the above (1) was hydrogenated in the same manner as that of Example 1-(2) to obtain 225 mg of the title compound.

Melting Point: 168°–171° C. (dec.) IR(Nujol)cm$^{-1}$: 1750, 1725–1700, 1580 NMR(D$_2$O) δ: 1.22 (3H,d,J=7 Hz), 1.28 (3H,d,J=6 Hz), 1.6–1.9 (2H,m), 2.49–2.90 (2H,m)

EXAMPLE 8

Preparation of (1R,5S,6S)-2-[(2S,4S)-2-{(carbamoyl-1-(hydroxymethyl)ethylcarbamoyl)ethylmercaptomethyl}pyrrolidin-4-yl]-thio-6-[(R)-1-hydroxyethyl]-1-methyl-1-carbapen-2-em-3-carboxylic acid (1) The reaction was carried out in the same manner as that of Example 1-(1), starting from 760 mg of 4-nitrobenzyl-2-diphenoxyphosphoryloxy-6-[(R)-1-hydroxyethyl]-1-methyl-1-carbapen-2-em-3-carboxylate and 350 mg of (2S,4S)-[1-(p-nitrobenzyloxycarbonyl)-2-{(carbamoyl-1-(hydroxymethyl)ethylcarbamoyl}-4-mercapto]pyrrolidine to 840 mg of 4-nitrobenzyl (1R,5S, 6S)-2-[(2S,4S)-1-(nitrobenzyloxycarbonyl)-2-{(carbamoyl-1-(hydroxymethyl)ethylcarbamoyl)ethylmercaptomethyl}-pyrrolidin- 4-yl]thio-6-[(R)-1-hydroxyethyl]-1-methyl-1-carbapen-2-em-3-carboxylate.

IR(Nujol)cm$^{-1}$: 1765, 1725, 1710, 1690 NMR(CDCl$_3$) δ: 1.23 (3H,d,J=9 Hz), 1.33 (3H,d,J=8 Hz), 4.42–4.56 (2H,m), 4.82–5.5 (10H,m), 7.4–7.70 (4H,m), 8.25. (6H, d, J=8 Hz)

(2) The compound obtained in the above (1) was hydrogenated in the same manner as that of Example 1-(2) to obtain 250 mg of the title compound.

Melting Point: 163°–167° C. (dec.) IR(KBr)cm$^{-1}$: 1750, 1725–1710 NMR(D$_2$O): δ: 1.22 (3H,d,J=7 Hz), 1.28 (3H, d,J=6 Hz), 1.45–2.00 (4H,m), 2.46–2.95 (3H,m), 3.01–3.13 (3H,m)

EXAMPLE 9

Preparation of (1R,5S,6S)-2-[(2S,4S)-2-{(2-cyano-1-(carbamoylmethyl)ethylcarbamoyl)ethylmercaptomethyl}pyrrolidin-4-yl]thio-6-[(R)-1-hydroxyethyl]-1-methyl-1-carbapen-2-em-3-carboxylic acid (1) The reaction was carried out in the manner as that of Example 1-(1), starting from 820 mg of 4-nitrobenzyl-2- diphenoxyphosphoryloxy-6-[(R)-1-hydroxyethyl]-1-methyl-1-carbapen-2-em-3-carboxylate and 380 mg of (2S, 4S)-[1-(p-nitrobenzyloxycarbonyl)-2-{(cyano-1-(carbamoylmethyl)ethylcarbamoyl)ethylmercaptomethyl}-4-mercapto]pyrrolidine to obtain 920 mg of 4-nitrobenzyl (1R,5S,6S)-2-[(2S,4S)-1-(p-nitrobenzyloxycarbonyl)-2{(cyano-1-(carbamoylmethyl)ethylcarbamoyl)ethylmercaptomethyl}pyrrolidin-4-yl]thio-6-(R)-1-hydroxyethyl-1-methyl-1-carbapen-2-em-3-carboxylate.

IR(Nujol)cm$^{-1}$: 1765, 1715–1705, 1665 NMR(CDCl$_3$) δ: 1.18 (3H,d,J=9 Hz), 1.26 (3H,d,J=9 Hz), 5.15–5.47 (6H,m), 7.40–7.75 (6H,m), 8.25 (6H, d, J=8 Hz)

(2) The compound obtained in the above (1) was hydrogenated in the same manner as that of Example 1-(2) to obtain 270 mg of the title compound.

Melting Point: 163°–164° C. (dec.) IR(Nujol)cm$^{-1}$: 1750, 1725–1705, 1665 NMR(CDCl$_3$) δ: 1.22 (3H,d,J=7 Hz), 1.28 (3H,d,J=6 Hz) 1.60–1.90 (2H,m), 2.50–3.10 (4H,m)

EXAMPLE 10

Preparation of (1R,5S,6S)-2-[(2S,4S)-2-{(carbamoylethyl)mercaptomethyl}pyrrolidin-4-yl]thio-6-[(R)-1-hydroxyethyl]-1-methyl-1-carbapen-2-em-3-carboxylic acid (1) The reaction was carried out in the same manner as that of Example 1-(1), starting from 520 mg of 4-nitrobenzyl-2-diphenoxyphosphoryloxy-6-[(R)-1-hydroxyethyl]-1-methyl-1-carbapen-2-em-3-carboxylate and 270 mg of (2S,4S)-[1-(p-nitrobenzyloxycarbonyl)-2{(carbamoylethyl)mercaptomethyl}-4-mercapto]pyrrolidine to obtain 480 mg of 4-nitrobenzyl (1R,5S, 6S)-2-[(2S,4S)-1-(p-nitrobenzyloxycarbonyl)-2-{(carbamoylethyl)mercaptomethyl}pyrrolidin-4-yl]thio-6-[(R)-1-hydroxyethyl]-1-methyl-1-carbapen-2-em-3-carboxylate.

IR(Nujol)cm$^{-1}$: 1 : 1775–1760, 1690–1660 NMR(CDCl$_3$) δ: 1.26 (3H,d,J=7 Hz), 1.33 (3H,d,J=7 Hz), 1.70–2.15 (2H, m), 2.30–2.80 (2H,m), 4.50–4.83 (4H,m), 7.40–7.65 (4H, m), 8.25 (6H, d, J=8 Hz)

(2) The compound obtained in the above (1) was hydrogenated in the same manner as that of Example 1-(2) to obtain 120 mg of the title compound.

Melting Point: 162°–163° C. (dec.) IR (KBr)cm$^{-1}$: 1765, 1715–1690, 1580 NMR(D$_2$O) δ: 1.27 (3H,d,J=8 Hz), 1.33 (3H,d,J=8 Hz), 2.17–2.50 (4H,m), 2.65–2.95 (2H,m)

EXAMPLE 11

Preparation of (1R,5S,6S)-2-[(2S,4S)-2-{(hydroxyethyl)mercaptomethyl}pyrrolidin-4-yl]thio-6-[(R)-1-hydroxyethyl]-1-methyl-1-carbapen-2-em-3-carboxylic acid (1) The reaction was carried out in the same manner as that of Example 1-(1), starting from 480 mg of 4-nitrobenzyl-2-diphenoxyphosphoryloxy-6-[(R)-1-hydroxyethyl]-1-methyl-1-carbapen-2-em-3-carboxylate and 210 mg of (2S,4S)-[1-(p-nitrobenzyloxycarbonyl)-2-{(hydroxyethyl)-mercaptomethy}-4-mercapto]pyrrolidine to obtain 325 mg of 4-nitrobenzyl(1R, 5S,6S)-2-[(2S,4S)-1-(p-nitrobenzyloxycarbonyl)-2-{(hydroxyethyl)mercaptomethyl}pyrrolidin-4-yl]thio-6-[(R)-1-hydroxyethyl]-1-methyl-1-carbapen-2-em-3-carboxylate.

IR(Neat)cm$^{-1}$: 3400, 1765–1725, 1610–1590 NMR (CDCl$_3$) δ: 1.20–1.80 (6H,m), 5.1–5.6 (4H,m), 7.3–7.70 (4H,m), 8.20 (4H, d, J=8 Hz)

(2) The compound obtained in the above (1) was hydrogenated in the same manner as that of Example 1-(2) to obtain 80 mg of the title compound.

Melting Point: 172°–174° C. (dec.) IR(KBr)cm$^{-1}$: 1760–1730, 1595–1775 NMR(D$_2$O) δ: 1.21 (3H,d,J=8 Hz), 1.28 (3H,d,J=7 Hz) 1.51–2.1 (1H,m), 2.99–2.9 (1H,m)

EXAMPLE 12

Preparation of (1R,5S,6S)-2-[(2S,4S)-2-{(4-(2-hydroxyethyl)piperazinyl)carbonylethylmercaptomethyl}pyrrolidin-4-yl]thio-6-[(R)-1-hydroxyethyl]-1-methyl-1-carbapen-2-em-3-carboxylic acid (1) The reaction was carried out in the same manner as that of Example 1-(1), starting from 720 mg of 4-nitrobenzyl-2-diphenoxyphosphoryloxy-6-[(R)-1-hydroxyethyl]-1-methyl-1-carbapen-2-em-3-carboxylate and 250 mg of (2S,4S)-[1-(p-nitrobenzyloxycarbonyl)-2-{(4-(2-hydroxyethyl)piperazinyl)carbonyethylmercaptomethy}-4-mercapto]pyrrolidine to obtain 870 mg of 4-nitrobenzyl(1R,5S,6S)-2-[(2S,4S)-1-(p-nitrobenzyloxycarbonyl)-2-{(4-2-hydroxyethyl)piperazinyl)carbonylethylmercaptomethyl}pyrrolidin-4-yl]thio-6-[(R)-1-hydroxyethyl]-1-methyl-1-carbapen-2-em-3-carboxylate.

IR(Neat)cm$^{-1}$: 3400, 1760–1750, 1690, 1525 NMR (CDCl$_3$) δ: 1.26 (3H,d,J=6 Hz), 1.33 (3H,d,J=6 Hz), 1.80–2.18 (4H,m), 2.27–2.38 (4H,m), 5.10–5.63 (4H,m), 7.48 (2H, d, J=8 Hz), 7.62 (2H, d, J=8 Hz), 8.16–8.27 (4H, d, J=8 Hz)

(2) The compound obtained in the above (1) was hydrogenated in the same manner as that of Example 1-(2) to obtain 210 mg of the title compound.

Melting Point: 168°–170° C. (dec.) IR(KBr)cm$^{-1}$: 3400, 1760–1735, 1600–1580 NMR(D$_2$O) δ: 1.23 (3H,d,J=8 Hz), 1.28 (3H,d,J=8 Hz), 1.45–1.85 (2H,m), 2.30–2.66 (3H,m), 2.38–3.0 (3H m)

EXAMPLE 13

Preparation of (1R,5S,6S)-2-[(2S,4S)-2-{(4(2-hydroxyethyl)piperazinylcarbonylmethylcarbamoyl)ethylmercaptomethyl}pyrrolidin-4-yl]thio-6-[(R)-1-hydroxyethyl]-1-methyl-1-carbapen-2-em-3-carboxylic acid (1) The reaction was carried out in the same manner as that of Example 1-(1), starting from 680 mg of 4-nitrobenzyl-2-diphenoxyphosphoryloxy-6-[(R)-1-hydroxyethyl]-1-methyl-1-carbapen-2-em-3-carboxylate and 290 mg of (2S,4S)-[1-(p-nitrobenzyloxycarbonyl)-2-{((4-(2-hydroxyethyl)piperazinylcarbonylmethylcarbamoyl)ethylmercaptomethy}-4-mercapto]-pyrrolidine to obtain 580 mg of 4-nitrobenzyl(1R,5S,6S)-2-[(2S,4S)-1-(p-nitrobenzyloxycarbonyl)-2-{((4-(2-hydroxyethyl)piperazinylcarbonylmethylcarbamoyl)ethylmercaptomethyl}pyrrolidin-4-yl]thio-6-[(R)-1-hydroxyethyl]-1-methyl-1-carbapen-2-em-3-carboxylate.

IR(Neat)cm$^{-1}$: 3400, 1770, 1705, 1650 NMR(CDCl$_3$) δ: 1.25 (3H,d,J=7.5 Hz), 1.32 (3H,d,J=6 Hz) 2.21–2.38 (2H, m), 3.10–4.83 (4H,m), 4.85 (2H, br. s), 5.24 (2H,s), 7.52 (2H, d, J=8 Hz), 7.65 (2H, d, J=8 Hz), 8.25 (4H, d, J=8 Hz)

(2) The compound obtained in the above (1) was hydrogenated in the same manner as that of Example 1-(2) to obtain 90 mg of the title compound.

Melting Point: 180°–182° C. (dec.) IR(KBr)cm⁻¹: 3400, 1755, 1680 NMR(D₂O) δ: 1.22 (3H,d,J=8 Hz), 1.30 (3H,d, J=8 Hz), 1.57–2.35 (6H,m), 3.01–3.55 (2H,m)

EXAMPLE 14

Preparation of (1R,5S,6S)-2-[(2S,4S)-2-{(aminocarbonyloxymethylcarbamoyl) ethylmercaptomethyl}pyrrolidin-4-yl]thio-6-[(R)-1-hydroxyethyl]-1-methyl-1-carbapen-2-em-3-carboxylic acid (1) The reaction was carried out in the same manner as that of Example 1-(1), starting from 420 mg of 4-nitrobenzyl-2-diphenoxyphosphoryloxy-6-[(R)-1-hydroxyethyl]-1-methyl-1-carbapen-2-em-3-carboxylate and 280 mg of (2S,4S)-[1-(p-nitrobenzyloxycarbonyl)-2-{(aminocarbonyloxymethylcarbamoyl) ethylmercaptomethy}-4-mercapto]pyrrolidine to obtain 380 mg of 4-nitrobenzyl(1R,5S,6S)-2-[(2S,4S)-1-(p-nitrobenzyloxycarbonyl)-2-{(aminocarbonyloxymethylcarbamoyl) ethylmercaptomethyl}-pyrrolidin-4-yl]thio6-[(R)-1-hydroxyethyl]-1-methyl-1-carbapen-2-em-3-carboxylate.

IR(Neat)cm⁻¹: 3400, 1765, 1725–1715, 1610–1600, 1512, 1360 NMR(CDCl₃) δ: 1.1–1.6 (6H,m), 4.25–5.8 (6H, m), 7.4–8.2 (4H,m), 8.15 (4H, d, J=8.5 Hz)

(2) The compound obtained in the above (1) was hydrogenated in the same manner as that of Example 1-(2) to obtain 110 mg of the title compound.

Melting Point: >170° C. (dec.) IR(KBr)cm⁻¹: 1750, 1700–1690, 1600–1580 NMR(D₂O) δ: 1.23 (3H,d,J=7.0 Hz), 1.29 (3H,d,J=6 Hz), 1.6–2.1 (2H,m), 2.5–3.0 (2H,m)

EXAMPLE 15

Preparation of (1R,5S,6S)-2-[(2S,4S)-2-{2-(ureidomethylcarbamoyl) ethylmercaptomethyl}pyrrolidin- 4-yl]thio-6-[(R)-1-hydroxyethyl]-1-methyl-1-carbapen-2-em-3-carboxylic acid (1) The reaction was carried out in the same manner as that of Example 1-(1) starting from 580 mg of 4-nitrobenzyl-2-diphenoxyphosphoryloxy-6-[(R)-1-hydroxyethyl]-1-methyl-1-carbapen-2-em-3-carboxylate and 275 mg of (2S,4S)-[1-(p-nitrobenzyloxycarbonyl)-2-{2-(ureidomethylcarbamoyl)ethylmercaptomethy}-4-mercapto]pyrrolidine to obtain 425 mg of 4-nitrobenzyl(1R,5S,6S)-2-[(2S,4S)-1-(p-nitrobenzyloxycarbonyl)-2-{2-(ureidomethylcarbamoyl)ethylmercaptomethyl}pyrrolidin-4-yl]thio-6-[(R)-1-hydroxyethyl]-1-methyl-1-carbapen-2-em-3-carboxylate.

IR(Neat)cm⁻¹: 3400, 1775, 1710–1690, 1610, 1525–1510, 1350 NMR(CDCl₃) δ: 1.25–1.35 (6H,m), 3.05–4.25 (10H,m) 4.80 (2H, br. s), 5.20 (2H,s), 5.40 (2H, dd, J=14 Hz) 7.56 (2H, d, J=8 Hz) 7.68 (2H, d, J=8 Hz), 8.26 (4H, d, J=8 Hz)

(2) The compound obtained in the above (1) was hydrogenated in the same manner as that of Example 1-(2) to obtain 90 mg of the title compound.

Melting Point: >175° C. (dec.) IR(KBr)cm⁻¹: 1760, 1710, 1650, 1580 NMR(D₂O) δ: 1.21 (3H,d,J=9 Hz), 1.28 (3H,d, J=6 Hz), 1.42–2.10 (4H,m), 2.53–4.36 (14H,m)

EXAMPLE 16

Preparation of (1R,5S,6S)-2-[(2S,4S)-2-{2-(aminomethylcarbamoyl) ethylmercaptomethyl}pyrrolidin-4-yl]thio-6-[(R)-1-hydroxyethyl-1-methyl-1-carbapen-2-em-3-carboxylic acid (1) The reaction was carried out in the same manner as that of Example 1-(1), starting from 620 mg of 4-nitrobenzyl-2-diphenoxyphosphoryloxy-6-[(R)-1-hydroxyethyl]-1-methyl-1-carbapen-2-em-3-carboxylate and 380 mg of (2S,4S)-[1-(p-nitrobenzyloxycarbonyl)-2-{2-((4-nitrobenzyloxycarbonyl)methylcarbamoyl) ethylmercaptomethyl}-4-mercapto]pyrrolidine to obtain 420 mg of 4-nitrobenzyl (1R,5S,6S)-2-[(2S,4S)-1(p-nitrobenzyloxycarbonyl)-2-{2-((4-nitrobenzyloxycarbonyl)methylcarbamoyl)ethylmercaptomethyl}pyrrolidin-4-yl]thio-6-[(R)-1-hydroxyethyl]1-methyl-1-carbapen-2-em-3-carboxylate.

IR(Nujol)cm⁻¹: 1765–1700, 1710–1690, 1660–1650, 1530–1510

(2) The compound obtained in the above (1) was hydrogenated in the same manner as that of Example 1-(2) to obtain 190 mg of the title compound.

Melting Point: >180° C. (dec.) IR(Nujol)cm⁻¹: 1760–1750, 1590–1580, 1350 NMR(D₂O) δ: 1.21 (3H,d,J=7 Hz) 1.30 (3H,d,J=7 Hz), 1.40–2.1 (4H,m), 2.55–3.08 (4H, m), 3.12–4.35 (9H,m)

EXAMPLE 17

Preparation of (1R,5S,6S)-2-[(2S,4S)-2-{(2-(methoxymethylcarbamoyl) ethylmercaptomethyl}pyrrolidin-4-yl]thio-6-[(R)-1-hydroxyethyl]-1-methyl-1-carbapen-2-em-3-carboxylic acid (1) The reaction was carried out in the same manner as that of Example 1-(1), starting from 510 mg of 4-nitrobenzyl-2-diphenoxyphosphoryloxy-6-[(R)-1-hydroxyethyl]-1-methyl-1-carbapen-2-em-3-carboxylate and 250 mg of (2S,4S)-[1-(p-nitrobenzyloxycarbonyl)-2-{2-(methoxymethylcarbamoyl)ethylmercaptomethy}-4-mercapto]pyrrolidine to obtain 420 mg of 4-nitrobenzyl (1R,5S,6S)-2-[(2S,4S)-1-(p-nitrobenzyloxycarbonyl)-2-{2-(methoxymethylcarbamoyl)ethylmercaptomethyl} pyrrolidin-4-yl]thio-6-[(R)-1-hydroxyethyl]-1-methyl-1-carbapen-2-em-3-carboxylate.

IR(Nujol)cm⁻¹: 1750, 1700, 1685, 1516 NMR(CDCl₃) δ: 1.28 (3H,d,J=7 Hz), 1.37 (3H,d,J=7 Hz), 1.65–2.10 (3H,m), 2.35–2.85 (2H,m), 2.94 (3H,s), 5.25 (4H,s), 5.40–5.75 (2H, m), 7.56 (2H, d, J=9 Hz), 7.66 (2H, d, J=9 Hz), 8.26 (4H, d, J=9 Hz)

(2) The compound obtained in the above (1) was hydrogenated in the same manner as that of Example 1-(2) to obtain 110 mg of the title compound.

Melting Point:>178° C. (dec.) IR(KBr)cm⁻¹: 1760–1750 1590–1580, 1350 NMR(D₂O) δ: 1.22 (3H,d,J=7 Hz), 1.28 (3H,d,J=6 Hz), 1.45–2.10 (4H,m), 2.24–2.95 (2H,m), 3.13 (3H,s)

The compounds of the following Examples 18 to 27 can be prepared in the same manner as that of Example 1 using the corresponding starting materials.

EXAMPLE 18

(1) (1R,5R,6S)-2-[(2S,4S)-1-(p-nitrobenzyloxycarbonyl)-2-{2-((4-cyanoethylpiperazinyl)carbonylmethylcarbamoyl) ethylmercaptomethyl}pyrrolidin-4-yl]thio-6-(R)-1-hydroxyethyl]-1-methyl-1-carbapen-2-em-3-carboxylic acid IR(Neat)cm⁻¹: 3600, 1765, 1710–1685, 1610, 1520 NMR (CDCl₃) δ: 1.30–1.38 (6H, dd, J=18 Hz), 2.25–2.83 (7H,m), 3.18–350 (3H,m), 5.20–5.52 (4H,m), 7.56–7.69 (4H,m), 8.28 (4H, d,=9 Hz)

(2)  (1R,5S,6S)-2-[(2S,4S)-2-{2-((4-cyanoethylpiperazinyl)carbonylmethylcarbamoyl)

ethylmercaptomethyl}pyrrolidin-4-yl]thio-6-[(R)-1-hydroxyethyl]-1-methyl-1-carbapen-2-em-3-carboxylic acid UV$_{max}^{H_2O}$: 298.2 nm IR(Nujol)cm$^{-1}$: 1755, 1710, 1585 NMR(D$_2$O) δ: 1.22 (3H,d,J=6 Hz), 1.31 (3H,d,J=6 Hz), 1.75–2.35 (5H,m)

EXAMPLE 19

(1) (1R,5S,6S)-2-[(2S,4S)-1-(p-nitrobenzyloxycarbonyl)-2-{2-((4-p-nitrobenzyloxycarbonylaminoethylpiperazinyl)carbonylmethylcarbamoyl)ethylmercaptomethyl}pyrrolidin-4-yl]-thio-6-[(R)-1-hydroxyethyl]-1-methyl-1-carbapen-2-em-3-carboxylic acid IR(Neat)cm$^{-1}$: 1765–1750, 1710, 1660–1640 1530–1510 NMR(CDCl$_3$) δ: 1.30 (3H,d,J=7 Hz), 1.38 (3H,d,J=7 Hz), 1.75–2.10 (3H,m), 2.80–3.90 (10H,m), 3.90–4.40 (4H,m), 5.20–5.50 (6H,m), 7.55 (4H, d, J=8 Hz), 7.66–8.25 (4H, dd)

(2) (1R,5S,6S)-2-[(2S,4S)-2-{2-((4-aminoethylpiperazinyl)carbonylmethylcarbamoyl)ethylmercaptomethyl}pyrrolidin-4-yl]-thio-6-[(R)-1-hydroxyethyl]-1-methyl-1-carbapen-2-em-3-carboxylic acid UV$_{max}^{H_2O}$: 297.8 nm IR(Nujol)cm$^{-1}$: 1750, 1590–1580 NMR(D$_2$O) δ: 1.22 (5H, d, J=7 Hz), 1.30 (3H,d,J=7 Hz), 1.45–1.95 (3H,m), 2.55–3.08 (4H,m), 3.12–4.35 (10H,m)

EXAMPLE 20

(1) (1R,5S,6S)-2-[(2S,4S)-1-(p-nitrobenzyloxycarbonyl)-2-{2-(4-(2-methoxyethyl)piperazinyl)carbonylmethylcarbamoylethylmercaptomethyl}pyrrolidin-4-yl]-thio-6-[(R)-1-hydroxyethyl]-1-methyl-1-carbapen-2-em-3-carboxylic acid IR(Neat)cm$^{-1}$: 1765–1755, 1700, 1685, 1516, 1392 NMR (CDCl$_3$) δ: 1.27 (3H,d,J=7 Hz) 1.34 (3H,d,J=7 Hz), 2.76 (4H,m), 3.30 (3H,s), 5.21 (2H,s), 7.50–7.69 (4H,m), 8.28 (4H, d, J=9 Hz)

(2) (1R,5S,6S)-2-[(2S,4S)-2-{2-(4-(2-methoxyethyl)piperazinyl)carbonylmethylcarbamoylethylmercaptomethyl}pyrrolidin-4-yl]-thio-6-[(R)-1-hydroxyethyl]-1-methyl-1-carbapen-2-em-3-carboxylic acid UV$_{max}^{H_2O}$: 298 nm IR(Nujol)cm$^{-1}$: 1745–1750, 1650, 1585, 1380 NMR(D$_2$O) δ: 1.19 (3H,d,J=7 Hz), 1.27 (3H,d, J=6 Hz), 2.72 (3H,s), 2.79–3.14 (4H,m) 3.30 (3H,s), 4.05–4.20 (4H,m)

EXAMPLE 21

(1) (1R, 5S,6S)-2-[(2S,4S)-1-(p-nitrobenzyloxycarbonyl)-2-{2-(4-(2-carbamoyloxyethyl)piperazinylcarbonyl)methylcarbamoylethylmercaptomethyl}pyrrolidin-4-yl]-thio-6-[(R)-1-hydroxyethyl]-1-methyl-1-carbapen-2-em-3-carboxylic acid IR(Neat)cm$^{-1}$: 1785, 1740, 1705, 1525, 1348 NMR (CDCl$_3$) δ: 1.35 (3H,d,J=6 Hz), 1.48 (3H,d,J=7 Hz), 1.95–2.05 (2H,m), 2.65–3.40 (3H,m), 5.22 (2H,s), 7.5–7.8 (4H, dd, J=19 Hz), 8.20 (4H, d, J=8 Hz)

(2) (1R,5S,6S)-2-[(2S,4S)-2-{2-(4-(2-carbamoyloxyethyl)piperazinylcarbonyl)methylcarbamoylethylmercaptomethyl}pyrrolidin-4-yl]-thio-6-[(R)-1-hydroxyethyl]-1-methyl-1-carbapen-2-em-3-carboxylic acid UV$_{max}^{H_2O}$: 297.8 nm IR(Nujol)cm$^{-1}$: 1750, 1725–1710, 1600–1580 NMR(D$_2$O) δ: 1.22 (3H,d,J=7 Hz), 1.28 (3H,d, J=6 Hz), 1.6–1.9 (4H,m), 2.5–2.9 (1H,m)

EXAMPLE 22

(1) (1R,5S,6S)-2-[(2S,4S)-1-(p-nitrobenzyloxycarbonyl)-2-{2-(4-(2-ureidoethyl)piperazinyl)carbonylmethyl carbamoyl)ethylmercaptomethyl}pyrrolidin-4-yl]-thio-6-[(R)-1-hydroxyethyl]-1-methyl-1-carbapen-2-em-3-carboxylic acid IR(Nujol)cm$^{-1}$: 1770, 1700, 1610, 1525, 1350 NMR (CDCl$_3$) δ: 1.27 (3H,d,J=7 Hz), 1.32 (3H,d,J=6 Hz), 2.85–3.90 (11H,m), 4.80 (2H, br. s), 5.25 (2H,s), 5.37 (2H, dd, J=18 Hz), 7.56–7.68 (4H, dd, J=18 Hz), 8.26 (4H, d, J=8 Hz)

(2) (1R,5S,6S)-2-[(2S,4S)-2-{2-(4-(2-ureidoethyl)piperazinyl)carbonylmethylcarbamoyl)ethylmercaptomethyl}pyrrolidin-4-yl]-thio-6-[(R)-1-hydroxyethyl]-1-methyl-1-carbapen-2-em-3-carboxylic acid UV$_{max}^{H_2O}$: 298.5 nm IR(Nujol)cm$^{-1}$: 1755, 1700, 1650, 1580 NMR(CDCl$_3$) δ: 1.25 (3H,d,J=7 Hz), 1.33 (3H,d,J=6 Hz), 1.42–2.03 (2H,m), 2.53–4.50 (45H,m)

EXAMPLE 23

(1) (1R,5S,6S)-2-[(2S,4S)-1-(p-nitrobenzyloxycarbonyl-2-{(2-methoxymethyloxymethylcarbamoylethyl)mercaptomethyl}pyrrolidin-4-yl]-thio-6-[(R)-1-hydroxyethyl]-1-methyl-1-carbapen-2-em-3-carboxylic acid IR(Neat)cm$^{-1}$: 1765–1750, 1700, 1680 NMR(CDCl$_3$) δ: 1.27 (3H,d,J=7 Hz), 1.34 (3H,d,J=7 Hz), 2.25–2.60 (3H,m), 3.35 (3H,s), 5.21 (2H,s), 7.55–7.70 (4H,m), 8.26 (4H, d, J=9 Hz)

(2) (1R,5S,6S)-2-[(2S,4S)-2-{(2-methoxymethyloxymethylcarbamoylethyl)mercaptomethyl}pyrrolidin-4-yl]-thio-6-[(R)-1-hydroxyethyl]-1-methyl-1-carbapen-2-em-3-carboxylic acid UV$_{max}^{H_2O}$: 298.7 nm IR(Nujol)cm$^{-1}$: 1750–1745, 1700, 1655, 1580, 1350 NMR(D$_2$O) δ: 1.20 (3H,d,J=7 Hz), 1.26 (3H,d,J=7 Hz), 2.73 (3H,s), 2.77–3.15 (4H,m), 3.33 (3H,s), 4.10–4.15 (3H,m)

EXAMPLE 24

(1) (1R,5S,6S)-2-[(2S,4S)-1-(p-nitrobenzyloxycarbonyl)-2-{(2-methylcarbamoyloxymethylcarbamoylethyl)mercaptomethyl}pyrrolidin-4-yl)-thio-6-[(R)-1-hydroxyethyl]-1-methyl-1-carbapen-2-em-3-carboxylic acid IR(Neat)cm$^{-1}$: 3500–3400, 1765, 1720–1700, 1605 NMR (CDCl$_3$) δ: 1.1–1.8 (6H,m), 5.10–5.75 (4H,m), 7.4–7.8 (4H,m), 8.21 (4H, d, J=8.5 Hz)

(2) (1R,5S,6S)-2-[(2S,4S)-2-{(2-methylcarbamoyloxymethylcarbamoylethyl)mercaptomethyl}pyrrolidin-4-yl]-thio-6-[(R)-1-hydroxyethyl]-1-methyl-1-carbapen-2-em-3-carboxylic acid UV$_{max}^{H_2O}$: 297.8 nm IR(Nujol)cm$^{-1}$: 1750 1725–1705, 1580 NMR(D$_2$O) δ: 1.25 (3H,d,J=7 Hz), 1.28 (3H,d,J=8 Hz), 1.6–1.9 (2H,m), 2.4–2.9 (2H,m)

EXAMPLE 25

(1) (1R,5S,6S)-2-[(2S,4S)-1-(p-nitrobenzyloxycarbonyl)-2-{(2-ureidoethylcarbamoylethyl)mercaptomethyl}pyrrolidin-4-yl]-thio-6-[(R)-1-hydroxyethyl]-1-methyl-1-carbapen-2-em-3-carboxylic acid IR(Neat)cm$^{-1}$: 1770–1760, 1710–1705, 1610–1605, 1525 NMR(CDCl$_3$) δ: 1.27 (3H,d,J=7 Hz), 1.33 (3H,d,J=7 Hz), 3.10–3.95 (13H,m), 4.85 (2H, br. s), 5.24 (2H,s), 5.50 (2H, d, J=7 Hz), 7.56–7.68 (4H, dd, J=18 Hz), 8.26 (4H, d, J=8 Hz)

(2) (1R,5S,6S)-2-[(2S,4S)-2-{(2-ureidoethylcarbamoylethyl)mercaptomethyl}pyrrolidin-4-yl]-thio-6-[(R)-1-hydroxyethyl]-1-methyl-1-carbapen-2-em-3-carboxylic acid $UV_{max}^{H_2O}$: 298.2 nm IR(Nujol)cm$^{-1}$: 1755, 1650, 1580 NMR(D$_2$O) δ: 1.20 (3H,d,J=9 Hz), 1.25 (3H,d,J=6 Hz), 1.45–2.10 (4H,m) 2.53–4.35 (14H,m)

EXAMPLE 26

(1) (1R,5S,6S)-2-[(2S,4S)-1-(p-nitrobenzyloxycarbonyl)-2-{(2-(p-nitrobenzyloxycarbonyl)aminoethylcarbamoylethyl)mercaptomethyl}pyrrolidin-4-yl]-thio-6-[(R)-1-hydroxyethyl]-1-methyl-1-carbapen-2-em-3-carboxylic acid IR(Neat)cm$^{-1}$: 1765–1750, 1710, 1665–1650, 1510 NMR (CDCl$_3$) δ: 1.24 (3H,d,J=7 Hz) 1.36 (3H,d,J=7 Hz) 2.35–2.50 (2H,m), 3.15–3.46 (3H,m), 3.56–4.40 (12H,m), 5.12–5.50 (6H,m), 7.36–7.80 (6H,m), 8.24 (6H, d, J=8 Hz)

(2) (1R,5S,6S)-2-[(2S,4S)-2-{(2-aminoethylcarbamoylethyl)mercaptomethyl}pyrrolidin-4-yl]-thio-6-[(R)-1-hydroxyethyl]-1-methyl-1-carbapen-2-em-3-carboxylic acid $UV_{max}^{H_2O}$: 298.5 nm IR(Nujol)cm$^{-1}$: 1770, 1705, 1610, 1525, 1350 NMR(D$_2$O) δ: 1.25 (3H,d,J=7 Hz), 1.33 (3H,d, J=6 Hz), 1.43–2.15 (4H,m), 2.55–4.25 (14H,m)

EXAMPLE 27

(1) (1R, 5S, 6S)-2-[(2S, 4S)-1-(p-nitrobenzyloxycarbonyl)-2-{(2-methoxymethyloxyethylcarbamoylethyl)mercaptomethyl}pyrrolidin-4-yl]-thio-6-[(R)-1-hydroxyethyl]-1-methyl-1-carbapen-2-em-3-carboxylic acid IR(Neat)cm$^{-1}$: 1770–1750, 1710–1700, 1690, 1605, 1520 NMR(CDCl$_3$) δ: 1.28 (3H,d,J=7 Hz), 1.37 (3H d, J=7 Hz), 1.65–2.10 (5H,m), 2.35–2.85 (4H,m), 2.94–3.10 (4H,m), 3.25 (3H,s), 5.40–5.74 (2H,m), 7.56 (2H, d, J=9 Hz), 7.66 (2H, d, J=9 Hz), 8.26 (4H, d, J=9 Hz)

(2) (1R,5S,6S)-2-[(2S,4S)-2-{(2-methoxymethyloxyethylcarbamoylethyl)mercaptomethyl}pyrrolidin-4-yl]-thio-6-[(R)-1-hydroxyethyl]-1-methyl-1-carbapen-2-em-3-carboxylic acid $UV_{max}^{H_2O}$: 299.0 nm IR(Nujol)cm$^{-1}$: 1760–1750, 1700, 1590–1580, 1380 NMR(D$_2$O) δ : 1.22 (3H,d,J=7 Hz), 1.28 (3H,d,J=7 Hz), 1.48–2.00 (4H,m), 2.46–2.95 (2H,m), 3.15 (3H,s)

The specific examples of the compound of formula (I) which can be prepared in the same manner as that of Example 1 are listed in the following Table.

| No | R$_1$ | R$_2$ | R$_3$ | R$_5$ | R$_6$ | X | m |
|----|----|----|----|----|----|---|---|
| 1 | Me | H | H | H | CH | O | 1 |
| 2 | Me | H | H | H | CN | O | 1 |
| 3 | Me | H | H | H | NH$_2$ | O | 1 |
| 4 | Me | H | H | H | CONH$_2$ | O | 1 |
| 5 | Me | H | H | H | CONHCH$_3$ | O | 1 |
| 6 | Me | H | H | H | CON(CH$_3$)$_2$ | O | 1 |
| 7 | Me | H | H | H | OCONH$_2$ | O | 1 |
| 8 | Me | H | H | H | NHCONH$_2$ | O | 1 |
| 9 | Me | H | H | H | CH | O | 2 |
| 10 | Me | H | H | H | CN | O | 2 |
| 11 | Me | H | H | H | NH$_2$ | O | 2 |
| 12 | Me | H | H | H | CONH$_2$ | O | 2 |
| 13 | Me | H | H | H | CONHCH$_3$ | O | 2 |
| 14 | Me | H | H | H | CON(CH$_3$)$_2$ | O | 2 |
| 15 | Me | H | H | H | OCONH$_2$ | O | 2 |
| 16 | Me | H | H | H | NHCONH$_2$ | O | 2 |
| 17 | Me | H | H | H | CH$_2$OH | O | 1 |
| 18 | Me | H | H | H | CH$_2$CN | O | 1 |
| 19 | Me | H | H | H | CH$_2$NH$_2$ | O | 1 |
| 20 | Me | H | H | H | CH$_2$OCNH$_2$ (C=O) | O | 1 |
| 21 | Me | H | H | H | CH$_2$CNH$_2$ (C=O) | O | 1 |
| 22 | Me | H | H | H | CH$_2$CNHCH$_3$ (C=O) | O | 1 |
| 23 | Me | H | H | H | CH$_2$CN(CH$_3$)$_2$ (C=O) | O | 1 |

-continued

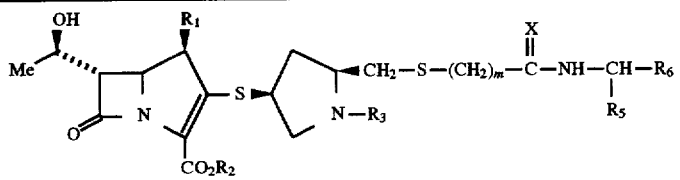

| No | R₁ | R₂ | R₃ | R₅ | R₆ | X | m |
|----|----|----|----|----|----|---|---|
| 24 | Me | H | H | H | CH₂NHCONH₂ | O | 1 |
| 25 | Me | H | H | H | CH₂CN | O | 2 |
| 26 | Me | H | H | H | CH₂OH | O | 2 |
| 27 | Me | H | H | H | CH₂NH₂ | O | 2 |
| 28 | Me | H | H | H | CH₂CONH₂ | O | 2 |
| 29 | Me | H | H | H | CH₂CONHCH₃ | O | 2 |
| 30 | Me | H | H | H | CH₂CON(CH₃)₂ | O | 2 |
| 31 | Me | H | —C(H)=NH | H | CH₂OH | O | 1 |
| 32 | Me | H | —C(H)=NH | H | CH₂CN | O | 1 |
| 33 | Me | H | —C(H)=NH | H | CH₂NH₂ | O | 1 |
| 34 | Me | H | —C(H)=NH | H | CH₂CONH₂ | O | 1 |
| 35 | Me | H | —C(H)=NH | H | CH₂OCONH₂ | O | 1 |
| 36 | Me | H | —C(H)=NH | H | CH₂NHCONH₂ | O | 1 |
| 37 | Me | H | —C(H)=NH | H | CH₂OH | O | 2 |
| 38 | Me | H | —C(H)=NH | H | CH₂CN | O | 2 |
| 39 | Me | H | —C(H)=NH | H | CH₂NH₂ | O | 2 |
| 40 | Me | H | —C(H)=NH | H | CH₂COH₂ | O | 2 |
| 41 | Me | H | —C(H)=NH | H | CH₂OCONH₂ | O | 2 |
| 42 | Me | H | —C(H)=NH | H | CH₂NH₂CONH₂ | O | 2 |
| 43 | Me | H | —C(CH₃)=NH | H | CH₂OH | O | 1 |
| 44 | Me | H | —C(CH₃)=NH | H | CH₂CN | O | 1 |
| 45 | Me | H | —C(CH₃)=NH | H | CH₂NH₂ | O | 1 |
| 46 | Me | H | —C(CH₃)=NH | H | CH₂CONH₂ | O | 1 |

-continued

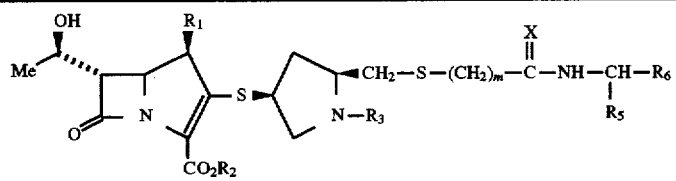

| No | R₁ | R₂ | R₃ | R₅ | R₆ | X | m |
|----|----|----|----|----|----|----|----|
| 47 | Me | H | −C(CH₃)=NH | H | CH₂OCONH₂ | O | 1 |
| 48 | Me | H | −C(CH₃)=NH | H | CH₂NHCONH₂ | O | 1 |
| 49 | Me | H | −C(CH₃)=NH | H | CH₂OH | O | 2 |
| 50 | Me | H | −C(CH₃)=NH | H | CH₂CN | O | 2 |
| 51 | Me | H | −C(CH₃)=NH | H | CH₂NH₂ | O | 2 |
| 52 | Me | H | −C(CH₃)=NH | H | CH₂CONH₂ | O | 2 |
| 53 | Me | H | −C(CH₃)=NH | H | CH₂OCONH₂ | O | 2 |
| 54 | Me | H | −C(CH₃)=NH | H | CH₂CONHCH₃ | O | 2 |
| 55 | Me | H | −C(CH₃)=NH | H | CH₂NHCONH₂ | O | 2 |
| 56 | Me | H | H | H | CON(aziridinyl) | O | 1 |
| 57 | Me | H | H | H | CON(azetidinyl) | O | 1 |
| 58 | Me | H | H | H | CON(pyrrolidinyl) | O | 1 |
| 59 | Me | H | H | H | CON(piperidinyl) | O | 1 |
| 60 | Me | H | H | H | CON(pyrrolidinyl-2-CONH₂) | O | 1 |
| 61 | Me | H | H | H | CON(piperidinyl-CONH₂) | O | 1 |

-continued
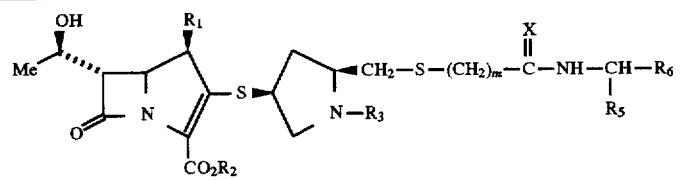
| No | R₁ | R₂ | R₃ | R₅ | R₆ | X | m |
|----|----|----|----|----|----|----|----|
| 62 | Me | H | H | H | CON⌒NH (piperazine) | O | 1 |
| 63 | Me | H | H | H | CON⌒NCH₃ | O | 1 |
| 64 | Me | anion | H | H | CON⌒N⁺(CH₃)₂ | O | 1 |
| 65 | Me | H | H | H | CON⌒N(CH₂)₂OH | O | 1 |
| 66 | Me | H | H | H | CON⌒NCH₂CN | O | 1 |
| 67 | Me | H | H | H | CON⌒N(CH₂)₂NH₂ | O | 1 |
| 68 | Me | H | H | H | CON⌒NCH₂OCNH₂ (O=) | O | 1 |
| 69 | Me | H | H | H | CON (aziridine) | O | 2 |
| 70 | Me | H | H | H | CON (azetidine) | O | 2 |
| 71 | Me | H | H | H | CON (pyrrolidine) | O | 2 |
| 72 | Me | H | H | H | CON (piperidine) | O | 2 |
| 73 | Me | H | H | H | CON (pyrrolidine-2-carboxamide) | O | 2 |

-continued
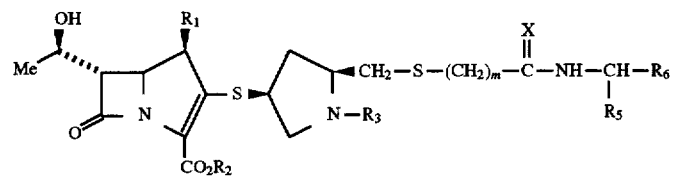
| No | R₁ | R₂ | R₃ | R₅ | R₆ | X | m |
|---|---|---|---|---|---|---|---|
| 74 | Me | H | H | H | CON⟨⟩—C(O)NH₂ (piperidine with CONH₂) | O | 2 |
| 75 | Me | H | H | H | CON⟨⟩NH (piperazine) | O | 2 |
| 76 | Me | H | H | H | CON⟨⟩NCH₃ | O | 2 |
| 77 | Me | anion | H | H | CON⟨⟩N⁺(CH₃)₂ | O | 2 |
| 78 | Me | H | H | H | CON⟨⟩N(CH₂)₂OH | O | 2 |
| 79 | Me | H | H | H | CON⟨⟩NCH₂CN | O | 2 |
| 80 | Me | H | H | H | CON⟨⟩N(CH₂)₂NH₂ | O | 2 |
| 81 | Me | H | H | H | CON⟨⟩NCH₂OC(O)NH₂ | O | 2 |
| 82 | Me | H | H | H | CH₂CON⟨ (aziridine) | O | 1 |
| 83 | Me | H | H | H | CH₂CON⟨ (azetidine) | O | 1 |
| 84 | Me | H | H | H | CH₂CON⟨ (pyrrolidine) | O | 1 |
| 85 | Me | H | H | H | CH₂CON⟨ (piperidine) | O | 1 |

-continued

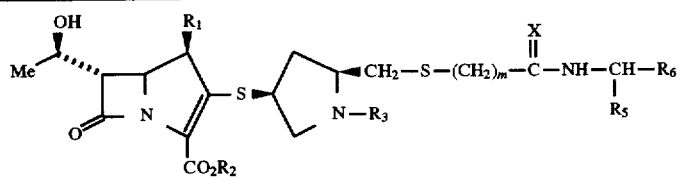

| No | R₁ | R₂ | R₃ | R₅ | R₆ | X | m |
|----|----|----|----|----|----|----|---|
| 86 | Me | H | H | H | CH₂CON⟨pyrrolidine-CONH₂⟩ | O | 1 |
| 87 | Me | H | H | H | CH₂CON⟨piperidine-CONH₂⟩ | O | 1 |
| 88 | Me | H | H | H | CH₂CON⟨piperazine-NH⟩ | O | 1 |
| 89 | Me | H | H | H | CH₂CON⟨piperazine-NCH₃⟩ | O | 1 |
| 90 | Me | anion | H | H | CH₂CON⟨piperazine-N⁺(CH₃)₂⟩ | O | 2 |
| 91 | Me | H | H | H | CH₂CON⟨piperazine-NCH₂OH⟩ | O | 1 |
| 92 | Me | H | H | H | CH₂CON⟨piperazine-NCH₂CN⟩ | O | 1 |
| 93 | Me | H | H | H | CH₂CON⟨piperazine-NCH₂NH₂⟩ | O | 1 |
| 94 | Me | H | H | H | CH₂CON⟨piperazine-NCH₂OCNH₂⟩ | O | 1 |
| 95 | Me | H | H | H | CH₂CON⟨azetidine⟩ | O | 2 |
| 96 | Me | H | H | H | CH₂CON⟨azetidine⟩ | O | 2 |
| 97 | Me | H | H | H | CH₂CON⟨pyrrolidine⟩ | O | 2 |

-continued

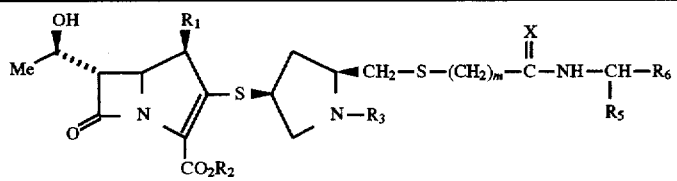

| No | R₁ | R₂ | R₃ | R₅ | R₆ | X | m |
|---|---|---|---|---|---|---|---|
| 98 | Me | H | H | H | CH₂CON-piperidinyl | O | 2 |
| 99 | Me | H | H | H | CH₂CON-(pyrrolidinyl with C(=O)NH₂ substituent) | O | 2 |
| 100 | Me | H | H | H | CH₂CON-(piperidinyl with C(=O)NH₂ substituent) | O | 2 |
| 101 | Me | H | H | H | CH₂CON-piperazinyl-NH | O | 2 |
| 102 | Me | H | H | H | CH₂CON-piperazinyl-NCH₃ | O | 2 |
| 103 | Me | H | H | H | CH₂CON-piperazinyl-N⁺(CH₃)₂ | O | 2 |
| 104 | Me | H | H | H | CH₂CON-piperazinyl-NCH₂OH | O | 2 |
| 105 | Me | H | H | H | CH₂ON-piperazinyl-NCH₂CN | O | 2 |
| 106 | Me | H | H | H | CH₂ON-piperazinyl-NNH₂ | O | 2 |
| 107 | Me | H | —C(=NH)H | H | CN | O | 1 |
| 108 | Me | H | —C(=NH)H | H | CN | O | 2 |
| 109 | Me | H | —C(=NH)H | H | CH₂CN | O | 1 |
| 110 | Me | N | —C(=NH)H | H | (CH₂)₂CN | O | 2 |
| 111 | Me | H | —C(=NH)H | H | (CH₂)₂OH | O | 1 |

-continued

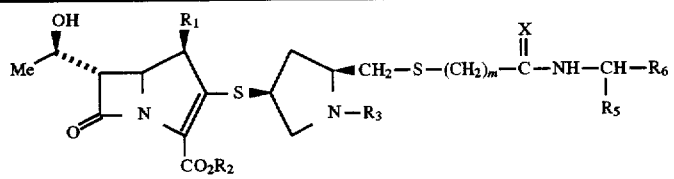

| No | R₁ | R₂ | R₃ | R₅ | R₆ | X | m |
|----|----|----|----|----|----|---|---|
| 112 | Me | H | −C(H)=NH | H | (CH₂)₂OH | O | 2 |
| 113 | Me | H | −C(H)=NH | H | (CH₂)₂CONH₂ | O | 1 |
| 114 | Me | H | −C(H)=NH | H | (CH₂)₂CONH₂ | O | 2 |
| 115 | Me | H | −C(CH₃)=NH | H | CN | O | 1 |
| 116 | Me | H | −C(CH₃)=NH | H | CN | O | 2 |
| 117 | Me | H | −C(CH₃)=NH | H | (CH₂)₂CN | O | 1 |
| 118 | Me | H | −C(CH₃)=NH | H | (CH₂)₂OH | O | 2 |
| 119 | Me | H | −C(CH₃)=NH | H | (CH₂)₂OH | O | 1 |
| 120 | Me | H | −C(CH₃)=NH | H | (CH₂)₂OH | O | 2 |
| 121 | Me | H | −C(CH₃)=NH | H | (CH₂)₂NH₂ | O | 1 |
| 122 | Me | H | −C(CH₃)=NH | H | (CH₂)₂NH₂ | O | 2 |
| 123 | Me | H | −C(CH₃)=NH | H | (CH₂)₂CONH₂ | O | 1 |
| 124 | Me | H | −C(CH₃)=NH | H | (CH₂)₂CONH₂ | O | 2 |
| 125 | Me | H | H | CH | CH₂OH | O | 1 |
| 126 | Me | H | H | CH | CH₂CN | O | 1 |
| 127 | Me | H | H | CH | CH₂NH₂ | O | 1 |
| 128 | Me | H | H | CH | CH₂OCONH₂ | O | 1 |
| 129 | Me | H | H | CH | CH₂CONH₂ | O | 1 |
| 130 | Me | H | H | CH | CH₂NHCONH₂ | O | 1 |
| 131 | Me | H | H | CH | CH₂CON(azetidinyl) | O | 1 |
| 132 | Me | H | H | CH | CH₂CON(azetidinyl) | O | 1 |
| 133 | Me | H | H | CH | CH₂CON(pyrrolidinyl) | O | 1 |

-continued

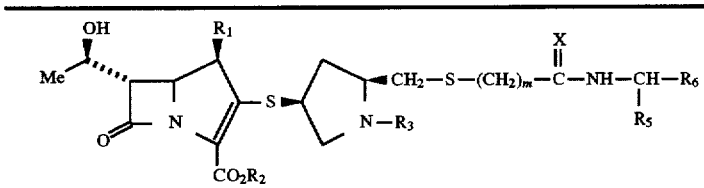

| No | R₁ | R₂ | R₃ | R₅ | R₆ | X | m |
|---|---|---|---|---|---|---|---|
| 134 | Me | H | H | CH | CH₂CON⟨piperidine⟩ | O | 1 |
| 135 | Me | H | H | CH | CH₂CON⟨pyrrolidine-2-CONH₂⟩ | O | 1 |
| 136 | Me | H | H | CH | CH₂CON⟨piperidine-4-CONH₂⟩ | O | 1 |
| 137 | Me | H | H | CH | CH₂CON⟨piperazine-NH⟩ | O | 1 |
| 138 | Me | H | H | CH | CH₂CON⟨piperazine-NCH₃⟩ | O | 1 |
| 139 | Me | anion | H | CH | CH₂CON⟨piperazine-N⁺(CH₃)₂⟩ | O | 1 |
| 140 | Me | H | H | CH | CH₂CON⟨piperazine-NCH₂OH⟩ | O | 1 |
| 141 | Me | H | H | CH | CH₂CON⟨piperazine-NCH₂CN⟩ | O | 1 |
| 142 | Me | H | H | CH | CH₂CON⟨piperazine-NCH₂NH₂⟩ | O | 1 |
| 143 | Me | H | H | CH | CH₂CON⟨piperazine-N(CH₂)₂OH⟩ | O | 1 |
| 144 | Me | H | H | CH | CH₂CON⟨piperazine-N(CH₂)₂NH₂⟩ | O | 1 |
| 145 | Me | H | H | CH | CH₂CON⟨piperazine-N(CH₂)₂CN⟩ | O | 1 |
| 146 | Me | H | H | CH | CH₂OH | O | 2 |

-continued

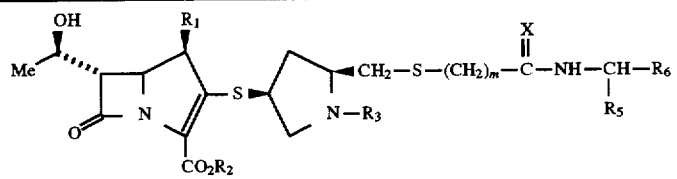

| No | $R_1$ | $R_2$ | $R_3$ | $R_5$ | $R_6$ | X | m |
|---|---|---|---|---|---|---|---|
| 147 | Me | H | H | CH | $CH_2CN$ | O | 2 |
| 148 | Me | H | H | CH | $CH_2NH_2$ | O | 2 |
| 149 | Me | H | H | CH | $CH_2CONH_2$ | O | 2 |
| 150 | Me | H | H | CH | $CH_2CONHCH_3$ | O | 2 |
| 151 | Me | H | H | CH | $CH_2CON(CH_3)_2$ | O | 2 |
| 152 | Me | H | H | CH | $CH_2OCONH_2$ | O | 2 |
| 153 | Me | H | H | CH | $CH_2NHCONH_2$ | O | 2 |
| 154 | Me | H | H | CH | $CH_2CON$◁ (aziridine) | O | 2 |
| 155 | Me | H | H | CH | $CH_2CON$ (azetidine) | O | 2 |
| 156 | Me | H | H | CH | $CH_2CON$ (pyrrolidine) | O | 2 |
| 157 | Me | H | H | CH | $CH_2CON$ (piperidine) | O | 2 |
| 158 | Me | H | H | CH | $CH_2CON$ (pyrrolidine-2-CONH$_2$) | O | 2 |
| 159 | Me | H | H | CH | $CH_2CON$ (piperidine-CONH$_2$) | O | 2 |
| 160 | Me | H | H | CH | $CH_2CON$ (piperazine NH) | O | 2 |
| 161 | Me | H | H | CH | $CH_2CON$ (piperazine NCH$_3$) | O | 2 |
| 162 | Me | anion | H | CH | $CH_2CON$ (piperazine N$^+$(CH$_3$)$_2$) | O | 2 |
| 163 | Me | H | H | CH | $CH_2CON$ (piperazine NCH$_2$OH) | O | 2 |
| 164 | Me | H | H | CH | $CH_2CON$ (piperazine NCH$_2$NH$_2$) | O | 2 |

-continued

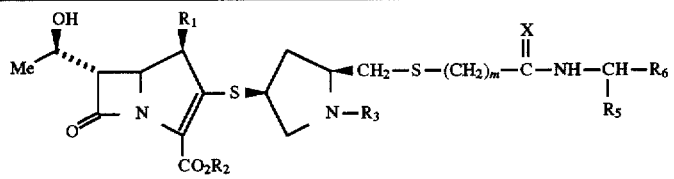

| No | R₁ | R₂ | R₃ | R₅ | R₆ | X | m |
|----|----|----|----|----|----|----|---|
| 165 | Me | H | H | CH | CH₂CON⟨⟩NCH₂CN | O | 2 |
| 166 | Me | H | H | CH | CH₂CON⟨⟩N(CH₂)₂OH | O | 2 |
| 167 | Me | H | H | CH | CH₂CON⟨⟩N(CH₂)₂NH₂ | O | 2 |
| 168 | Me | H | H | CH | CH₂CON⟨⟩N(CH₂)₂CN | O | 2 |
| 169 | Me | H | —C(H)=NH | CH | CH₂OH | O | 1 |
| 170 | Me | H | —C(H)=NH | CH | CH₂CN | O | 1 |
| 171 | Me | H | —C(H)=NH | CH | CH₂NH₂ | O | 1 |
| 172 | Me | H | —C(H)=NH | CH | CH₂CONH₂ | O | 1 |
| 173 | Me | H | —C(H)=NH | CH | CH₂OH | O | 2 |
| 174 | Me | H | —C(H)=NH | CH | CH₂CN | O | 2 |
| 175 | Me | H | —C(H)=NH | CH | CH₂NH₂ | O | 2 |
| 176 | Me | H | —C(H)=NH | CH | CH₂CONH₂ | O | 2 |
| 177 | Me | H | —C(H)=NH | CH | CH₂OCONH₂ | O | 2 |
| 178 | Me | H | —C(CH₃)=NH | CH | CH₂OH | O | 1 |
| 179 | Me | H | —C(CH₃)=NH | CH | CH₂CN | O | 1 |
| 180 | Me | H | —C(CH₃)=NH | CH | CH₂NH₂ | O | 1 |
| 181 | Me | H | —C(CH₃)=NH | CH | CH₂CONH₂ | O | 1 |

-continued

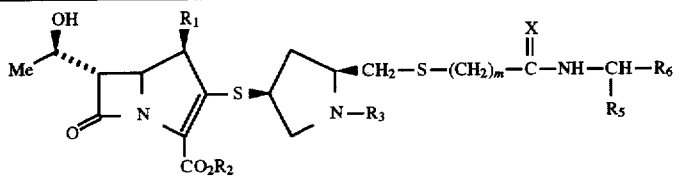

| No | R₁ | R₂ | R₃ | R₅ | R₆ | X | m |
|---|---|---|---|---|---|---|---|
| 182 | Me | H | −C(=NH)CH₃ | CH | CH₂OCONH₂ | O | 1 |
| 183 | Me | H | −C(=NH)CH₃ | CH | CH₂NH₂CONH₂ | O | 1 |
| 184 | Me | H | −C(=NH)CH₃ | CH | CH₂OH | O | 2 |
| 185 | Me | H | −C(=NH)CH₃ | CH | CH₂CN | O | 2 |
| 186 | Me | H | −C(=NH)CH₃ | CH | CH₂NH₂ | O | 2 |
| 187 | Me | H | −C(=NH)CH₃ | CH | CH₂CONH₂ | O | 2 |
| 188 | Me | H | −C(=NH)CH₃ | CH | CH₂OCONH₂ | O | 2 |
| 189 | Me | H | −C(=NH)CH₃ | CH | CH₂NHCONH₂ | O | 2 |
| 190 | Me | H | H | CN | CH₂OH | O | 1 |
| 191 | Me | H | H | CN | CH₂CN | O | 1 |
| 192 | Me | H | H | CN | CH₂NH₂ | O | 1 |
| 193 | Me | H | H | CN | CH₂CONH₂ | O | 1 |
| 194 | Me | H | H | CN | CH₂CONHCH₃ | O | 1 |
| 195 | Me | H | H | CN | CH₂CON(CH₃)₂ | O | 1 |
| 196 | Me | H | H | CN | CH₂OCONH₂ | O | 1 |
| 197 | Me | H | H | CN | CH₂NHCONH₂ | O | 1 |
| 198 | Me | H | H | CN | CH₂OH | O | 2 |
| 199 | Me | H | H | CN | CH₂CN | O | 2 |
| 200 | Me | H | H | CN | CH₂NH₂ | O | 2 |
| 201 | Me | H | H | CN | CH₂CONH₂ | O | 2 |
| 202 | Me | H | H | CN | CH₂CON(CH₃)₂ | O | 2 |
| 203 | Me | H | H | CN | CH₂CON(CH₃)₂ | O | 2 |
| 204 | Me | H | H | CN | CH₂NHCONH₂ | O | 2 |
| 205 | Me | H | H | CN | CH₂OCONH₂ | O | 2 |
| 206 | Me | H | H | CN | CH₂CON⟨aziridine⟩ | O | 1 |
| 207 | Me | H | H | CN | CH₂CON⟨azetidine⟩ | O | 1 |
| 208 | Me | H | H | CN | CH₂CON⟨pyrrolidine⟩ | O | 1 |
| 209 | Me | H | H | CN | CH₂CON⟨piperidine⟩ | O | 1 |

-continued

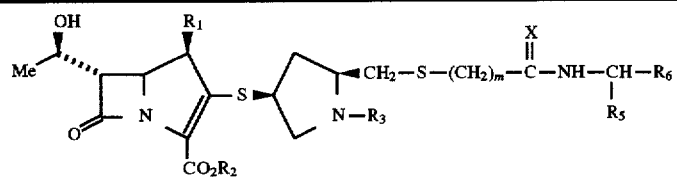

| No | R₁ | R₂ | R₃ | R₅ | R₆ | X | m |
|---|---|---|---|---|---|---|---|
| 210 | Me | H | H | CN | CH₂CON-[pyrrolidine with C(=O)NH₂] | O | 1 |
| 211 | Me | H | H | CN | CH₂CON-[piperidine with C(=O)NH₂] | O | 1 |
| 212 | Me | H | H | CN | CH₂CON-[piperazine NH] | O | 1 |
| 213 | Me | H | H | CN | CH₂CON-[piperazine NCH₃] | O | 1 |
| 214 | Me | anion | H | CN | CH₂CON-[piperazine N⁺(CH₃)₂] | O | 1 |
| 215 | Me | H | H | CN | CH₂CON-[piperazine NCH₂OH] | O | 1 |
| 216 | Me | H | H | CN | CH₂CON-[piperazine NCH₂CN] | O | 1 |
| 217 | Me | H | H | CN | CH₂CON-[piperazine NCH₂NH₂] | O | 1 |
| 218 | Me | H | H | CN | CH₂CON-[piperazine N(CH₂)₂OH] | O | 1 |
| 219 | Me | H | H | CN | CH₂CON-[piperazine N(CH₂)₂NH₂] | O | 1 |
| 220 | Me | H | H | CN | CH₂CON-[piperazine N(CH₂)₂CN] | O | 1 |
| 221 | Me | H | H | CN | CH₂CON-[aziridine] | O | 2 |
| 222 | Me | H | H | CN | CH₂CON-[azetidine] | O | 2 |

-continued

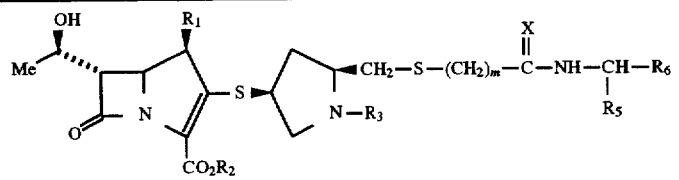

| No | $R_1$ | $R_2$ | $R_3$ | $R_5$ | $R_6$ | X | m |
|---|---|---|---|---|---|---|---|
| 223 | Me | H | H | CN | CH$_2$CON-pyrrolidine | O | 2 |
| 224 | Me | H | H | CN | CH$_2$CON-piperidine | O | 2 |
| 225 | Me | H | H | CN | CH$_2$CON-pyrrolidine-CONH$_2$ | O | 2 |
| 226 | Me | H | H | CN | CH$_2$CON-piperidine-CONH$_2$ | O | 2 |
| 227 | Me | H | H | CN | CH$_2$CON-piperazine NH | O | 2 |
| 228 | Me | H | H | CN | CH$_2$CON-piperazine NCH$_3$ | O | 2 |
| 229 | Me | anion | H | CN | CH$_2$CON-piperazine $N^+$(CH$_3$)$_2$ | O | 2 |
| 230 | Me | H | H | CN | CH$_2$CON-piperazine NCH$_2$OH | O | 2 |
| 231 | Me | H | H | CN | CH$_2$CON-piperazine NCH$_2$CN | O | 2 |
| 232 | Me | H | H | CN | CH$_2$CON-piperazine NCH$_2$NH$_2$ | O | 2 |
| 233 | Me | H | H | CN | CH$_2$CON-piperazine N(CH$_2$)$_2$OH | O | 2 |
| 234 | Me | H | H | CN | CH$_2$CON-piperazine N(CH$_2$)$_2$CN | O | 2 |

-continued

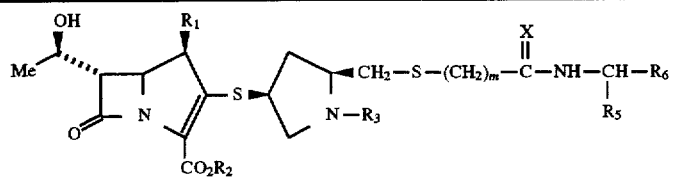

| No | $R_1$ | $R_2$ | $R_3$ | $R_5$ | $R_6$ | X | m |
|---|---|---|---|---|---|---|---|
| 235 | Me | H | H | CN | $CH_2CON\underset{\phantom{x}}{\overgroup{\phantom{xxxx}}}N(CH_2)_2NH_2$ | O | 2 |
| 236 | Me | H | H | $CH_2OH$ | $CH_2OH$ | O | 1 |
| 237 | Me | H | H | $CH_2OH$ | $CH_2CN$ | O | 1 |
| 238 | Me | H | H | $CH_2OH$ | $CH_2NH_2$ | O | 1 |
| 239 | Me | H | H | $CH_2OH$ | $CH_2OCONH_2$ | O | 1 |
| 240 | Me | H | H | $CH_2OH$ | $CH_2NHCONH_2$ | O | 1 |
| 241 | Me | H | H | $CH_2OH$ | $CH_2CONH_2$ | O | 1 |
| 242 | Me | H | H | $CH_2OH$ | $CH_2CONHCH_3$ | O | 1 |
| 243 | Me | H | H | $CH_2OH$ | $CH_2CON(CH_3)_2$ | O | 1 |
| 244 | Me | H | H | $CH_2OH$ | $CH_2OH$ | O | 2 |
| 245 | Me | H | H | $CH_2OH$ | $CH_2CN$ | O | 2 |
| 246 | Me | H | H | $CH_2OH$ | $CH_2NH_2$ | O | 2 |
| 247 | Me | H | H | $CH_2OH$ | $CH_2OCONH_2$ | O | 2 |
| 248 | Me | H | H | $CH_2OH$ | $CH_2NHCONH_2$ | O | 2 |
| 249 | Me | H | H | $CH_2OH$ | $CH_2CONH_2$ | O | 2 |
| 250 | Me | H | H | $CH_2OH$ | $CH_2CONHCH_3$ | O | 2 |
| 251 | Me | H | H | $CH_2OH$ | $CH_2CON(CH_3)_2$ | O | 2 |
| 252 | Me | H | H | $CH_2OH$ | $CH_2CH_2OH$ | O | 1 |
| 253 | Me | H | H | $CH_2OH$ | $CH_2CH_2CN$ | O | 1 |
| 254 | Me | H | H | $CH_2OH$ | $CH_2CH_2NH_2$ | O | 1 |
| 255 | Me | H | H | $CH_2OH$ | $CH_2CH_2CONH_2$ | O | 1 |
| 256 | Me | H | H | $CH_2OH$ | $CH_2CH_2NHCONH_2$ | O | 1 |
| 257 | Me | H | H | $CH_2OH$ | $CH_2CH_2OCONH_2$ | O | 1 |
| 258 | Me | H | H | $CH_2OH$ | $CH_2CH_2OH$ | O | 2 |
| 259 | Me | H | H | $CH_2OH$ | $CH_2CH_2CN$ | O | 2 |
| 260 | Me | H | H | $CH_2OH$ | $CH_2CH_2NH_2$ | O | 2 |
| 261 | Me | H | H | $CH_2OH$ | $CH_2CH_2OCONH_2$ | O | 2 |
| 262 | Me | H | H | $CH_2OH$ | $CH_2CH_2CONH_2$ | O | 2 |
| 263 | Me | H | H | $CH_2OH$ | $CH_2CH_2NHCONH_2$ | O | 1 |
| 264 | Me | H | H | $CH_2OH$ | $CH_2CON$-(cyclopropyl) | O | 1 |
| 265 | Me | H | H | $CH_2OH$ | $CH_2CON$-(cyclobutyl) | O | 1 |
| 266 | Me | H | H | $CH_2OH$ | $CH_2CON$-(pyrrolidinyl) | O | 1 |
| 267 | Me | H | H | $CH_2OH$ | $CH_2CON$-(piperidinyl) | O | 1 |
| 268 | Me | H | H | $CH_2OH$ | $CH_2CON$-(pyrrolidinyl-CONH$_2$) | O | 1 |
| 269 | Me | H | H | $CH_2OH$ | $CH_2CON$-(piperidinyl-CONH$_2$) | O | 1 |

-continued

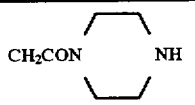

| No | R₁ | R₂ | R₃ | R₅ | R₆ | X | m |
|---|---|---|---|---|---|---|---|
| 270 | Me | H | H | $CH_2OH$ | $CH_2CON$⟨piperazine⟩$NH$ | O | 1 |
| 271 | Me | H | H | $CH_2OH$ | $CH_2CON$⟨piperazine⟩$NCH_3$ | O | 1 |
| 272 | Me | anion | H | $CH_2OH$ | $CH_2CON$⟨piperazine⟩$N^+(CH_3)_2$ | O | 1 |
| 273 | Me | H | H | $CH_2OH$ | $CH_2CON$⟨piperazine⟩$NCH_2OH$ | O | 1 |
| 274 | Me | H | H | $CH_2OH$ | $CH_2CON$⟨piperazine⟩$NCH_2CN$ | O | 1 |
| 275 | Me | H | H | $CH_2OH$ | $CH_2CON$⟨piperazine⟩$NCH_2NH_2$ | O | 1 |
| 276 | Me | H | H | $CH_2OH$ | $CH_2CON$⟨aziridine⟩ | O | 2 |
| 277 | Me | H | H | $CH_2OH$ | $CH_2CON$⟨azetidine⟩ | O | 2 |
| 278 | Me | H | H | $CH_2OH$ | $CH_2CON$⟨pyrrolidine⟩ | O | 2 |
| 279 | Me | H | H | $CH_2OH$ | $CH_2CON$⟨piperidine⟩ | O | 2 |
| 280 | Me | H | H | $CH_2OH$ | $CH_2CON$⟨pyrrolidine-CONH₂⟩ | O | 2 |
| 281 | Me | H | H | $CH_2OH$ | $CH_2CON$⟨piperidine-CONH₂⟩ | O | 2 |
| 282 | Me | H | H | $CH_2OH$ | $CH_2CON$⟨piperazine⟩$NH$ | O | 2 |

-continued

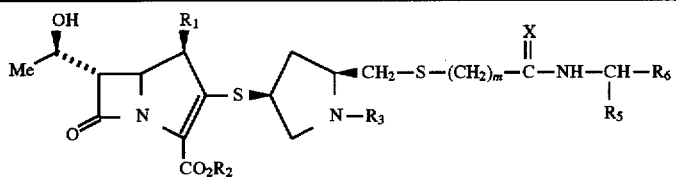

| No | $R_1$ | $R_2$ | $R_3$ | $R_5$ | $R_6$ | X | m |
|---|---|---|---|---|---|---|---|
| 283 | Me | H | H | $CH_2OH$ | $CH_2CON{\frown\atop\smile}NCH_3$ | O | 2 |
| 284 | Me | anion | H | $CH_2OH$ | $CH_2CON{\frown\atop\smile}\overset{+}{N}(CH_3)_2 / CH_3$ | O | 2 |
| 285 | Me | H | H | $CH_2OH$ | $CH_2CON{\frown\atop\smile}NCH_2OH$ | O | 2 |
| 286 | Me | H | H | $CH_2OH$ | $CH_2CON{\frown\atop\smile}NCH_2NH_2$ | O | 2 |
| 287 | Me | H | H | $CH_2OH$ | $CH_2CON{\frown\atop\smile}NCH_2CN$ | O | 2 |
| 288 | Me | H | —C(H)=NH | $CH_2OH$ | $CH_2OH$ | O | 1 |
| 289 | Me | H | —C(H)=NH | $CH_2OH$ | $CH_2CN$ | O | 1 |
| 290 | Me | H | —C(H)=NH | $CH_2OH$ | $CH_2NH_2$ | O | 1 |
| 291 | Me | H | —C(H)=NH | $CH_2OH$ | $CH_2OCONH_2$ | O | 1 |
| 292 | Me | H | —C(H)=NH | $CH_2OH$ | $CH_2CONH_2$ | O | 1 |
| 293 | Me | H | —C(H)=NH | $CH_2OH$ | $CH_2NHCONH_2$ | O | 1 |
| 294 | Me | H | —C(H)=NH | $CH_2OH$ | $CH_2OH$ | O | 2 |
| 295 | Me | H | —C(H)=NH | $CH_2OH$ | $CH_2CN$ | O | 2 |
| 296 | Me | H | —C(H)=NH | $CH_2OH$ | $CH_2NH_2$ | O | 2 |
| 297 | Me | H | —C(H)=NH | $CH_2OH$ | $CH_2OCONH_2$ | O | 2 |
| 298 | Me | H | —C(H)=NH | $CH_2OH$ | $CH_2NHCONH_2$ | O | 2 |

-continued

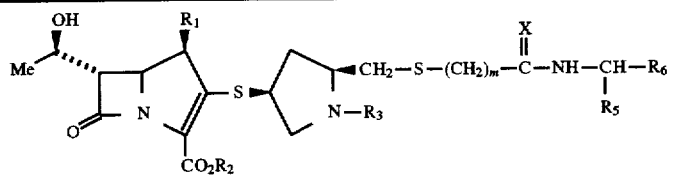

| No | R₁ | R₂ | R₃ | R₅ | R₆ | X | m |
|---|---|---|---|---|---|---|---|
| 299 | Me | H | −C(=NH)H | $CH_2OH$ | $CH_2CONH_2$ | O | 2 |
| 300 | Me | H | −C(=NH)H | $CH_2OH$ | $CH_2OH$ | O | 1 |
| 301 | Me | H | −C(=NH)CH₃ | $CH_2OH$ | $CH_2CN$ | O | 1 |
| 302 | Me | H | −C(=NH)CH₃ | $CH_2OH$ | $CH_2NH_2$ | O | 1 |
| 303 | Me | H | −C(=NH)CH₃ | $CH_2OH$ | $CH_2OCONH_2$ | O | 1 |
| 304 | Me | H | −C(=NH)CH₃ | $CH_2OH$ | $CH_2CONH_2$ | O | 1 |
| 305 | Me | H | −C(=NH)CH₃ | $CH_2OH$ | $CH_2NHCONH_2$ | O | 1 |
| 306 | Me | H | −C(=NH)CH₃ | $CH_2OH$ | $CH_2OH$ | O | 2 |
| 307 | Me | H | −C(=NH)CH₃ | $CH_2OH$ | $CH_2CN$ | O | 2 |
| 308 | Me | H | −C(=NH)CH₃ | $CH_2OH$ | $CH_2NH_2$ | O | 2 |
| 309 | Me | H | −C(=NH)CH₃ | $CH_2OH$ | $CH_2OCONH_2$ | O | 2 |
| 310 | Me | H | −C(=NH)CH₃ | $CH_2OH$ | $CH_2CONH_2$ | O | 2 |
| 311 | Me | H | −C(=NH)CH₃ | $CH_2OH$ | $CH_2NHCONH_2$ | O | 2 |
| 312 | Me | H | H | $CH_2CONH_2$ | $CH_2OH$ | O | 1 |
| 313 | Me | H | H | $CH_2CONH_2$ | $CH_2CN$ | O | 1 |
| 314 | Me | H | H | $CH_2CONH_2$ | $CH_2NH_2$ | O | 1 |
| 315 | Me | H | H | $CH_2CONH_2$ | $CH_2CONH_2$ | O | 1 |
| 316 | Me | H | H | $CH_2CONH_2$ | $CH_2NHCONH_2$ | O | 1 |
| 317 | Me | H | H | $CH_2CONH_2$ | $CH_2OCONH_2$ | O | 1 |
| 318 | Me | H | H | $CH_2CONH_2$ | $CH_2CON$⟨azetidinyl⟩ | O | 1 |
| 319 | Me | H | H | $CH_2CONH_2$ | $CH_2CON$⟨pyrrolidinyl-4⟩ | O | 1 |
| 320 | Me | H | H | $CH_2CONH_2$ | $CH_2CON$⟨pyrrolidinyl-5⟩ | O | 1 |

-continued

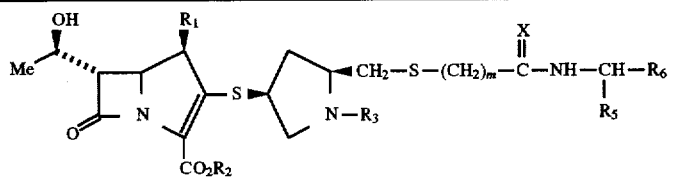

| No | $R_1$ | $R_2$ | $R_3$ | $R_5$ | $R_6$ | X | m |
|---|---|---|---|---|---|---|---|
| 321 | Me | H | H | $CH_2CONH_2$ | $CH_2CON$-(piperidinyl) | O | 1 |
| 322 | Me | H | H | $CH_2CONH_2$ | $CH_2CON$-(piperidinyl-CONH$_2$) | O | 1 |
| 323 | Me | H | H | $CH_2CONH_2$ | $CH_2CON$-(piperidinyl-CONH$_2$) | O | 1 |
| 324 | Me | H | H | $CH_2CONH_2$ | $CH_2CON$(piperazinyl-NH) | O | 1 |
| 325 | Me | H | H | $CH_2CONH_2$ | $CH_2CON$(piperazinyl-NCH$_3$) | O | 1 |
| 326 | Me | anion | H | $CH_2CONH_2$ | $CH_2CON$(piperazinyl-N$^+$(CH$_3$)$_2$) | O | 1 |
| 327 | Me | H | H | $CH_2CONH_2$ | $CH_2CON$(piperazinyl-NCH$_2$OH) | O | 1 |
| 328 | Me | H | H | $CH_2CONH_2$ | $CH_2CON$(piperazinyl-NCH$_2$NH$_2$) | O | 1 |
| 329 | Me | H | H | $CH_2CONH_2$ | $CH_2CON$(piperazinyl-NCH$_2$CN) | O | 1 |
| 330 | Me | H | H | $CH_2CONH_2$ | $CH_2CH_2OH$ | O | 1 |
| 331 | Me | H | H | $CH_2CONH_2$ | $CH_2CH_2CN$ | O | 1 |
| 332 | Me | H | H | $CH_2CONH_2$ | $CH_2CH_2NH_2$ | O | 1 |
| 333 | Me | H | H | $CH_2CONH_2$ | $CH_2CH_2CONH_2$ | O | 1 |
| 334 | Me | H | H | $CH_2CONH_2$ | $CH_2CH_2OCONH_2$ | O | 1 |
| 335 | Me | H | H | $CH_2CONH_2$ | $CH_2CH_2NHCONH_2$ | O | 1 |
| 336 | Me | H | H | $CH_2CONH_2$ | $CH_2OH$ | O | 2 |
| 337 | Me | H | H | $CH_2CONH_2$ | $CH_2CN$ | O | 2 |
| 338 | Me | H | H | $CH_2CONH_2$ | $CH_2NH_2$ | O | 2 |
| 339 | Me | H | H | $CH_2CONH_2$ | $CH_2OCONH_2$ | O | 2 |
| 340 | Me | H | H | $CH_2CONH_2$ | $CH_2CONH_2$ | O | 2 |
| 341 | Me | H | H | $CH_2CONH_2$ | $CH_2NHCONH_2$ | O | 2 |
| 342 | Me | H | H | $CH_2CONH_2$ | $CH_2CON$(aziridinyl) | O | 2 |

-continued

| No | $R_1$ | $R_2$ | $R_3$ | $R_5$ | $R_6$ | X | m |
|---|---|---|---|---|---|---|---|
| 343 | Me | H | H | $CH_2CONH_2$ |  | O | 2 |
| 344 | Me | H | H | $CH_2CONH_2$ |  | O | 2 |
| 345 | Me | H | H | $CH_2CONH_2$ |  | O | 2 |
| 346 | Me | H | H | $CH_2CONH_2$ |  | O | 2 |
| 347 | Me | H | H | $CH_2CONH_2$ |  | O | 2 |
| 348 | Me | H | H | $CH_2CONH_2$ |  | O | 2 |
| 349 | Me | H | H | $CH_2CONH_2$ |  | O | 2 |
| 350 | Me | anion | H | $CH_2CONH_2$ |  | O | 2 |
| 351 | Me | H | H | $CH_2CONH_2$ |  | O | 2 |
| 352 | Me | H | H | $CH_2CONH_2$ |  | O | 2 |
| 353 | Me | H | H | $CH_2CONH_2$ |  | O | 2 |
| 354 | Me | H | H | $CH_2CONH_2$ | $CH_2CH_2OH$ | O | 2 |
| 355 | Me | H | H | $CH_2CONH_2$ | $CH_2CH_2CN$ | O | 2 |
| 356 | Me | H | H | $CH_2CONH_2$ | $CH_2CH_2NH_2$ | O | 2 |
| 357 | Me | H | H | $CH_2CONH_2$ | $CH_2CH_2OCONH_2$ | O | 2 |
| 358 | Me | H | H | $CH_2CONH_2$ | $CH_2CH_2NHCONH_2$ | O | 2 |
| 359 | Me | H | H | $CH_2CONH_2$ | $CH_2CH_2CONH_2$ | O | 2 |
| 360 | Me | H | H | $CH_2CONH_2$ | $CH_2CH_2CONHCH_3$ | O | 2 |

-continued

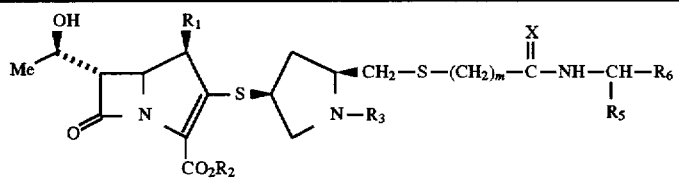

| No | $R_1$ | $R_2$ | $R_3$ | $R_5$ | $R_6$ | X | m |
|---|---|---|---|---|---|---|---|
| 361 | Me | H | H | $CH_2CONH_2$ | $CH_2CH_2CON(CH_3)_2$ | O | 2 |
| 362 | Me | H | −C(=NH)H | $CH_2CONH_2$ | $CH_2OH$ | O | 1 |
| 363 | Me | H | −C(=NH)H | $CH_2CONH_2$ | $CH_2NH_2$ | O | 1 |
| 364 | Me | H | −C(=NH)H | $CH_2CONH_2$ | $CH_2CN$ | O | 1 |
| 365 | Me | H | −C(=NH)H | $CH_2CONH_2$ | $CH_2OCONH_2$ | O | 1 |
| 366 | Me | H | −C(=NH)H | $CH_2CONH_2$ | $CH_2CONH_2$ | O | 1 |
| 367 | Me | H | −C(=NH)H | $CH_2CONH_2$ | $CH_2NHCONH_2$ | O | 1 |
| 368 | Me | H | −C(=NH)H | $CH_2CONH_2$ | $CH_2OH$ | O | 2 |
| 369 | Me | H | −C(=NH)H | $CH_2CONH_2$ | $CH_2NH_2$ | O | 2 |
| 370 | Me | H | −C(=NH)H | $CH_2CONH_2$ | $CH_2CN$ | O | 2 |
| 371 | Me | H | −C(=NH)H | $CH_2CONH_2$ | $CH_2CONH_2$ | O | 2 |
| 372 | Me | H | −C(=NH)H | $CH_2CONH_2$ | $CH_2NHCONH_2$ | O | 2 |
| 373 | Me | H | −C(=NH)$CH_3$ | $CH_2CONH_2$ | $CH_2OH$ | O | 1 |
| 374 | Me | H | −C(=NH)$CH_3$ | $CH_2CONH_2$ | $CH_2CN$ | O | 1 |
| 375 | Me | H | −C(=NH)$CH_3$ | $CH_2CONH_2$ | $CH_2NH_2$ | O | 1 |
| 376 | Me | H | −C(=NH)$CH_3$ | $CH_2CONH_2$ | $CH_2OCONH_2$ | O | 1 |
| 377 | Me | H | −C(=NH)$CH_3$ | $CH_2CONH_2$ | $CH_2CH_2NHCONH_2$ | O | 1 |
| 378 | Me | H | −C(=NH)$CH_3$ | $CH_2CONH_2$ | $CH_2CH_2CONH_2$ | O | 1 |
| 379 | Me | H | −C(=NH)$CH_3$ | $CH_2CONH_2$ | $CH_2CH_2CONHCH_3$ | O | 2 |

-continued

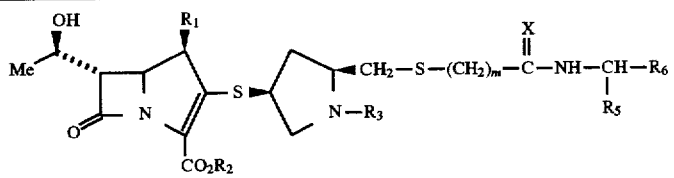

| No | $R_1$ | $R_2$ | $R_3$ | $R_5$ | $R_6$ | X | m |
|---|---|---|---|---|---|---|---|
| 280 | Me | H | −C(CH$_3$)=NH | CH$_2$CONH$_2$ | CH$_2$CH$_2$CON(CH$_3$)$_2$ | O | 2 |
| 381 | Me | H | −C(CH$_3$)=NH | CH$_2$CONH$_2$ | CH$_2$OH | O | 2 |
| 382 | Me | H | −C(CH$_3$)=NH | CH$_2$CONH$_2$ | CH$_2$NH$_2$ | O | 2 |
| 383 | Me | H | −C(CH$_3$)=NH | CH$_2$CONH$_2$ | CH$_2$CN | O | 2 |
| 384 | Me | H | −C(CH$_3$)=NH | CH$_2$CONH$_2$ | CH$_2$OCONH$_2$ | O | 2 |
| 385 | Me | H | −C(CH$_3$)=NH | CH$_2$CONH$_2$ | CH$_2$CONH$_2$ | O | 2 |

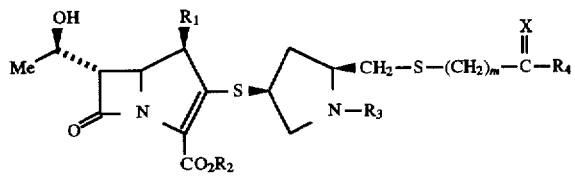

| No | $R_1$ | $R_2$ | $R_3$ | $R_4$ | X | m |
|---|---|---|---|---|---|---|
| 386 | Me | H | H | NHCH$_3$ | O | 1 |
| 387 | Me | H | H | NH$_2$ | O | 2 |
| 388 | Me | H | H | NHCH$_3$ | O | 2 |
| 389 | Me | H | H | N(CH$_3$)$_2$ | O | 1 |
| 390 | Me | H | H | MeNEt | O | 1 |
| 391 | Me | H | H | MeNiPr | O | 1 |
| 392 | Me | H | H | EtNiPr | O | 1 |
| 393 | Me | H | H | N(iPr)$_2$ | O | 1 |
| 394 | Me | H | H | MeNEt | O | 2 |
| 395 | Me | H | H | N(Et)$_2$ | O | 2 |
| 396 | Me | H | H | EtNiPr | O | 2 |
| 397 | Me | H | H | N(iPr)$_2$ | O | 2 |
| 398 | Me | H | −C(H)=NH | N(iPr)$_2$ | O | 1 |
| 399 | Me | H | −C(H)=NH | NHCH$_3$ | O | 2 |
| 400 | Me | H | −C(H)=NH | NH$_2$ | O | 2 |
| 401 | Me | H | −C(CH$_3$)=NH | NHCH$_3$ | O | 1 |
| 402 | Me | H | −C(CH$_3$)=NH | NH$_2$ | O | 2 |

-continued
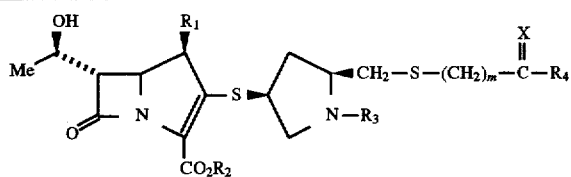
| No | $R_1$ | $R_2$ | $R_3$ | $R_4$ | X | m |
|---|---|---|---|---|---|---|
| 403 | Me | H | −C(CH₃)=NH | NHCH₃ | O | 2 |
| 404 | Me | H | H | aziridin-1-yl | O | 1 |
| 405 | Me | H | H | azetidin-1-yl | O | 1 |
| 406 | Me | H | H | pyrrolidin-1-yl | O | 1 |
| 407 | Me | H | H | piperidin-1-yl | O | 1 |
| 408 | Me | H | H | 2-carbamoylpyrrolidin-1-yl | O | 1 |
| 409 | Me | H | H | 3-carbamoylpiperidin-1-yl | O | 1 |
| 410 | Me | H | H | aziridin-1-yl | O | 2 |
| 411 | Me | H | H | azetidin-1-yl | O | 2 |
| 412 | Me | H | H | pyrrolidin-1-yl | O | 2 |
| 413 | Me | H | H | piperidin-1-yl | O | 2 |
| 414 | Me | H | H | 2-carbamoylpyrrolidin-1-yl | O | 2 |

-continued

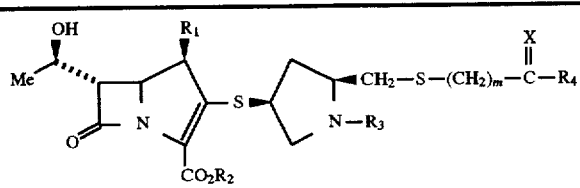

| No | $R_1$ | $R_2$ | $R_3$ | $R_4$ | X | m |
|---|---|---|---|---|---|---|
| 415 | Me | H | H | 3-carbamoyl-piperidin-1-yl | O | 2 |
| 416 | Me | H | —C(=NH)H | 2-carbamoyl-pyrrolidin-1-yl | O | 1 |
| 417 | Me | H | —C(=NH)H | 3-carbamoyl-piperidin-1-yl | O | 1 |
| 418 | Me | H | —C(=NH)H | 2-carbamoyl-pyrrolidin-1-yl | O | 2 |
| 419 | Me | H | —C(=NH)H | 3-carbamoyl-piperidin-1-yl | O | 2 |
| 420 | Me | H | —C(=NH)CH$_3$ | 2-carbamoyl-pyrrolidin-1-yl | O | 1 |
| 421 | Me | H | —C(=NH)CH$_3$ | 3-carbamoyl-piperidin-1-yl | O | 1 |
| 422 | Me | H | —C(=NH)CH$_3$ | 2-carbamoyl-pyrrolidin-1-yl | O | 2 |
| 423 | Me | H | —C(=NH)CH$_3$ | 3-carbamoyl-piperidin-1-yl | O | 2 |
| 424 | Me | H | H | piperazin-1-yl | O | 1 |

-continued
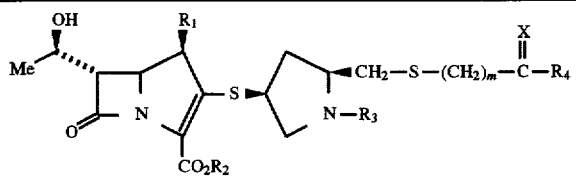
| No | R₁ | R₂ | R₃ | R₄ | X | m |
|---|---|---|---|---|---|---|
| 425 | Me | H | H | N⌒NCH₃ (piperazine) | O | 1 |
| 426 | Me | H | H | N⌒NCH₂OH | O | 1 |
| 427 | Me | H | H | N⌒NCH₂CN | O | 1 |
| 428 | Me | H | H | N⌒NCH₂NH₂ | O | 1 |
| 429 | Me | H | H | N⌒NCH₂OCONH₂ | O | 1 |
| 430 | Me | H | H | N⌒NCH₂NHCONH₂ | O | 1 |
| 431 | Me | H | H | N⌒NCH₂CONH₂ | O | 1 |
| 432 | Me | H | H | N⌒NCH₂CONHCH₃ | O | 1 |
| 433 | Me | H | H | N⌒NCH₂CON(CH₃)₂ | O | 1 |
| 434 | Me | H | H | N⌒NH | O | 2 |
| 435 | Me | H | H | N⌒NCH₃ | O | 2 |
| 436 | Me | H | H | N⌒NCH₂OH | O | 2 |
| 437 | Me | H | H | N⌒NCH₂CN | O | 2 |

-continued
| No | R₁ | R₂ | R₃ | R₄ | X | m |
|---|---|---|---|---|---|---|
| 438 | Me | H | H | N⌒N-CH₂NH₂ (piperazine) | O | 2 |
| 439 | Me | H | H | N⌒N-CH₂OC(=O)NH₂ | O | 2 |
| 440 | Me | H | H | N⌒N-CH₂NHC(=O)NH₂ | O | 2 |
| 441 | Me | H | H | N⌒N-CH₂C(=O)NH₂ | O | 2 |
| 442 | Me | H | H | N⌒N-CH₂C(=O)NHCH₃ | O | 2 |
| 443 | Me | H | H | N⌒N-CH₂C(=O)N(CH₃)₂ | O | 2 |
| 444 | Me | H | H | N⌒N-CH₂CH₂OH | O | 1 |
| 445 | Me | H | H | N⌒N-CH₂CH₂CN | O | 1 |
| 446 | Me | H | H | N⌒N-CH₂CH₂OC(=O)NH₂ | O | 1 |
| 447 | Me | H | H | N⌒N-CH₂CH₂NH₂ | O | 1 |
| 448 | Me | H | H | N⌒N-CH₂CH₂NHC(=O)NH₂ | O | 1 |
| 449 | Me | H | H | N⌒N-CH₂CH₂C(=O)NH₂ | O | 1 |

-continued

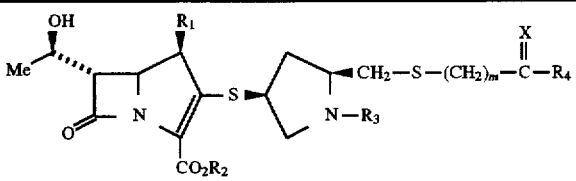

| No | R₁ | R₂ | R₃ | R₄ | X | m |
|---|---|---|---|---|---|---|
| 450 | Me | H | H | ⟨N⟩NCH₂CH₂C(=O)NHCH₃ | O | 1 |
| 451 | Me | H | H | ⟨N⟩NCH₂CH₂C(=O)N(CH₃)₂ | O | 1 |
| 452 | Me | H | H | ⟨N⟩NCH₂CH₂OH | O | 2 |
| 453 | Me | H | H | ⟨N⟩NCH₂CH₂CN | O | 2 |
| 454 | Me | H | H | ⟨N⟩NCH₂CH₂OC(=O)NH₂ | O | 2 |
| 455 | Me | H | H | ⟨N⟩NCH₂CH₂NH₂ | O | 2 |
| 456 | Me | H | H | ⟨N⟩NCH₂CH₂C(=O)NH₂ | O | 2 |
| 457 | Me | H | H | ⟨N⟩NCH₂CH₂C(=O)N(CH₃)₂ | O | 2 |
| 458 | Me | H | H | ⟨N⟩NCH₂CH₂C(=O)N(CH₃)₂ | O | 2 |
| 459 | Me | H | −C(H)=NH | ⟨N⟩NCH₂CH₂OH | O | 1 |
| 460 | Me | H | −C(H)=NH | ⟨N⟩NCH₂CH₂CN | O | 1 |
| 461 | Me | H | −C(H)=NH | ⟨N⟩NCH₂CH₂C(=O)NHCH₃ | O | 1 |
| 462 | Me | H | −C(H)=NH | ⟨N⟩N(CH₂)₂CH₂C(=O)NHCH₃ | O | 1 |

-continued

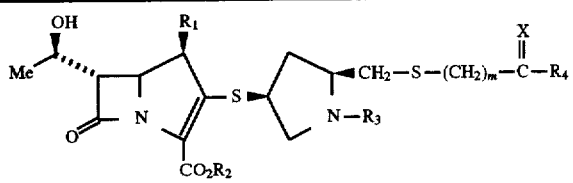

| No | R₁ | R₂ | R₃ | R₄ | X | m |
|---|---|---|---|---|---|---|
| 463 | Me | H | —C(H)=NH | [piperazine]-NCH₂CH₂NHC(=O)NH₂ | O | 1 |
| 464 | Me | H | —C(CH₃)=NH | [piperazine]-NCH₂CH₂OH | O | 1 |
| 465 | Me | H | —C(CH₃)=NH | [piperazine]-NCH₂CH₂CN | O | 1 |
| 466 | Me | H | —C(CH₃)=NH | [piperazine]-NCH₂CH₂OC(=O)NH₂ | O | 1 |
| 467 | Me | H | —C(CH₃)=NH | [piperazine]-NCH₂CH₂C(=O)NH₂ | O | 1 |
| 468 | Me | H | —C(CH₃)=NH | [piperazine]-NCH₂CH₂NHC(=O)NH₂ | O | 1 |
| 469 | Me | H | —C(H)=NH | [piperazine]-NCH₂CH₂OH | O | 2 |
| 470 | Me | H | —C(H)=NH | [piperazine]-NCH₂CH₂CN | O | 2 |
| 471 | Me | H | —C(H)=NH | [piperazine]-NCH₂CH₂OC(=O)NH₂ | O | 2 |
| 472 | Me | H | —C(H)=NH | [piperazine]-NCH₂CH₂C(=O)NH₂ | O | 2 |
| 473 | Me | H | —C(H)=NH | [piperazine]-N(CH₂)₂CH₂C(=O)NH₂ | O | 2 |
| 474 | Me | H | —C(CH₃)=NH | [piperazine]-NCH₂CH₂OH | O | 2 |

-continued

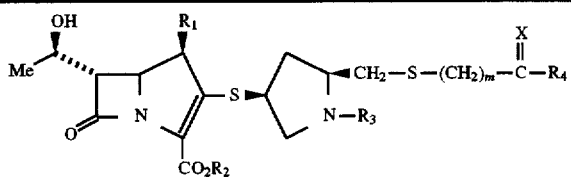

| No | R₁ | R₂ | R₃ | R₄ | X | m |
|---|---|---|---|---|---|---|
| 475 | Me | H | $-\underset{CH_3}{\underset{|}{C}}=NH$ | ⌬N-NCH₂CH₂CN | O | 2 |
| 476 | Me | H | $-\underset{CH_3}{\underset{|}{C}}=NH$ | ⌬N-NCH₂CH₂OCNH₂ (C=O) | O | 2 |
| 477 | Me | H | $-\underset{CH_3}{\underset{|}{C}}=NH$ | ⌬N-NCH₂CH₂CNH₂ (C=O) | O | 2 |
| 478 | Me | H | $-\underset{CH_3}{\underset{|}{C}}=NH$ | ⌬N-NCH₂CH₂NHCNH₂ (C=O) | O | 2 |
| 479 | Me | H | H | NH₂ | NH | 1 |
| 480 | Me | H | H | NHCH₃ | NH | 1 |
| 481 | Me | H | H | N(CH₃)₂ | NH | 1 |
| 482 | Me | H | H | MeNEt | NH | 1 |
| 483 | Me | H | H | N(Et)₂ | NH | 1 |
| 484 | Me | H | H | NH₂ | NH | 2 |
| 485 | Me | H | H | NHCH₃ | NH | 2 |
| 486 | Me | H | H | N(CH₃)₂ | NH | 2 |
| 487 | Me | H | H | MeNEt | NH | 2 |
| 488 | Me | H | H | N(Et)₂ | NH | 2 |
| 489 | Me | H | H | EtNiPr | NH | 2 |
| 490 | Me | H | H | N(iPr)₂ | NH | 2 |
| 491 | Me | H | H | N-aziridinyl | NH | 2 |
| 492 | Me | H | H | N-azetidinyl | NH | 2 |
| 493 | Me | H | H | N-pyrrolidinyl | NH | 2 |
| 494 | Me | H | H | N-piperidinyl | NH | 2 |
| 495 | Me | H | H | 2-carbamoyl-pyrrolidin-1-yl | NH | 2 |
| 496 | Me | H | H | 3-carbamoyl-piperidin-1-yl | NH | 2 |

-continued

[Structure: carbapenem with OH, R₁, CH₂-S-(CH₂)ₘ-C(=X)-R₄, CO₂R₂, N-R₃]

| No | R₁ | R₂ | R₃ | R₄ | X | m |
|---|---|---|---|---|---|---|
| 497 | Me | H | H | piperazinyl-NCH₂CH₂OH | NH | 2 |
| 498 | Me | H | H | piperazinyl-NCH₂CH₂CN | NH | 2 |
| 499 | Me | H | H | piperazinyl-NCH₂CH₂NH₂ | NH | 2 |
| 500 | Me | H | H | piperazinyl-NCH₂CH₂OC(=O)NH₂ | NH | 2 |
| 501 | Me | H | H | piperazinyl-NCH₂CH₂C(=O)NH₂ | NH | 2 |
| 502 | Me | H | H | piperazinyl-NCH₂CH₂NHC(=O)NH₂ | NH | 2 |
| 503 | Me | H | H | piperazinyl-NCH₂CH₂C(=O)NHCH₃ | NH | 2 |
| 504 | Me | H | H | piperazinyl-NCH₂CH₂C(=O)N(CH₃)₂ | NH | 2 |

-continued

[Structure: carbapenem with OH, R₁, CH₂-S-(CH₂)ₘ-R₉, CO₂R₂, N-R₃]

| No | R₁ | R₂ | R₃ | R₉ | m |
|---|---|---|---|---|---|
| 505 | Me | H | H | OH | 1 |
| 506 | Me | H | H | OH | 2 |
| 507 | Me | H | H | OH | 3 |
| 508 | Me | H | H | OH | 4 |
| 509 | Me | H | H | OH | 5 |
| 510 | Me | H | H | OH | 6 |
| 511 | Me | H | H | CH(OH)CH₃ | 1 |
| 512 | Me | H | H | CH(OH)₂ | 1 |
| 513 | Me | H | H | CH(OH)CH₃ | 2 |
| 514 | Me | H | H | CH(OH)₂ | 2 |
| 515 | Me | H | H | CH(OH)CH₃ | 3 |
| 516 | Me | H | H | CH(OH)₂CH₃ | 3 |
| 517 | Me | H | H | CH(OH)CH₃ | 4 |
| 518 | Me | H | H | CH(OH)₂ | 4 |
| 519 | Me | H | —C(=NH)H | OH | 1 |
| 520 | Me | H | —C(=NH)H | OH | 2 |

-continued

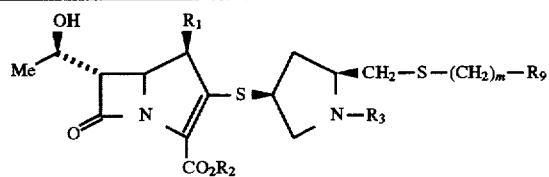

| No | R₁ | R₂ | R₃ | R₉ | m |
|---|---|---|---|---|---|
| 521 | Me | H | —C(=NH)H | OH | 3 |
| 522 | Me | H | —C(=NH)H | OH | 4 |
| 523 | Me | H | —C(=NH)H | OH | 5 |
| 524 | Me | H | —C(=NH)CH₃ | OH | 1 |
| 525 | Me | H | —C(=NH)CH₃ | OH | 2 |
| 526 | Me | H | —C(=NH)CH₃ | OH | 3 |
| 527 | Me | H | —C(=NH)CH₃ | OH | 4 |
| 528 | Me | H | H | OCONH₂ | 1 |
| 529 | Me | H | H | OCONH₂ | 2 |
| 530 | Me | H | H | OCONH₂ | 3 |
| 531 | Me | H | H | OCONH₂ | 4 |
| 532 | Me | H | H | OCONH₂ | 5 |
| 533 | Me | H | H | OCONH₂ | 6 |
| 534 | Me | H | —C(=NH)H | OCONH₂ | 1 |
| 535 | Me | H | —C(=NH)H | OCONH₂ | 2 |
| 536 | Me | H | —C(=NH)H | OCONH₂ | 3 |
| 537 | Me | H | —C(=NH)H | OCONH₂ | 4 |
| 538 | Me | H | —C(=NH)CH₃ | OCONH₂ | 1 |
| 539 | Me | H | —C(=NH)CH₃ | OCONH₂ | 2 |
| 540 | Me | H | —C(=NH)CH₃ | OCONH₂ | 3 |
| 541 | Me | H | —C(=NH)CH₃ | OCONH₂ | 4 |

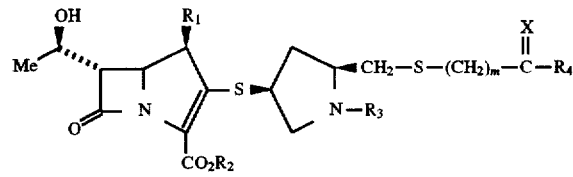

| No | R₁ | R₂ | R₃ | R₄ | X | m |
|---|---|---|---|---|---|---|
| 542 | Me | H | H | CH₂OH | O | 1 |
| 543 | Me | H | H | (CH₂)₂OH | O | 1 |
| 544 | Me | H | H | (CH₂)₂OH | O | 1 |
| 545 | Me | H | H | (CH₂)₂OH | O | 1 |
| 546 | Me | H | H | CH₂CH | O | 2 |
| 547 | Me | H | H | (CH₂)₂OH | O | 2 |
| 548 | Me | H | H | (CH₂)₃OH | O | 2 |
| 549 | Me | H | H | (CH₂)₄OH | O | 2 |
| 550 | Me | H | —C(=NH)H | (CH₂)₂OH | O | 1 |
| 551 | Me | H | —C(=NH)CH₃ | (CH₂)₂OH | O | 1 |
| 552 | Me | H | —C(=NH)H | (CH₂)₄OH | O | 2 |
| 553 | Me | H | —C(=NH)CH₃ | (CH₂)₄OH | O | 2 |
| 554 | Me | H | H | (CH₂)₄OCH₃ | O | 1 |
| 555 | Me | H | H | (CH₂)₂OCONH₂ | O | 1 |
| 556 | Me | H | H | (CH₂)₃OCONH₂ | O | 1 |
| 557 | Me | H | H | (CH₂)₄OCONH₂ | O | 1 |
| 558 | Me | H | H | CH₂OCONH₂ | O | 2 |
| 559 | Me | H | H | (CH₂)₂OCONH₂ | O | 2 |
| 560 | Me | H | H | (CH₂)₃OCONH₂ | O | 2 |
| 561 | Me | H | H | (CH₂)₄OCONH₂ | O | 2 |
| 562 | Me | H | —C(=NH)H | (CH₂)₂OCONH₂ | O | 2 |
| 563 | Me | H | —C(=NH)H | (CH₂)₃OCONH₂ | O | 2 |
| 564 | Me | H | —C(=NH)H | (CH₂)₄OCONH₂ | O | 2 |
| 565 | Me | H | —C(=NH)CH₃ | (CH₂)₂OCONH₂ | O | 2 |
| 566 | Me | H | —C(=NH)CH₃ | (CH₂)₃OCONH₂ | O | 2 |
| 567 | Me | H | —C(=NH)CH₃ | (CH₂)₄OCONH₂ | O | 2 |
| 568 | H | H | H | CH₂OH | O | 1 |
| 569 | H | H | H | (CH₂)₂OH | O | 1 |
| 570 | H | H | H | (CH₂)₃OH | O | 1 |
| 571 | H | H | H | (CH₂)₄OH | O | 1 |
| 572 | H | H | H | (CH₂)₂OH | O | 2 |
| 573 | H | H | H | (CH₂)₂OH | O | 2 |
| 574 | H | H | H | (CH₂)₃OH | O | 2 |
| 575 | H | H | H | (CH₂)₄OH | O | 2 |
| 576 | H | H | H | (CH₂)₂OCONH₂ | O | 1 |
| 577 | H | H | H | (CH₂)₃OCONH₂ | O | 1 |
| 578 | H | H | H | (CH₂)₄OCONH₂ | O | 1 |
| 579 | H | H | H | (CH₂)₂OCONH₂ | O | 2 |
| 580 | H | H | H | (CH₂)₃OCONH₂ | O | 2 |

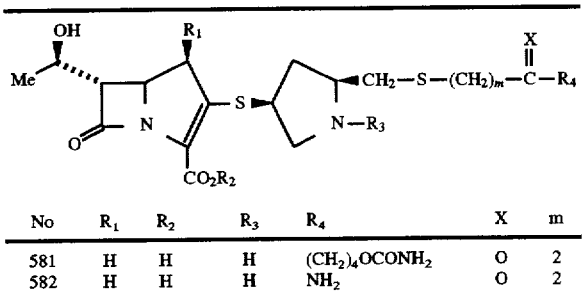

| No  | R₁ | R₂ | R₃ | R₄          | X | m |
|-----|----|----|----|-------------|---|---|
| 581 | H  | H  | H  | (CH₂)₄OCONH₂ | O | 2 |
| 582 | H  | H  | H  | NH₂         | O | 2 |

Reference Example 1

44.6 g of 2-amino-2-methyl-1-propanol, 65 g of diethylcarbonate and 7 g of potassium carbonate were mixed and stirred while heating at 120° C. to 140° C., and then methanol produced during the reaction was removed with a water-trapping apparatus. The reaction solution was concentrated and then allowed to stand in a refrigerator to obtain a white precipitate. The resulting product was dissolved in ethyl ether and filtered to remove the insoluble materials. The filtrate was concentrated and then allowed to stand under ice-cooling to obtain a white solid which is then filtered and dried to obtain 25.7 g of the desired product 4,4-dimethyl-oxazolidin-2-one.

Melting Point: 52°–53° C. $^1$H NMR(DCCl₃) δ: 1.35 (s, 6H, 2CH₃), 4.00 (s, 2H, CH₂), 6.70 (bs, 1H, NH₁)

Reference Example 2

11.5 g of the compound prepared in Reference Example 1 was dissolved in 200 ml of anhydrous tetrahydrofuran and the resulting solution was cooled to −50° C. to −60° C. and 70 ml of n-butyl lithium was slowly added thereto under nitrogen atmosphere. At the same temperature 22 g of 2-bromopropionyl bromide was added dropwise thereto under stirring. After stirring for one hour at the same temperature, the reaction mixture was slowly warmed to 0° C. and then stirred for one hour. The reaction mixture was diluted with water and then extracted with ethyl ether. The organic layer was combined, dried and concentrated under reduced pressure to obtain 18 g of the desired product 3-(2-bromopropionyl)-4,4-dimethyl-oxazolidin-2-one.

$^1$H NMR(DCCl₃) δ: 1.60 (s, 6H, 2CH₃), 1.82 (d, 3H, CH₃), 4.05 (s, 2H, CH₂), 5.80 (q, 1H, CH, CH₃)

Reference Example 3

0.59 g of azetinone and 0.5 g of activated zinc were added to 40 ml of anhydrous tetrahydrofuran. 1.06 g of the compound prepared in Reference Example 2 was added dropwise thereto while heating under reflux and then the reaction mixture was heated for further 30 minutes under reflux. Saturated ammonium chloride solution was added to the mixture to complete the reaction. Ethyl acetate was added to the mixture to extract the reaction product and the extracted organic layers were combined, washed with distilled water, dried and concentrated under reduced pressure to obtain 470 mg of the desired product (3S,4S)-3-(1R-t-butyldimethylsilyloxyethyl)-4-[(1R"-1-carboxyethyl)-2-(4", 4"-dimethyl-2"-oxazolidinoyl)]azetidin-2-one.

Melting Point: 171°–172° C. $^1$H NMR(DCCl₃) δ: 0.07 (s, 3H), 0.08 (s, 3H), 0.87 (s, 9H), 1.19 (d, 3H, J=6 Hz), 1.21 (d, 3H, J=6 Hz), 1.58 (s, 6H), 3.01–3.04 (s, 1H), 3.90–3.95 (m,1H), 4.14–4.23 (m, 2H), 6.00 (s, 1H, NH)

Reference Example 4

5.1 g of the compound prepared in Reference Example 3 was dissolved in 200 ml of tetrahydrofuran and then 3.5 ml of 30% hydrogen peroxide was added thereto. Then, 1N-sodium hydroxide solution was slowly added dropwise to the reaction mixture with stirring at 5° to 10° C. The whole reaction mixture was stirred for 30 minutes at the same temperature, evaporated under reduced pressure to remove tetrahydrofuran solvent and extracted with ethyl acetate. The extract was adjusted to pH 3 to 4 by adding 10% hydrochloric acid solution and evaporated under reduced pressure to remove the solvent to obtain 2.6 g of the white desired product (3S,4S)-3-[(1R-t-butyldimethylsilyloxyethyl)-4-(1R-1-carboxyethyl)]-azetidin-2-one.

Melting Point: 148.5°–151.5° C. $^1$H NMR(CDCl₃) δ: 0.07–0.08 (s, 6H), 0.89 (s, 9H), 1.19 (d, 3H, J=6 Hz), 1.27 (d, 3H, J=7 Hz), 2.78–2.74 (m, 1H), 3.05 (d, 1H, J=4.4 Hz, 2H), 3.98 (d, 1H, J=4.82 Hz), 4.25–4.17 (m, 2H), 6.50 (s, 1H, NH)

Reference Example 5

0.6 g of the compound prepared in Reference Example 4 was dissolved in 5 ml of anhydrous acetonitrile and the resulting solution was stirred for 30 minutes. Then 2.0 g of magnesium p-nitrobenzylmalonate was added thereto and the mixture was stirred for 18 hours at 65° C. The reaction mixture was evaporated to remove the solvent and the residue was suspended in 50 ml of ethyl acetate and then washed successively with 1N-hydrochloric acid solution, 10% potassium carbonate and saline. After removing the solvent, the residue was purified with column chromatography to obtain 70 mg of the desired product (3S,4S)-3-[(R)-1-(t-butyldimethylsilyloxy)ethyl]-4-[(R)-1-(p-nitrobenzylacetoxy)carboxyethyl]azetidin-2-one.

$^1$H NMR(CDCl₃): 0.07 (s, 6H, CH₃×2), 0.9 (s, 9H), 1.10 (d, 3H, CH₃), 1.23 (d, 3H, CH×3), 2.29 (dd,1H), 2.92 (m, 1H), 3.66 (s, 2H), 3.96 (dd, 1H), 4.20 (m, 1H), 5.39 (s, 2H), 7.56 and 8.25 (d, 2H, Ø)

Reference Example 6

2.87 g of the compound prepared in Reference Example 5 was dissolved in 30 ml of methanol and 3 ml of 6N-hydrochloric acid solution was added thereto. The reaction mixture was stirred for 2 hours at room temperature and then adjusted to pH 7 to 8 with 0.1N-phosphate buffer and 10% potassium carbonate. After removing the solvent from the reaction mixture, the residue was extracted with ethyl acetate. The extract was washed with water and concentrated under reduced pressure. The residue was purified with column chromatography to obtain 1.7 g of the desired product (3S,4S)-3-[(R)-1-(t-butyldimethylsilyloxy)ethyl]-4-[(R)-1-(p-nitrobenzylacetoxy)carboxyethyl]azetidin-2-one.

$^{11}$H NMR(CDCl₃) δ: 1.30 (d, 6H), 2.90 (dd, 1H, CH), 2.94 (q, 1H, CH), 3.65–3.70 (ABq, 2H, CH₂), 3.84 (dd, 1H, CH), 4.15 (m, 1H, CH), 7.50 and 8.25 (d, 2H, Ø)

Reference Example 7

0.4 g of the compound prepared in Reference Example 6 was dissolved in 5 ml of anhydrous acetonitrile and to the resulting solution were added 7.4 g of tosyl azide and 0.2 g of triethylamine. The reaction solution was stirred for 2 hours at room temperature and then concentrated under reduced pressure. The residue was subjected to column chromatography to obtain 400 mg of the desired product (3S,4S)-3-[(R)-1-hydroxyethyl]4-[(R)-1-methyl-3-diazo-3-(p-nitrobenzyloxycarbonyl)-2-oxopropyl]azetidin-2-one.

$^1$H NMR(CDCl$_3$) δ: 1.25 (d, 6H), 2.95 (dd, 1H), 3.77 (q, 1H, CH), 3.86 (dd, 1H, CH), 4.15 (m, 1H, CH), 5.38 (s, 2H, CH$_2$), 7.55 and 8.30 (d, 2H, Ø)

Reference Example 8

0.4 g of the compound prepared in Reference Example 7 was added to 20 ml of the mixed solvent of anhydrous ethyl acetate and anhydrous hexane and the resulting mixture was heated for one hour under reflux. A catalytic amount of rhodium acetate was added thereto under warming. The reaction mixture was stirred under reflux for one hour and then filtered with diatomaceous earth to remove the solvent to obtain 380 mg of the desired product p-nitrobenzyl-(1R,5S,6S)-2-keto-6-[(1R)-1-hydroxyethyl]-1-methyl-1-carbapen-2-em-3-carboxylate.

$^1$H NMR(CDCl$_3$) δ: 1.23 (d, 3H, β-methyl), 1.40 (d, 3H, CH$_3$CHOH), 2.86 (q, 1H, CH), 3.30 (dd, 1H, CH), 4.30 (dd, 1H, CH), 4.36 (q, 1H, CH), 4.78 (s, 1H, CH), 5.28 and 5.42 (ABq, 2H, CH$_2$), 7.58 and 8.30 (d, 2H, Ø)

Reference Example 9

13.2 g of trans-4-hydroxy-L-proline was dissolved in 111 ml of 2N-sodium hydroxide solution, and 23.76 g of p-nitrobenzyloxycarbonylchloroformate dissolved in 20 ml of methylene chloride was added thereto while stirring under ice-cooling and the mixture was stirred for 2 hours at the same temperature. Then 50 ml of 2N-sodium hydroxide was added to the mixture to separate the layers. The organic layer was removed, and 18.5 g of concentrated sulfuric acid was added to the aqueous layer to precipitate the product. The resulting product was filtered, washed with distilled water and dried to obtain the desired product trans-1-(p-nitrobenzyloxycarbonyl)-4-hydroxy-L-proline in the yield of 83%.

Melting Point: 132°–135° C. IR(Nujol)cm$^{-1}$: 3300, 1738, 1660, 1665, 1520

Reference Example 10

120 g of the compound prepared in Reference Example 9 was dissolved in 50 ml of methanol and the resulting solution was added dropwise to 50 ml of tetrahydrofuran. To this mixture was added dropwise 60 ml of ethyl ether solution of diazomethane under nitrogen atmosphere while stirring with ice-cooling and the whole mixture was stirred for 20 hours. The reaction solution was concentrated under reduced pressure to obtain the desired product trans-1-(p-nitrobenzyloxycarbonyl)-4-hydroxy-L-proline methyl ester in the yield of 70%.

IR(Neat)cm$^{-1}$: 1748, 1695, 1518, 1438, 1360, 1250, 1175

Reference Example 11

5.18 g of the compound prepared in Reference Example 10, 3.79 g of trimethylamine and 3.77 g of t-butyldimethylsilyl chloride were dissolved in 50 ml of anhydrous dimethylformamide and the resulting solution was stirred for 3 hours at room temperature, diluted with distilled water and then extracted with ethyl acetate. The organic layer was separated and washed successively with distilled water, 1.0N-hydrochloric acid solution and saline, dried and concentrated under reduced pressure to obtain the desired product trans-1-[(p-nitrobenzyloxycarbonyl)-4-(4-(t-butyldi-methylsilyloxy)]-L-proline methyl ester in the yield of 68%.

$[α]_D^{19}$=−36.20° (C=1.00 CHCl$_3$) IR(Neat)cm$^{-1}$: 1750, 1710, 1517, 1415, 1355, 1250, 1115 NMR(CDCl$_3$) δ: 0.08 (9H,s), 1.8–2.4 (2H,m), 3.3–3.8 (2H,m), 3.63 (3H,s), 3.72 (3H,s), 5.20 (1H, J=14 Hz), 5.23 (1H,s), 7.42 (2H, d, J=9 Hz), 8.15 (2H, d, J=9 Hz)

Reference Example 12

5.64 g of the compound prepared in Reference Example 11 was dissolved in 60 ml of anhydrous tetrahydrofuran and 1.0 g of sodium borohydride and 3.52 g of calcium chloride were added to the resulting solution. The reaction solution was refluxed under heating for one hour and diluted with distilled water and then extracted with ethyl acetate. The organic layer was separated, washed with distilled water and saline, dried and concentrated under reduced pressure to obtain the desired product (2S,4S)-[1-(p-nitrobenzyloxycarbonyl)-2-(hydroxymethyl)-4-(t-butyldimethylsilyloxy))pyrrolidine in the yield of 75%.

$[α]_D^{19}$=−40.10° (C=1.00 CHCl$_3$) IR(Neat)cm$^{-1}$: 1670, 1504, 1420, 1405, 1240, 1100 NMR(CDCl$_3$) δ: 0.07 (6H,s), 0.87 (9H,s), 1.4–2.1 (2H,m), 3.38–3.84 (4H,m), 3.9–4.5 (2H,m), 5.22 (2H,s), 7.47 (2H, d, J=9 Hz), 8.17 (2H, d, J=9 Hz)

Reference Example 13

32.6 g of the compound prepared in Reference Example 12 was dissolved in 64 ml of anhydrous pyridine and 28 g of p-toluenesulfonyl chloride was added to the resulting solution and then the mixture was stirred for 12 hours at room temperature. The reaction solution was diluted with distilled water and then extracted with ethyl acetate. The organic layer was separated, washed with saline, 1.0N hydrochloric acid solution and distilled water, dried and concentrated under reduced pressure to obtain the desired product (2S,4S)-[1-(p-nitrobenzyloxycarbonyl)-2-(p-toluenesulfonyloxymethyl)-4-(t-butyldimethylsilyloxy)]pyrrolidine in the yield of 75%.

IR(Neat)cm$^{-1}$: 1700, 1518, 1342, 1265, 1172, 1090

Reference Example 14

35.8 g of the compound prepared in Reference Example 13 and 19 g of sodium iodide were added to 90 ml of methylethylketone and the mixture was refluxed under heating. The reaction solution was cooled to room temperature and then filtered. The filtrate was concentrated under reduced pressure and the residue was dissolved in ethyl acetate, washed with each of distilled water and saline, dried and concentrated under reduced pressure to obtain the desired product (2S,4S)-[1-(p-nitrobenzyloxycarbonyl)-2-(iodomethyl)-4-(t-butyldimethylsilyloxy)]-pyrrolidine in the yield of 70%.

Melting Point: 88°–92° C. IR(Neat)cm$^{-1}$: 1700, 1512, 1405, 1353, 1248 NMR(CDCl$_3$) δ: 0.07 (6H,s), 0.87 (9H,s), 1.4–2.5 (2H,m), 3.1–3.8 (4H,m), 3.95–4.38 (2H,m), 5.22 (2H,s), 7.5–8.3 (4H, d, J=9 Hz)

Reference Example 15-A 5 g of the compound prepared in Reference Example 14 was dissolved in 50 ml of dimethylformamide, and then 2 g of 3-mercaptopropionate ethyl ester, 1.7 g of calcium iodide and 1.7 g of triethylamine were added to the resulting solution while stirring. The reaction mexture was warmed to 60° C. to 70° C. and allowed to react for 4 hours. The reaction mixture was cooled to room temperature, diluted with ethyl acetate, washed several times with distilled water and then washed with 1N hydrochloric acid solution and saline, dried and concentrated under reduced pressure to obtain the desired product (2S,4S)-[1-(p-nitrobenzyloxycarbonyl)-2-(ethyloxycarbonylethylthiomethyl)-4-(t-butyldimethylsilyloxy)]pyrrolidine in the yield of 60%.

IR(Neat)cm$^{-1}$: 1745, 1705, 1695, 1510, 1405, 1342 NMR (CDCl$_3$) δ: 0.07 (6H,s), 0.9 (9H,s), 1.55–2.5 (4H,m), 3.0 (3H,s), 3.15–3.8 (4H,m), 3.95–4.25 (4H, m), 5.22 (2H,s), 7.25–8.35 (9H, d, J=9 Hz)

Reference Example 15-B 11 g of the compound prepared in Reference Example 15-A was dissolved in 20 ml of methanol, and 30 ml of 2N-sodium hydroxide solution was added to the resulting solution while stirring under ice-cooling. The reaction mixture was stirred for 30 minutes, adjusted to neutral pH value by adding 1N-acetic acid and then evaporated under reduced pressure to remove the solvent. The residue was extracted with ethyl acetate. The extract was dried, concentrated under reduced pressure and then subjected to column chromatography to obtain the desired product (2S,4S)-[1-(p-nitrobenzyloxycarbonyl)-2-(hydroxycarbonylethylthiomethyl)-4-(t-butyldimethylsilyloxy)]pyrrolidine in the yield of 85%.

IR(Neat)cm$^{-1}$: 3500, 1725, 1690, 1425, 1350 NMR (CDCl$_3$) δ: 0.08 (6H,s), 0.87 (9H,s), 1.45–2.20 (4H,m), 3.10–3.50 (4H,m), 5.22 (2H,s), 7.25–8.5 (4H, d, J=8 Hz)

Reference Example 15-C 4 g of the compound prepared in Reference Example 15-B was dissolved in 40 ml of anhydrous acetonitrile and 1.56 g of carbonyldiimidazole was added to the resulting solution under ice-cooling. The mixture was stirred for 30 minutes and 2.7 g of triethylamine and 1.06 g of glycinamide hydrochloride were added thereto. The whole mixture was stirred for 2 hours under ice-cooling and then for one hour at room temperature. The reaction solution was diluted with ethyl acetate, washed successively with distilled water, 1N-hydrochloric acid solution, 5% sodium bicarbonate solution and saline, dried and then concentrated under reduced pressure. The residue was subjected to column chromatography eluting with ethyl acetate:n-hexane (1:1) to obtain the desired product (2S,4S)-[1-(p-nitrobenzyloxycarbonyl)-2-(carbamoylmethylcarbamoylethylthiomethyl)-4-(t-butyldimethylsilyloxy)]-pyrrolidine in the yield of 65%.

IR(Neat)cm$^{-1}$: 1725, 1710, 1695, 1515, 1420, 1325 NMR (CDCl$_3$) δ: 0.07 (6H,s), 0.8 (9H,s), 1.25–1.45 (2H,m), 2.25–2.50 (4H,m), 3.95–4.25 (2H,m), 5.25 (2H,s), 7.5–8.5 (4H, d, J=8 Hz)

Reference Example 15-D 2.93 g of the compound prepared in Reference Example 15-C was dissolved in 15 ml of methanol and 2 ml of 6N-hydrochloric acid solution was added to the resulting solution while stirring under ice-cooling. The mixture was stirred for 2 hours at the same temperature. The reaction solution was concentrated under reduced pressure and the residue was extracted with ethyl acetate. The extract was dried and then concentrated under reduced pressure to remove the solvent. The residue was subjected to column chromatography eluting with ethyl acetate:n-hexane (3:1) to obtain the desired product (2S,4S)-[1-(p-nitrobenzyloxycarbonyl)-2-(carbamoylmethylcarbamoylethylthiomethyl)-4-(hydroxy)]pyrrolidine in the yield of 93.3%.

IR(Neat)cm$^{-1}$: 3600, 1720, 1700, 1690, 1510, 1420 NMR (CDCl$_3$) δ: 1.80–2.18 (2H,m), 2.65–3.05 (2H,m), 3.09 (2H, s), 3.30–3.35 (2H,m), 3.85–4.50 (2H,m), 4.96–5.24 (2H, d, J=8 Hz), 7.66–8.26 (4H, d, J=8 Hz)

Reference Example 15-E 2.17 g of the compound prepared in Reference Example 15-D was dissolved in 30 ml of anhydrous dichloromethane and 0.59 of methanesulfonyl chloride and 0.71 g of triethylamine were added to the resulting solution while stirring under ice-cooling. Then, the mixture was stirred for 2 hours at the same temperature. The reaction solution was then washed with distilled water, 1N hydrochloric acid solution and saline, dried and concentrated under reduced pressure to obtain the desired product (2S,4S)-[1-(p-nitrobenzyloxycarbonyl)-2-(carbamoylmethylcarbamoylethylthiomethyl)-4-(mesyloxy)]pyrrolidine in the yield of 66.1%.

IR(Neat)cm$^{-1}$: 1710, 1700, 1690, 1510, 1435, 1350, 1050 NMR(CDCl$_3$) δ: 2.05–2.60 (3H,m), 3.03 (3H,s), 5.25 (2H, s), 7.53 (2H, d, J=8 Hz), 8.25 (2H, d, J=8 Hz)

Reference Example 15-F

To 20 ml of dimethylformamide were added 2 g of the compound prepared in Reference Example 15-E and 0.57 g of potassium thioacetate and then the reaction mixture was stirred for 4 hours at 70° to 80° C. The reaction mixture was cooled to room temperature, diluted with ethyl acetate and then washed several times with distilled water, dried and concentrated under reduced pressure. The residue was subjected to column chromatography eluting with ethyl acetate to obtain the desired product (2S,4S)-[1-(p-nitrobenzyloxycarbonyl)-2-(carbamoylmethylcarbamoylethylthiomethyl)-4-(acetylthio)]pyrrolidine in the yield of 65.2%.

IR(Neat)cm$^{-1}$: 1725, 1710, 1690, 1510, 1420, 1350 NMR (CDCl$_3$) δ: 2.40–3.15 (4H,m), 3.25 (3H,s), 3.75–4.50 (4H, m), 5.23 (2H,s), 7.25–8.23 (4H, d, J=8 Hz)

Reference Example 15-G 1.5 g of the compound prepared in Reference Example 15-F was dissolved in 15 ml of methanol and 0.2 g of sodium methoxide was added to the resulting solution while stirring under ice-cooling. The mixture was stirred for 15 minutes at the same temperature. The reaction mixture was added to acetic acid to neutralize and then concentrated under reduced pressure. The residue was extracted with ethyl acetate. The extract was dried and then concentrated under reduced pressure to obtain the desired product (2S,4S)-1-(p-nitrobenzyloxycarbonyl)-2-(carbamoylmethylcarbamoylethylthiomethyl)-4-mercaptopyrrolidine in the yield of 85.2%.

IR(Neat)cm$^{-1}$: 1710, 1690, 1510, 1425 NMR(CDCl$_3$) δ: 1.75–1.95 (3H,m), 2.45–2.85 (2H,m), 2.90–3.15 (2H,m), 3.21 (2H,s), 3.25–4.30 (4H,m), 5.24 (2H,s), 7.55–8.27 (4H, d, J=8 Hz)

Reference Example 16-A

The reaction was carried out in the same manner as that of Reference Example 15-A, using 7 g of the compound prepared in Reference Example 14, 1.8 ml of ethylthioglyconate, 2.7 g of calcium iodide and 2.1 ml of triethylamine to obtain the desired product (2S,4S)-[1-(p-nitrobenzyloxycarbonyl)-2-(ethyloxycarbonylmethylthiomethyl)-4-(t-butyldimethylsilyloxy)]-pyrrolidine in the yield of 75%.

IR(Neat)cm$^{-1}$: 1745, 1700, 1690, 1515, 1410 NMR (CDCl$_3$) δ: 0.07 (6H,s), 0.9 (9H,s), 1.50–1.98 (2H,m), 2.02–2.25 (2H,m), 3.0 (3H,s), 3.15–3.8 (2H, m), 3.95–4.25 (4H,m), 5.22 (2H,s), 7.25–8.35 (4H, d, J=8 Hz)

Reference Example 16-B 3 g of the compound prepared in Reference Example 16-A was treated in the same manner as that of Reference Example 15-B to obtain the desired product (2S,4S)-[1-(p-nitrobenzyloxycarbonyl)-2-(hydroxycarbonylmethyl-thiomethyl)-4-(t-butyldimethylsilyloxy)]pyrrolidine in the yield of 60%.

IR(Neat)cm$^{-1}$: 3600, 1720, 1695, 1520, 1420 NMR (CDCl$_3$) δ: 0.08 (6H,m), 0.85 (9H,s), 1.45–2.20 (2H,m), 3.10–3.45 (4H,m), 5.22 (2H,s), 7.25–8.5 (4H, d, J=8 Hz)

Reference Example 16-C 5 g of the compound prepared in Reference Example 16-B was dissolved in 30 ml of anhydrous acetonitrile solution and 2 g of carbonyldiimidazole was added to the resulting solution while stirring under ice-cooling. After stirring the mixture, 3.0 g of triethylamine and 1.5 g of glycinamide hydrochloride were successively added thereto and the reaction mixture was then treated in the same manner as that of Reference Example 15-C to obtain the desired product (2S,4S)-[1-(p-nitrobenzyloxycarbonyl)-2-(carbamoylmethylcarbamoylmethylthiomethyl)-4-(t-butyldimethylsilyloxy)]pyrrolidine in the yield of 80%.

IR(Neat)cm$^{-1}$: 1720, 1705, 1695, 1570 NMR(CDCl$_3$) δ: 0.06 (6H; s), 0.86 (9H,s), 1.88–2.22 (2H,m), 3.22 (2H,s), 5.25 (2H,s), 7.53 (2H, d, J=8 Hz), 8.25 (2H, d, J=8 Hz)

Reference Example 16-D 3.2 g of the compound prepared in Reference Example 16-B was treated in the same manner as that of Reference Example 15-C to obtain the desired product (2S,4S)-[1-(p-nitrobenzyloxycarbonyl)-2-(carbamoylmethylcarbamoyl-methylthiomethyl)-4-(hydroxy)]pyrrolidine in the yield of 85.2%.

IR(Neat)cm$^{-1}$: 3600, 1715, 1700, 1510, 1400 NMR (CDCl$_3$) δ: 1.80–2.10 (2H,m), 2.65–3.05 (2H,m), 3.09 (2H, s), 3.30–3.55 (2H,m), 3.85–4.50 (2H,m), 4.95–5.24 (2H,s), 7.66–8.26 (4H, d, J=8 Hz)

Reference Example 16-E 2 g of the compound prepared in Reference Example 16-D was dissolved in 30 ml of anhydrous dichloromethane, and 0.75 g of triethylamine and 0.6 g of methanesulfonyl chloride were added to the resulting solution. Then, the reaction mixture was treated in the same manner as that of Reference Example 15-E to obtain the desired product (2S,4S)-[1-(p-nitrobenzyloxycarbonyl)-2-(carbamoyl-methylcarbamoylmethylthiomethyl)-4-(mesyloxy)]pyrrolidine in the yield of 72%.

IR(Neat)cm$^{-1}$: 1715, 1700, 1695, 1500, 1410, 1355 NMR (CDCl$_3$) δ: 2.05–2.60 (3H,m), 3.03 (3H,s), 5.25 (2H,s), 7.53–8.25 (4H, d, J=8 Hz)

Reference Example 16-F 1.9 g of the compound prepared in Reference Example 16-E was added to 15 ml of dimethylformamide and 0.5 g of potassium thioacetate and the resulting mixture was treated in the same manner as that of Reference Example 15-E to obtain the desired product (2S,4S)-[1-(p-nitrobenzyloxycarbonyl)-2-(carbamoylmethylcarbamoyl-methylthiomethyl)-4-(acetylthio)]pyrrolidine in the yield of 57%.

IR(Neat)cm$^{-1}$: 1725, 1750, 1695, 1500 NMR(CDCl$_3$) δ: 2.40–3.15 (4H,m), 3.21 (3H,s), 3.75–4.50 (5H, m), 5.23 (2H,s), 7.59–8.23 (4H, d, J=8 Hz)

Reference Example 16-G 2.0 g of the compound prepared in Reference Example 16-F was dissolved in 18 ml of methanol and 0.25 g of sodium methoxide was added to the resulting solution while stirring under ice-cooling. The reaction mixture was then treated in the same manner as that of Reference Example 15-G to obtain the desired product (2S,4S)-[1-(p-nitrobenzyloxycarbonyl)-2-(carbamoylmethylcarbamoyl-methylthiomethyl)-4-(mercapto)]pyrrolidine in the yield of 78%.

IR(Neat)cm$^{-1}$: 1710, 1695, 1520, 1425, 1350 NMR (CDCl$_3$) δ: 1.75–1.95 (3H,m), 2.45–2.85 (2H,m), 2.90–3.15 (2H,m), 3.21 (2H,s), 3.25–3.50 (2H,m), 3.85–4.30 (2H,m), 5.24 (2H,s), 7.55–8.27 (4H, d, J=8 Hz)

Reference Example 17-A 4 g of the compound prepared in Reference Example 14 was dissolved in 40 ml of anhydrous acetonitrile and 1.56 g of carbonyldiimidazole was added to the resulting solution. After stirring the mixture for 30 minutes, 2.7 g of triethylamine and 2.3 g of aminoacetonitrile hydrochloride were added thereto and the whole mixture was stirred for 2 hours under ice-cooling and then one hour at room temperature. The reaction solution was diluted with ethyl acetate, washed successively with distilled water, 1N-hydrochloric acid solution, 5% sodium bicarbonate solution and saline, dried and then concentrated under reduced pressure. The residue was subjected to column chromatography eluting with ethyl acetate:n-hexane (2:1) to obtain the desired product (2S,4S)-(1-(p-nitrobenzyloxycarbonyl)-2-(cyanomethylcarbamoyl-ethylthiomethyl)-4-(t-butyldimethylsilyloxy)]pyrrolidine in the yield of 65%.

IR(Neat)cm$^{-1}$: 2250, 1725–1710, 1690–1665 NMR (CDCl$_3$) δ: 0.05 (6H,s), 0.86 (9H,s), 1.80–2.15 (4H,m), 5.25 (2H,s), 7.25–8.21 (4H, d, J=8 Hz)

Reference Example 17-B 3.5 g of the compound prepared in Reference Example 17-A was dissolved in 15 ml of methanol and 2 ml of 6N-hydrochloric acid solution was added to the resulting solution while stirring under ice-cooling. The reaction solution was stirred for 2 hours at the same temperature and concentrated under reduced pressure. The residue was extracted with ethyl acetate and the extract was dried and then concentrated under reduced pressure to remove the solvent. The residue was subjected to column chromatography eluting with ethyl acetate:n-hexane (3:1) to obtain the desired product (2S,4S)-[1-(p-nitrobenzyloxycarbonyl)-2-(cyanomethylcarbamoylethylthiomethyl)-4-(hydroxy)]pyrrolidine in the yield of 87.5%.

IR(Neat)cm$^{-1}$: 2250, 1710, 1695–1675, 1610, 1525 NMR (CDCl$_3$) δ: 1.52–1.95 (2H,m), 2.75–3.50 (2H,m), 4.05–4.75 (4H,m), 5.23 (2H,s), 7.53–8.22 (4H, d, J=8 Hz)

Reference Example 17-C 2.78 g of the compound prepared in Reference Example 17-B was dissolved in 30 ml of anhydrous dichloromethane and 0.62 g of methanesulfonyl chloride and 1.4 g of triethylamine were added to the resulting solution while stirring under ice-cooling. The mixture was stirred for 2 hours at the same temperature. The reaction solution was washed with distilled water, 1N-hydrochloric acid solution and saline, dried and then concentrated under reduced pressure to obtain the desired product (2S,4S)-[1-(p-nitrobenzyloxycarbonyl)-2-(cyanomethylcarbamoylethylthiomethyl)-4-(mesyloxy)] pyrrolidine in the yield of 72.5%.

IR(Neat)cm$^{-1}$: 2250, 1710, 1700, 1690, 1510, 1435, 1350, 1050 NMR(CDCl$_3$) δ: 2.05–2.80 (4H,m), 3.03 (3H, m), 7.53–8.25 (4H, d, J=8 Hz)

Reference Example 17-D 2.8 g of the compound prepared in Reference Example 17-C was added to 20 ml of dimethylformamide and then 0.65 g of potassium thioacetate was added thereto. The reaction mixture was stirred for 4 hours at 70° to 80° C. and then cooled to room temperature, diluted with ethyl acetate, washed several times with distilled water, dried and concentrated under reduced pressure. The residue was subjected to column chromatography eluting with ethyl acetate to obtain the desired product (2S,4S)-[1-(p-nitrobenzyloxycarbonyl)-2-(cyanomethylcarbamoylethylthiomethyl)-4-(acetylthio)]pyrrolidine in the yield of 73.5%.

NMR(CDCl$_3$) δ: 1.75–2.40 (4H,m), 3.25–4.55 (6H,m), 7.85–8.10 (4H, d, J=8 Hz)

Reference Example 17-E 0.9 g of the compound prepared in Reference Example 17-D was dissolved in 15 ml of methanol, and 0.1 g of sodium methoxide was added to the resulting solution while stirring under ice-cooling. The reaction solution was stirred for 15 minutes at the same temperature, neutralized with acetic acid and then concentrated under reduced pressure. The residue was extracted with ethyl acetate and the extract was dried and concentrated under reduced pressure to obtain the desired product (2S,4S)-1-(p-nitrobenzyloxycarbonyl)-2-(cyanomethylcarbamoylethylthiomethyl)-4-mercaptopyrrolidine in the yield of 63.8%.

IR(Neat)cm$^{-1}$: 1720–1690, 1605, 1530–1515 NMR (CDCl$_3$) δ: 1.65–1.94 (3H,m), 2.45–2.85 (2H,m), 2.90–3.30 (4H,m), 3.25–3.50 (2H,m), 5.24 (2H,s), 7.55–8.24 (4H, d, J=8 Hz)

Reference Example 18-A 6 g of the compound prepared in Reference Example 14 was dissolved in 40 ml of anhydrous acetonitrile and 2.5 g of carbonyldiimidazole was added to the resulting solution while stirring under ice-cooling. After stirring the mixture, 3.5 g of triethylamine and 2.1 g of aminoacetonitrile hydrochloride were successively added thereto. Then, the subsequent reaction was carried out in the same manner as that of Reference Example 15-C to obtain the desired product (2S,4S)-[1-(p-nitrobenzyloxycarbonyl)-2-(cyanomethylcarbamoylmethylthiomethyl)-4-(t-butyldimethylsilyloxy)] pyrrolidine in the yield of 88.5%.

IR(Neat)cm$^{-1}$ : 2250, 1735–1710, 1695–1665, 1610 NMR(CDCl$_3$) δ: 0.06 (6H,s), 0.85 (9H,s), 1.75–2.10 (4H, m), 5.25 (2H,s), 7.30–8.56 (4H, d, J=8 Hz)

Reference Example 18-B 2.5 g of the compound prepared in Reference Example 18-A was treated in the same manner as that of Reference Example 15-D to obtain the desired product (2S,4S)-[1-(p-nitrobenzyloxycarbonyl)-2-(cyanomethylcarbamoyl-methylthiomethyl)- 4-(hydroxy)]pyrrolidine in the yield of 90.8%.

IR(Neat)cm$^{-1}$: 2250, 1745–1710, 1690–1675 NMR (CDCl$_3$) δ: 1.75–2.25 (2H,m), 2.55–3.10 (2H,m), 3.90 (2H, s), 3.30–3.45 (3H,m), 4.95–5.24 (2H,s), 7.66–8.25 (4H, d, J=8 Hz)

Reference Example 18-C 2.5 g of the compound prepared in Reference Example 18-B was dissolved in 30 ml of anhydrous dichloromethane and 0.8 g of methanesulfonyl chloride and 1.0 g of triethylamine were added to the resulting solution while stirring under ice-cooling. The resulting reaction mixture was treated in the same manner as that of Reference Example 15-E to obtain the desired product (2S,4S)-[1-(p-nitrobenzyloxycarbonyl)-2-(cyanomethylcarbamoylmethylthiomethyl)-4-(mesyloxy)]pyrrolidine in the yield of 72%.

IR(Neat)cm$^{-1}$: 2250, 1725–1690, 1660, 1610 NMR (CDCl$_3$) δ: 2.10–2.45 (3H,m), 3.03 (3H,s), 5.25 (2H,s), 7.53–8.25 (4H, d, J=8 Hz)

Reference Example 18-D 2.5 g of the compound prepared in Reference Example 18-C was added to 15 ml of dimethylformamide and 0.8 g of potassium thioacetate and then the reaction mixture was treated in the same manner as that of Reference Example 15-E to obtain the desired product (2S,4S)-(1-(p-nitrobenzyloxycarbonyl)-2-(cyanomethylcarbamoylmethylthiomethyl)-4-(acetylthio)]pyrrolidine in the yield of 63.5%.

IR(Neat)cm$^{-1}$: 2250, 1725, 1750, 1695, 1500 NMR (CDCl$_3$) δ: 2.15–3.00 (4H,m), 3.2 (3H,s), 3.75–4.50 (5H,m), 5.23 (2H,s), 7.59–8.23 (4H, d, J=8 Hz)

Reference Example 18-E 1.8 g of the compound prepared in Reference Example 18-D was dissolved in 18 ml of methanol, and 0.25 g of sodium methoxide was added to the resulting solution while stirring under ice-cooling. The reaction mixture was treated in the same manner as that of Reference Example 15-G to obtain the desired product (2S,4S)-[1-(p-nitrobenzyloxycarbonyl)-2-(cyanomethylcarbamoylmethylthiomethyl)-4-(mercapto)]pyrrolidine in the yield of 65.8%.

IR(Neat)cm$^{-1}$: 2250, 1735–1710, 1695–1675, 1610 NMR (CDCl$_3$) δ: 1.65–1.75 (3H,m), 2.45–2.85 (2H,m), 2.90–3.30 (5H,m), 3.50 (2H,m), 5.24 (2H,s), 7.55–8.27 (4H, d, J=8 Hz)

Reference Example 19-A 52 g of the compound prepared in Reference Example 14 and 18.3 g of potassium thioacetate were added to 50 ml of dimethylformamide and the mixture was warmed to 60° to 75° C. and stirred for 2 hours. The reaction solution was cooled to room temperature, diluted with distilled water and extracted with ethyl acetate. The organic layer was washed with distilled water, saline and 5% sodium bicarbonate solution, dried and concentrated under reduced pressure to obtain the desired product (2S,4S)-[1-(p-nitrobenzyloxycarbonyl)-2-(acetylthiomethyl)-4-(t-butyldimethylsilyloxy)]pyrrolidine in the yield of 55%.

IR(Neat)cm$^{-1}$: 1710–1700, 1610, 1530 NMR(CDCl$_3$) δ: 0.06 (6H,s), 1.84 (9H,s), 2.35 (3H,s), 5.26(2H,s), 7.54–8.22 (4H, d, J=8 Hz)

Reference Example 19-B 5 g of the compound prepared in Reference Example 19-A was dissolved in 10 ml of methanol and 2 ml of 28% sodium methoxide was added to the resulting solution while stirring under ice-cooling. The mixture was stirred for 15 minutes under nitrogen atmosphere and then 1 g of 2-iodoethanol dissolved in 10 ml of methanol was added dropwise thereto at the same temperature. The reaction mixture was stirred for 4 hours at the same temperature and concentrated under reduced pressure to remove the solvent. The residue was dissolved in ethyl acetate, washed with distilled water, dried and then concentrated under reduced pressure to remove the solvent to obtain the desired product (2S,4S)-[1-(p-nitrobenzyloxycarbonyl)-2-(hydroxyethylthiomethyl)-4-(t-butyldimethylsilyloxy)]pyrrolidine in the yield of 50%.

IR(Neat)cm$^{-1}$: 1710, 1690–1675, 1610, 1525 NMR (CDCl$_3$) δ: 0.06 (6H,s), 0.86 (9H,s), 1.88–2.22 (2H,m), 3.22 (2H,s), 5.25 (2H,s), 7.53–8.29 (4H, d, J=8 Hz)

Reference Example 19-C 850 mg of the compound prepared in Reference Example 19-B and 1 ml of 6N-hydrochloric acid solution were added to 8 ml of methanol and the mixture was stirred for one hour, diluted with ethyl acetate, washed with distilled water, dried and then concentrated under reduced pressure. The residue was purified with column chromatography to obtain the desired product (2S,4S)-[1-(p-nitrobenzyloxycarbonyl)-2-(acetoxyethylthiomethyl)-4-(hydroxy)]pyrrolidine in the yield of 70%.

IR(CHC$_{13}$)cm$^{-1}$: 1710, 1610, 1525 NMR(DMSO-d$_6$) δ: 1.80–2.15 (2H,m), 2.65–3.05 (2H,m), 3.09 (2H,s), 3.30–3.55 (2H,m), 5.24 (2H,s), 7.66–8.26 (2H, d, J=8 Hz)

Reference Example 19-D 1.5 g of the compound prepared in Reference Example 19-C, 2.2 g of triphenylphosphine and 5 g of diethylazodicarboxylate were respectively added to 20 ml of anhydrous tetrahydrofuran solution, and the mixture was stirred for 2 hours under ice-cooling. 1.2 g of thiolacetic acid was added to the reaction mixture at the same temperature and the mixture was stirred for 2 hours. The reaction solution was increased to room temperature and then stirred for 20 hours, evaporated under reduced pressure, diluted with ethyl acetate, washed with distilled water, dried and then concentrated under reduced pressure. The residue was purified with column chromatography to obtain the desired product (2S,4S)-[1-(p-nitrobenzyloxycarbonyl)-2-(acetoxyethylthiomethyl)-4-(acetylthio)]pyrrolidine in the yield of 70%.

IR(Neat)cm$^{-1}$: 1745, 1710, 1600, 1510, 1398, 1360, 1098 NMR(CDCl$_3$) δ: 1.75–1.95 (3H,m), 2.45–2.85 (1H,m), 2.90–3.15 (2H,m), 3.21 (2H,s), 3.25–3.50 (2H,m), 3.58–4.30 (2H,m), 5.24 (2H,s), 7.55–8.27 (4H, d, J=8 Hz)

Reference Example 20-A 5 g of the compound prepared in Reference Example 19-A was dissolved in 10 ml of methanol, and 2 ml of 28% sodium methoxide was added to the resulting solution under ice-cooling. The mixture was stirred for 15 minutes under nitrogen atmosphere. To this mixture was added 1 g of 2-iodoethanol dissolved in 10 ml of methanol at the same temperature. The reaction mixture was stirred for 4 hours at the same temperature and concentrated under reduced pressure to remove the solvent. The residue was dissolved in ethyl acetate, washed with distilled water, dried and concentrated under reduced pressure to remove the solvent to obtain the desired product (2S,4S)-[1-(p-nitrobenzyloxycarbonyl)-2-(hydroxyethylthiomethyl)-4-(t-butyldimethylsilyloxy)]pyrrolidine in the yield of 50%.

IR(Neat)cm$^{-1}$: 3600, 1740, 1690, 1523, 1400, 1345 NMR (CDCl$_3$) δ: 0.06 (6H,s), 0.86 (9H,s), 1.51–2.1 (2H,m), 2.4–2.9 (2H,m), 3.22 (2H,s), 5.25 (2H,s), 7.53–8.25 (4H, d, J=8 Hz)

Reference Example 20-B 1.5 g of the compound prepared in Reference Example 20-A was dissolved in 15 ml of anhydrous pyridine and 0.8 ml of acetic anhydride and 0.3 g of dimethylaminopyridine were added to the resulting solution. The mixture was stirred for one hour at room temperature, diluted with ethyl acetate, washed with distilled water and then concentrated under reduced pressure. The residue was purified with column chromatography to obtain the desired product (2S,4S)-[1-(p-nitrobenzyloxycarbonyl)-2-(acetoxyethylthiomethyl)-4-(t-butyldimethylsilyloxy)]pyrrolidine in the yield of 70%.

IR(Neat)cm$^{-1}$: 1740, 1725–1710, 1690, 1610 NMR (CDCl$_3$) δ: 0.06 (6H,s), 0.8 (9H,s), 1.52–1.95 (2H,m), 2.4–2.65 (2H,m), 3.15–3.35 (3H,s), 5.25 (2H,s), 7.53–8.25 (4H, d, J=8 Hz)

Reference Example 20-C 850 mg of the compound prepared in Reference Example 20-B and 1 ml of 6N-hydrochloric acid solution were added to 8 ml of methanol. The reaction mixture was stirred for one hour at room temperature, diluted with 20 ml of ethyl acetate, washed with distilled water, dried and concentrated under reduced pressure. The residue was purified with column chromatography to obtain the desired product (2S,4S)-[1-(p-nitrobenzyloxycarbonyl)-2-(acetoxyethylthiomethyl)-4-(hydroxy)]pyrrolidine in the yield of 70%.

IR(Neat)cm$^{-1}$: 3600, 1720, 1680, 1510, 1410, 1342, 1225 NMR(CDCl$_3$) δ: 1.52–1.95 (2H,m), 2.75–2.95 (2H,m), 3.35 (3H,s), 4.05–4.75 (2H,m), 5.25 (2H,s), 7.53–8.22 (4H, d, J=8 Hz)

Reference Example 20-D 1.5 g of the compound prepared in Reference Example 20-C, 2.2 g of triphenylphosphine and 5 g of diethylazodicarboxylate were added to 20 ml of anhydrous tetrahydrofuran solution. The mixture was stirred for 2 hours under ice-cooling, and 1.2 g of thiolacetic acid was added thereto at the same temperature. The reaction mixture was increased to room temperature and then stirred for 20 hours, evaporated under reduced pressure, diluted with ethyl acetate, washed with distilled water and then concentrated under reduced pressure. The residue was purified with column chromatography to obtain the desired product (2S,4S)-[1-(p-nitrobenzyloxycarbonyl)-2-(acetoxyethylthiomethyl)-4-(acetylthio)]-pyrrolidine in the yield of 70%.

IR(Neat)cm$^{-1}$: 1745, 1710, 1600, 1510, 1398, 1360, 1098

Reference Example 20-E 300 mg of the compound prepared in Reference Example 20-D was dissolved in 5 ml of methanol and 2 ml of 1 N sodium hydroxide solution was added to the resulting solution. The mixture was stirred for 20 minutes in nitrogen atmosphere under ice-cooling and then 2 ml of 1N hydrochloric acid solution was added thereto. The reaction solution was concentrated under reduced pressure, and the residue was dissolved in ethyl acetate, washed with distilled water and saline, dried, and then concentrated under reduced pressure to obtain an oily residue. This oily residue was purified with column chromatography to obtain the desired product (2S,4S)-(1-(p-nitrobenzyloxycarbonyl)-2-(hydroxyethylthiomethyl)-4-(mercapto)]pyrrolidine in the yield of 46%.

IR(Neat)cm$^{-1}$: 3600, 1725, 1680, 1522, 1433, 1410, 1350 NMR(CDCl$_3$) δ: 1.85–2.22 (2H,m), 2.65–3.05 (2H,m), 3.09 (2H,m), 3.30–3.55 (2H,m), 3.85–4.50 (2H,m), 5.24 (2H,s), 7.66–8.26 (4H, d, J=8 Hz)

Reference Example 21-A 4 g of the compound prepared in Reference Example 15-B was dissolved in 50 ml of anhydrous acetonitrile and 1.56 g of carbonyldiimidazole was added to the resulting solution under ice-cooling. The reaction mixture was stirred for 30 minutes and 2.5 g of triethylamine and 2 g of 4-aminoacetyloxyethylpiperazine were added thereto. The whole mixture was stirred for 2 hours under ice-cooling and then for 4 hours at room temperature to complete the reaction. The reaction solution was diluted with ethyl acetate, washed with distilled water, 1N-hydrochloric acid solution, 5% sodium bicarbonate solution and saline, dried and then concentrated under reduced pressure. The residue was subjected to column chromatography eluting with ethyl acetate:n-hexane (1:3) to obtain the desired product (2S,4S)-[1-(p-nitrobenzyloxycarbonyl)-2-{(acetyloxyethylpiperazinylcarbamoyl)ethylmercaptomethyl}-4-(t-butyldimethylsilyloxy)]pyrrolidine in the yield of 68%.

IR(Neat)cm$^{-1}$: 1740, 1710–1690, 1550 NMR(CDCl$_3$) δ: 0.07 (6H,s), 0.8 (9H,s), 1.25–1.55 (4H,m), 2.10–2.50 (4H, m), 5.25 (2H,s), 7.5–8.5 (4H, d, J=8 Hz)

Reference Example 21-B 3.15 g of the compound prepared in Reference Example 21-A was dissolved in 15 ml of methanol, and 1.5 ml of 6N-hydrochloric acid solution was added to the resulting solution while stirring under ice-cooling. The reaction solution was stirred for 2 hours at the same temperature and then concentrated under reduced pressure. The residue was extracted with ethyl acetate, dried and then concentrated under reduced pressure to remove the solvent. The residue was subjected to column chromatography eluting with ethyl acetate:n-hexan (3:1) to obtain the desired product (2S,4S)-[1-(p-nitrobenzyloxycarbonyl)-2-{(acetyloxyethylpiperazinyl)carbamoylethylthiomethyl}-4-(hydroxy)]pyrrolidine in the yield of 87.2%.

IR(Neat)cm$^{-1}$: 3600, 1720, 1690, 1420 NMR(CDCl$_3$) δ: 1.80–2.10 (2H,m), 2.65–3.05 (4H,m), 3.90 (2H,s), 3.30–3.35 (2H,m), 4.96–5.29 (2H, d, J=8 Hz), 7.66–8.26 (4H, d, J=8 Hz)

Reference Example 21-C 1.85 g of the compound prepared in Reference Example 21-B was dissolved in 30 ml of anhydrous dichloromethane, and 0.45 g of methanesulfonyl chloride and 0.62 g of triethylamine were added to the resulting solution. The reaction solution was stirred for 2 hours at the same temperature, washed with distilled water, 1N-hydrochloric acid solution and saline, dried and then concentrated under reduced pressure to obtain the desired product (2S,4S)-[1-(p-nitrobenzyloxycarbonyl)-2-{(acetyloxypiperazinylcarbamoyl)ethylthiomethyl}-4-(mesyloxy)]pyrrolidine in the yield of 68.5%.

IR(Neat)cm$^{-1}$: 1745, 1710–1695, 1610, 1580 NMR (CDCl$_3$) δ: 2.10–2.55 (4H,m), 3.30–3.33 (3H,m), 5.25 (2H, s), 7.58 (2H, d, J=8 Hz), 8.25 (2H, d, J=8 Hz)

Reference Example 21-D 2 g of the compound prepared in Reference Example 21-C was added to 20 ml of dimethylformamide, and 0.57 g of potassium thioacetate was added thereto. The reaction mixture 4was stirred for 4 hours at 70° to 80° C. and then cooled to room temperature. Then, the mixture was diluted with ethyl acetate, washed several times with distilled water, dried and then concentrated under reduced pressure. The residue was subjected to column chromatography eluting with ethyl acetate to obtain the desired product (2S,4S)-[1-(p-nitrobenzyl-oxycarbonyl)-2-{(acetyloxyethylpiperazinyl)carbamoylethylthiomethyl}-4-(acetylthio)]pyrrolidine in the yield of 65.2%.

IR(Neat)cm$^{-1}$: 1725, 1710, 1690, 1510, 1420, 1350 NMR (CDCl$_3$) δ: 2.55–3.15 (4H,m), 3.25–3.35 (3H,m), 3.75–4.50 (4H,m), 5.23 (2H,s), 7.25–8.55 (4H, d, J=8 Hz)

Reference Example 21-E 2.0 g of the compound prepared in Reference Example 21-D wad dissolved in 15 ml of methanol, and 0.21 g of sodium methoxide was added to the resulting solution while stirring under ice-cooling. The mixture was stirred for 15 minutes at the same temperature and then neutralized with acetic acid. The reaction solution was concentrated under reduced pressure. The residue was extracted with ethyl acetate, dried and concentrated under reduced pressure to obtain the desired product (2S,4S)-[1-(p-nitrobenzyloxycarbonyl)-2-[(hydroxyethylpiperazinylcarbamoyl)ethylthiomethyl]-4-mercaptopyrrolidine in the yield of 70.1%.

IR(Neat)cm$^{-1}$: 1740, 1690, 1550 NMR(CDCl$_3$) δ: 1.75–1.88 (3H,m), 2.45–2.85 (2H,m), 2.90–3.15 (2H,m), 3.21 (2H,s), 3.25–4.30 (4H,m), 5.24 (2H,s), 7.55–8.27 (4H, d, J=8 Hz)

Reference Example 22-A 3.5 g of the compound prepared in Reference Example 15-B was dissolved in 50 ml of anhydrous acetonitrile, and 1.8 g of carbonyldiimidazole was added to the resulting solution under ice-cooling. The mixture was stirred for 30 minutes and then 21 g of triethylamine and 2.5 g of glycinamide hydrochloride were added thereto. The reaction mixture was stirred for 2 hours under ice-cooling and then 11 hours at room temperature. The reaction solution was diluted with ethyl acetate, washed with distilled water, 1N-hydrochloric acid solution, 5% sodium bicarbonate solution and saline, respectively, dried and then concentrated under reduced pressure. The residue was subjected to column chromatography eluting with ethyl acetate: n-hexane (10:1) to obtain the desired product (2S,4S)-[1-(p-nitrobenzyloxycarbonyl)-2-{(hydroxycarbonylmethylcarbamoyl)methylcarbamoylethylthiomethyl}-4-(t-butyldimethylsilyloxy)]pyrrolidine in the yield of 65%.

IR(Neat)cm$^{-1}$: 2250, 1725–1710, 1690–1665 NMR (CDCl$_3$) δ: 0.07 (6H,s), 0.09 (9H,s), 1.27–1.31 (4H,m), 2.25–2.60 (4H,m), 3.95–4.45 (2H,m), 5.25 (2H,s), 7.5–8.25 (4H, d, J=8 Hz)

Reference Example 22-B 4.2 g of the compound prepared in Reference Example 22-A was dissolved in 50 ml of anhydrous acetonitrile solution, and 2.5 g of carbonyldiimidazole was added to the resulting solution under ice-cooling. The mixture was stirred for 30 minutes. To this mixture were added 21 g of triethylamine and 2.06 g of 4-aminohydroxyethylpiperazine, and the whole mixture was stirred for 2 hours under ice-cooling and then 10 hours at room temperature. The reaction solution was diluted with ethyl acetate, washed with distilled water, 1N hydrochloric acid solution, 5% sodium bicarbonate solution and saline, respectively, dried and then concentrated under reduced pressure. The residue was subjected to column chromatography eluting with ethyl acetate to obtain the desired product (2S,4S)-(1-(p-nitrobenzyloxycarbonyl)-2-{(hydroxyethylpiperazinylcarbamoylmethylcarbamoyl)ethylthiomethyl}-4-(t-butyldimethylsilyloxy)]pyrrolidine in the yield of 52%.

IR(Neat)cm$^{-1}$: 1730, 1710, 1680, 1510 NMR(CDCl$_3$) δ: 0.07 (6H,s), 0.09 (9H,s), 1.25–1.65 (4H,m), 2.25–2.45 (4H, m), 3. 01–3.75 (4H,m), 4.15–4.25 (2H,m), 5.25 (2H,s), 7.55–8.52 (4H, d, J=8 Hz)

Reference Example 22-C

To 10 ml of acetic anhydride were added 2.6 g of the compound prepared in Reference Example 22-B and 2.5 g of triethylamine and the mixture was stirred for 5 hours under reflux. The reaction solution was evaporated under reduced pressure. The residue was dissolved in ethyl acetate, washed successively with 1N-hydrochloric acid solution, 5% sodium bicarbonate solution and distilled water, dried and then distilled under reduced pressure. The residue was subjected to column chromatography eluting with ethyl acetate to obtain the desired product (2S,4S)-[1-(p-nitrobenzyloxycarbonyl)-2-{(acetyloxyethylpiperazinylcarbamoylmethylcarbamoyl)ethylthiomethyl}-4-(hydroxy)]pyrrolidine in the yield of 78.2%.

IR(Neat)cm$^{-1}$: 1725, 1710–1690, 1610, 1580 NMR (CDCl$_3$) δ: 0.07 (6H,s), 0.09 (9H,s), 1.25–1.30 (2H,m), 1.85–2.20 (6H,m), 4.15–4.50 (4H,m), 3.77–3.90 (2H,m), 4.55–4.50 (2H,m), 5.24 (2H, d, J=6 Hz), 7.65–8.25 (4H, d, J=8 Hz)

Reference Example 22-D 2.55 g of the compound prepared in Reference Example 22-C was dissolved in 30 ml of anhydrous dichloromethane, and 0.61 g of methanesulfonyl chloride and 0.71 g of triethylamine were added to the resulting solution while stirring under ice-cooling. The mixture was then stirred for 2 hours at the same temperature. The reaction solution was washed with distilled water, 1N hydrochloric acid solution and saline, dried and concentrated under reduced pressure to obtain the desired product (2S,4S)-[1-(p-nitrobenzyloxycarbonyl)-2-{(acetyloxypiperazinylcarbamoylmethylcarbamoyl)ethylthiomethyl}-4-(mesyloxy)]pyrrolidine in the yield of 80.5%.

IR(Neat)cm$^{-1}$: 1710, 1690, 1510 NMR(CDCl$_3$) δ: 2.10–2.45 (6H,m), 3.03 (3H,m), 5.25 (2H,s), 7.53–8.24 (4H, d, J=8 Hz)

Reference Example 22-E

To 20 ml of dimethylformamide was added 1.5 g of the compound prepared in Reference Example 22-D and then 0.45 g of potassium thioacetate was added thereto. The reaction mixture was stirred for 4 hours at 70° to 80° C., cooled to room temperature, diluted with ethyl acetate, washed several times with distilled water, dried and then concentrated under reduced pressure. The residue was subjected to column chromatography eluting with ethyl acetate to obtain the desired product (2S,4S)-[1-(p-nitrobenzyloxycarbonyl)-2-{(acetyloxyethylpiperazinylcarbamoylmethylcarbamoyl)ethylthiomethyl}-4-(acetylthio)]pyrrolidine in the yield of 65.9%.

IR(Neat)cm$^{-1}$: 1725, 1690, 1420, 1350 NMR(CDCl$_3$) δ: 2.15–3.00 (6H,m), 3.21 (2H,m), 3.75–4.50 (4H,m), 5.23 (2H,s), 7.59–8.23 (4H, d, J=8 Hz)

Reference Example 22-F 2.5 g of the compound prepared in Reference Example 22-E was dissolved in 18 ml of methanol, and 0.31 g of sodium methoxide was added to the resulting solution while stirring under ice-cooling. The reaction mixture was then treated in the same manner as that of Reference Example 15-G to obtain the desired product (2S,4S)-[1-(p-nitrobenzyloxycarbonyl)-2-{(hydroxyethylpiperazinylcarbamoylmethylcarbamoyl)ethylthiomethyl}-4-(mercapto)]pyrrolidine in the yield of 60.1%.

IR(Neat)cm$^{-1}$: 1710, 1695, 1520, 1425, 1350 NMR (CDCl$_3$) δ: 1.65–1.75 (3H,m), 2.45–2.85 (4H,m), 2.90–3.30 (5H,m), 3.30 (2H,s), 5.24 (2H,s), 7.55–8.25 (4H, d, J=8 Hz)

Reference Example 23-A 10 g of (2S,4S)-[1-(p-nitrobenzyloxycarbonyl)-2-{(2-hydroxymethylcarbamoyl)ethylmercaptomethyl}-4-acetylthiopyrrolidine was dissolved in 30 ml of anhydrous ethyl acetate, and 5 ml of trichloroisocyanate was added dropwise to the resulting solution while stirring with ice-cooling under nitrogen atmosphere. The mixture was continuously stirred for 3 hours under ice-cooling. Then, the reaction solution was diluted with 50 ml of ethyl acetate, washed with aqueous sodium bicarbonate solution, distilled water and saline, respectively, and then dried. The residue was subjected to column chromatography eluting with ethyl acetate:n-hexane (4:1) to obtain the desired product (2S,4S)-1-(p-nitrobenzyloxycarbonyl)-2-{(2-trichloroacetylaminocarbonyloxymethylcarbamoly)ethymercaptomethyl}-4-acetylthiopyrrolidine in the yield of 52%.

IR(Neat)cm$^{-1}$: 1755–1750, 1725, 1680, 1600, 1400, 1335 NMR(CDCl$_3$) δ: 1.70–1.95 (3H,m), 2.45–2.85 (1H,m), 2.90–3.15 (2H,m), 3.25–3.50 (2H,m), 5.24–5.27 (2H,s), 7.55–8.27 (4H, d, J=8 Hz)

Reference Example 23-B 800 mg of the compound prepared in Reference Example 23-A was dissolved in 5 ml of methanol, and 3 ml of 1N-sodium hydroxide solution was added dropwise to the resulting solution while stirring under ice-cooling. The reaction mixture was stirred for 20 minutes under nitrogen atmosphere, adjusted to the neutral pH value with 1N hydrochloric acid solution, and then concentrated under reduced pressure. The residue was dissolved in ethyl acetate, washed with saline and distilled water, respectively, dried and then concentrated under reduced pressure to obtain an oily residue. The resulting oily residue was subjected to column chromatography eluting with ethyl acetate:n-hexane (5:1) to obtain the desired product (2S,4S)-(1-(p-nitrobenzyloxycarbonyl)-2-{(2-aminocarbonyloxymethylcarbamoyl)ethylmercaptomethyl}-4-mercaptopyrrolidine in the yield of 65%.

IR(Nujol)cm$^{-1}$: 1715, 1603, 1512, 1393, 1360 NMR (CDCl$_3$) δ: 1.65–1.95 (3H,m), 2.45–2.95 (2H,m), 3.01–3.20 (3H,m), 3.25–3.50 (2H,m), 3.84–4.30 (2H,m), 5.24 (2H,s), 7.55–8.27 (4H, d, J=8 Hz)

Reference Example 24-A

To 21 ml of anhydrous N,N-dimethylformamide were added 2 g of (2S,4R)-1-(p-nitrobenzyloxycarbonyl)-2-{(2-iodomethylcarbamoyl)ethylmercaptomethyl}-4-acetylthiopyrrolidine and 1.2 g of potassium phthalimide. The mixture was stirred for 6 hours at 90° to 95° C. The reaction solution was diluted with 50 ml of distilled water and then extracted three times with 50 ml of ethyl acetate in each time. The organic layers were combined, washed with saline and distilled water, respectively, dried and then concentrated under reduced pressure. The residue was subjected to column chromatography eluting with ethyl acetate:n-hexane (2:1) to obtain the desired product (2S,4R)-2-(p-nitrobenzyloxycarbonyl)-2-{(2-phthalimidoylmethylcarbamoyl)ethylmercaptomethyl}-4-acetylthiopyrrolidine in the yield of 72%.

IR(Neat)cm$^{-1}$: 1775, 1720, 1605, 1522, 1346, 1275 NMR (CDCl$_3$) δ: 2.28 (3H,s), 2.77 (3H,s), 5.18 (2H,s), 7.46 (2H, d, J=8 Hz), 8.16 (2H, d, J=8 Hz)

Reference Example 24-B

To 20 ml of anhydrous ethanol were added 2.5 g of the compound prepared in Reference Example 24-A and 2.3 g of hydrazine hydrate. The reaction mixture was stirred for about one hour under reflux and then cooled to room temperature. The mixture was filtered to remove the insoluble solid materials and then the filtrate was concentrated. The residue was dissolved in 30 ml of anhydrous tetrahydrofuran, and 2.1 g of trichloroacetylisocyanate was added to the resulting solution while stirring under ice-cooling. The mixture was stirred for 3 hours and then evaporated under reduced pressure to remove the reaction solvent. The residue was subjected to column chromatography eluting with ethyl acetate:n-hexan (3:1) to obtain the desired product (2S,4R)-1-(p-nitrobenzyloxycarbonyl)-2-{(2-trichloroacetylaminocarbonylaminomethylcarbamoyl) ethylmercaptomethyl}-4-acetylthiopyrrolidine in the yield of 58%.

IR(Neat)cm$^{-1}$: 1710, 1600, 1517, 1440, 1270

Reference Example 24-C 860 mg of the compound prepared in Reference Example 24-B was dissolved in 10 ml of anhydrous methanol, and 1.48 ml of 1N-sodium hydroxide solution was added dropwise to the resulting solution while stirring under ice-cooling. The reaction mixture was stirred for 2 hours at room temperature, neutralized with 1.5 ml of 1N-hydrochloric acid solution, and then concentrated under reduced pressure. The residue was diluted with 60 ml of ethyl acetate, washed with distilled water and then concentrated again under reduced pressure. The residue was subjected to column chromatography eluting with ethyl acetate:n-hexane (1:1) to obtain the desired product (2S,4R)-1-(p-nitrobenzyloxycarbonyl)-2-{(2-aminocarbonyl-aminomethylcarbamoyl)ethylmercaptomethyl}-4-mercaptopyrrolidine in the yield of 55%.

IR(Neat)cm$^{-1}$: 1710, 1665, 1590, 1510, 1425 NMR (CDCl$_3$) δ: 1.75–1.95 (3H,m), 2.45–2.8 (1H,m), 2.90–3.15 (2H,m), 3.21 (2H,s), 3.25–3.50 (2H,m), 3.84–4.30 (2H,m), 5.24 (2H,m), 7.55–8.27 (4H,d,J=8 Hz)

Reference Example 25-A

To 25 ml of anhydrous ethanol was added 1.05 g of the compound prepared in Reference Example 24-A. Then, 15 ml of saturated ammonia-methanol solution in anhydrous methanol was added thereto. The reaction mixture was stirred for 8 hours under reflux and concentrated under reduced pressure. The residue was diluted with ethyl acetate, washed with saline and distilled water, respectively, and then concentrated under reduced pressure. The residue was subjected to column chromatography eluting with ethyl acetate:n-hexane (3:1) to obtain the desired product (2S,4R)-1-(p-nitrobenzyloxycarbonyl)-2-{(2-aminomethylcarbamoyl)ethylmercaptomethyl}-4-acetylmercaptopyrrolidine in the yield of 82%.

IR(Neat)cm$^{-1}$: 1715, 1603, 1512, 1400–1390 NMR (CDCl$_3$) δ: 2.28–2.68 (1H,m), 3.03–3.70 (8H,m), 3.80–4.24 (2H,m), 5.16 (2H,s), 7.49–8.17 (4H,d,J=8 Hz)

Reference Example 25-B

To 15 ml of anhydrous methylene chloride was added 610 mg of the compound prepared in Reference Example 25-A. While stirring under ice-cooling, 500 mg of p-nitrobenzyloxy carbonylchloroformate and 400 mg of triethylamine were added to the mixture. The reaction mixture was stirred for 2 hours and then diluted with 30 ml of methylene chloride, washed with 1N-hydrochloric acid solution, 10% sodium carbonate solution and distilled water, respectively, dried and then concentrated under reduced pressure. The residue was subjected to column chromatography eluting with ethyl acetate:n-hexane (4:1) to obtain the desired product (2S, 4R)-1-(p-nitrobenzyloxycarbonyl)-2-{ (2-nitrobenzyloxycarbonylaminomethylcarbamoyl) ethylmercaptomethyl}-4-acetylthiopyrrolidine in the yield of 75%.

IR(Neat)cm$^{-1}$: 1760, 1715, 1690, 1550, 1480 NMR (CDCl$_3$) δ: 2.40–3.10 (5H,m), 3.15–3.60 (2H,m), 5.15–5.35 (4H,m), 7.35–7.70 (7H,m), 7.75–8.15 (2H,m), 8.22 (4H, br. J=8 Hz)

Reference Example 25-C 710 mg of the compound prepared in Reference Example 25-B was dissolved in 10 ml of anhydrous methanol and this reaction mixture was treated in the same manner as that of Reference Example 24-C to obtain the desired product (2S, 4R)-1-(p-nitrobenzyloxycarbonyl)-2-{(4-nitrobenzyloxycarbonylaminomethylcarbamoyl) ethylmercaptomethyl}-4-mercaptopyrrolidine in the yield of 55%.

IR(Neat)cm$^{-1}$: 1710–1700, 1610, 1530–1520, 1350 NMR (CDCl$_3$) δ: 1.60–2.00 (2H,m), 2.30–3.65 (8H,m), 3.80–4.35 (2H,m), 5.20 (4H,s), 7.50–7.55 (4H,d,J=8 Hz), 8.21 (4H,d, J=8 Hz)

Reference Example 26-A 1.3 g of (2S,4R)-1-(p-nitrobenzyloxycarbonyl)-2-{(2-hydroxymethylcarbamoyl)ethylmercaptomethyl}-4-acetylthiopyrrolidine was added to 30 ml of anhydrous methylene chloride. To this reaction mixture were added 2 ml of a solution of diazomethane dissolved in ethyl ether and a catalytic amount of boron trifluoride-etherate complex while stirring under ice-cooling, and then the whole mixture was stirred for 30 minutes. The reaction solution was washed with saline and filtered to remove the insoluble solid materials. The filtrate was washed with aqueous sodium bicarbonate solution, saline and distilled water, respectively. The organic layer was separated and concentrated under reduced pressure. The residue was subjected to column chromatography eluting with ethyl acetate:n-hexane (10:1) to obtain the desired product (2S,4R)-1-[(p-nitrobenzyloxycarbonyl)-2-{(methoxymethylcarbamoyl) ethylmercaptomethyl}-4-acetylmercaptopyrrolidine in the yield of 62%.

IR(Neat)cm$^{-1}$: 1710, 1690, 1685, 1520, 1390 NMR (CDCl$_3$) δ: 2.46–2.95 (2H,m), 3.15 (3H,s), 3.85–4.15 (3H, m) 5.16 (2H,s), 7.49–8.17 (4H, br. J=8 Hz)

Reference Example 26-B 910 mg of the compound prepared in Reference Example 26-A was added to 15 ml of anhydrous methanol, and the reaction mixture was treated in the same manner as that of Reference Example 24-C to obtain the desired product (2S,4R)-1-(p-nitrobenzyloxycarbonyl)-2-{(methoxymethylcarbamoyl)ethylmercaptomethyl}-4-mercaptopyrrolidine in the yield of 50%.

IR(Neat)cm$^{-1}$: 1710–1700, 1690–1680, 1550–1540, 1390
NMR(CDCl$_3$) δ: 1.60–2.05 (2H,m), 2.33–3.10 (2H,m), 3.15 (3H,s), 3.30–3.80 (5H,m), 3.85–4.33 (2H,m), 5.24 (2H,s), 7.56–8.26 (2H,d,J=8 Hz)

What is claimed is:

1. A mercaptopyrrolidine derivative represented by the following formula (III):

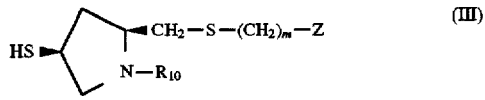

or a pharmaceutically acceptable salt thereof, in which $R_{10}$ is an imino-protecting group, Z is

or $R_9$ $R_4$ is amino which is optional substituted with a group of formula

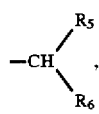

wherein $R_5$ and $R_6$ independently of one another are hydrogen, cyano, cyano(lower)alkyl, methoxy, hydroxy, hydroxy(lower)alkyl, carbamoyl, carbamoyl(lower)alkyl, carbamoyloxy, ureido, ureido(lower)alkyl, amino, amino(lower)alkyl, methoxymethyloxy, methoxymethyloxymethyl, methylcarbamoyloxy, 2-hydroxyethyl piperazinyl carbonyl, aminoethyl piperazinyl carbonyl, 4-cyanoethyl piperazinyl carbonyl, 2-methoxyethyl piperazinyl carbonyl, 2-carbamoyloxyethyl piperazinyl carbonyl, or 2-ureidoethyl piperazinyl carbonyl, or ($C_{2-C5}$) heterocyclic amine which is optionally substituted with carbamoyl; provided that $R_5$ and $R_6$ are not hydrogen at the same time, $R_9$ is hydroxy, hydroxy(lower)alkyl, carbamoyloxy, or hydroxyethyl piperazinyl carbonyl and m is an integer of 1 to 6, provided that when m is 1, $R_4$ is not an unsubstituted amino(—NH$_2$).

* * * * *